(12) United States Patent
Caturla Javaloyes et al.

(10) Patent No.: US 7,906,530 B2
(45) Date of Patent: Mar. 15, 2011

(54) 1,7-NAPHTHYRIDINE DERIVATIVES AS P38 MAP KINASE INHIBITORS

(75) Inventors: Juan Francisco Caturla Javaloyes, Barcelona (ES); Laura Vidal Gispert, Barcelona (ES); Wenceslao Lumeras Amador, Sant Just Desvern (ES)

(73) Assignee: Laboratorios Almirall, S.A., Barcelona (ES)

( * ) Notice: Subject to any disclaimer, the term of this patent is extended or adjusted under 35 U.S.C. 154(b) by 62 days.

(21) Appl. No.: 12/376,499

(22) PCT Filed: Aug. 7, 2007

(86) PCT No.: PCT/EP2007/006981
§ 371 (c)(1),
(2), (4) Date: Apr. 1, 2009

(87) PCT Pub. No.: WO2008/017461
PCT Pub. Date: Feb. 14, 2008

(65) Prior Publication Data
US 2010/0227881 A1 Sep. 9, 2010

(30) Foreign Application Priority Data
Aug. 9, 2006 (ES) .................................. 200602174

(51) Int. Cl.
*C07D 471/02* (2006.01)
(52) U.S. Cl. ........................................ 514/300; 546/122
(58) Field of Classification Search .................. None
See application file for complete search history.

(56) References Cited

U.S. PATENT DOCUMENTS
4,550,166 A 10/1985 Moran et al.

FOREIGN PATENT DOCUMENTS

| | | |
|---|---|---|
| JP | 57-203068 | 12/1982 |
| WO | WO 99/01449 | 1/1999 |
| WO | WO 00/63204 | 10/2000 |
| WO | WO 00/66583 | 11/2000 |
| WO | WO 01/01986 | 1/2001 |
| WO | WO 01/29042 | 4/2001 |
| WO | WO 02/02549 A1 | 1/2002 |
| WO | WO 02/46184 | 6/2002 |
| WO | WO 02/058695 | 8/2002 |
| WO | WO 02/072576 | 9/2002 |
| WO | WO 02/072579 | 9/2002 |
| WO | WO 03/008413 | 1/2003 |
| WO | WO 03/033502 | 4/2003 |
| WO | WO 03/087087 | 10/2003 |
| WO | WO 03/097062 | 11/2003 |
| WO | WO 03/103590 | 12/2003 |
| WO | WO 2004/010995 | 2/2004 |
| WO | WO 2004/014900 | 2/2004 |
| WO | WO 2004/020438 | 3/2004 |
| WO | WO 2004/020440 | 3/2004 |
| WO | WO 2004/074290 | 9/2004 |
| WO | WO 2005/018624 | 3/2005 |
| WO | WO 2005/032551 | 4/2005 |
| WO | WO 2005/070929 | * 8/2005 |
| WO | WO 2005/073219 | 8/2005 |
| WO | WO 2008/107125 | 9/2008 |

OTHER PUBLICATIONS

Bao J. et al. "p38 MAP kinase inhibitors: Metabolically stabilized piperidine-substituted quinolinones and naphthyridines," *Bioorganic & Medicinal Chemistry Letters* 16(1): 64-68 (2006).

Gavrin, LK et al. "Inhibition of Tpl2 kinase and TNF-α production with 1,7-naphthyridine-3-carbonitriles: Synthesis and structure-activity relationships," *Bioorganic & Medicinal Chemistry Letters* 15(23): 5288-5292 (2005).

International Search Report mailed Oct. 18, 2007, for International Application No. PCT/EP2007/006981 (WO 2008/017461 A1).

Adams, R. H. et al. "Essential Role of p38α MAP Kinase in Placental but not Embryonic Cardiovascular Development," Molecular Cell, 6:109-116 (2000).

Hale, K. K. et al. "Differential Expression and Activation of p38 Mitogen-Activated Protein Kinase α, β, γ, and σ in Inflammatory Cell Lineages," The Journal of Immunology, 162:4246-4252 (1999).

Wang, X. S. et al. "Molecular Cloning and Characterization of a Novel p38 Mitogen-activated Protein Kinase," The Journal of Biological Chemistry, 272(38):23668-23674 (1997).

U.S. Appl. No. 12/529,490, filed Sep. 1, 2009, Vidal Juan et al.

Allen, M. et al. "Deficiency of the Stress Kinase p38α Results in Embryonic Lethality: Characterization of the Kinase Dependence of Stress Responses of Enzyme-deficient Embryonic Stem Cells," *J. Exp. Med.* 191(5): 859-869 (2000).

(Continued)

*Primary Examiner* — Brandon J Fetterolf
*Assistant Examiner* — Anna Pagonakis
(74) *Attorney, Agent, or Firm* — Finnegan, Henderson, Farabow, Garrett & Dunner LLP

(57) ABSTRACT

New inhibitors of the p38 mitogen-activated protein kinase having the general formula (I) are disclosed, as well as processes for their preparation, pharmaceutical compositions comprising them, and their use in therapy.

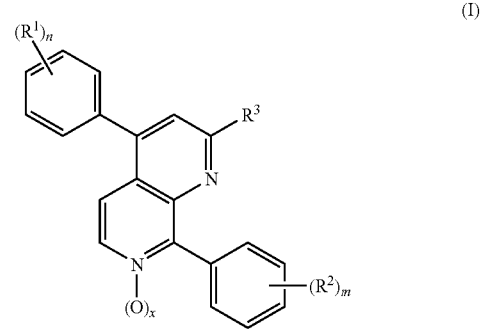

16 Claims, No Drawings

OTHER PUBLICATIONS

Amato, JS et al. "Synthesis of 1-*tert*-Butyl-4-chloropiperidine: Generation of an *N-tert*-Butyl Group by the Reaction of a Dimethyliminium Salt with Methylmagnesium Chloride," *The Journal of Organic Chemistry*, 70(5): 1930-1933 (2005).

Beardmore, VA et al. "Generation and Characterization of p38β (MAPK11) Gene Targeted Mice," *Molecular and Cellular Biology*, 25(23): 10454-10464 (2005).

Brancho, D. et al. "Mechanism of p38 MAP kinase activation in vivo," *Genes & Development*, 17: 1969-1978 (2003).

Cheng, C. et al. "The Friedländer Synthesis of Quinolines," *Org. Recat.*, Chapter 2, 37-201 (1982).

Hideshima, T. et al. "Targeting p38 MAPK inhibits multiple myeloma cell growth in the bone marrow milieu," *Blood*, 101(2): 703-705 (2003).

Hildesheim, J. et al. "p38 Mitogen-Activated Protein Kinase Inhibitor Protects the Epidermis Against the Acute Damaging Effects of Ultraviolet Irradiation by Blocking Apoptosis and Inflammatory Responses," *The Journal of Investigative Dermatology*, 122:497-502 (2004).

Hollenbach, E. et al. "Inhibition of RICK/Nuclear Factor-κB and p38 Signaling Attenuates the Inflammatory Response in a Murine Model of Crohn Disease," *The Journal of Biological Chemistry*, 280(15): 14981-14988 (2005).

International Search Report mailed May 28, 2008, for International Application No. PCT/EP2008/001616 (WO 2008/107125 A1).

Jin, S. et al. "p38 Mitogen-Activated Protein Kinase is Activated After a Spinal Nerve Ligation in Spinal Cord Microglia and Dorsal Root Ganglion Neurons and Contributes to the Generation of Neuropathic Pain," *The Journal of Neuroscience*, 23(10): 4017-4022 (2003).

Katsoulidis, E. et al. "Role of the p38 Mitogen-Activated Protein Kinase Pathway in Cytokine-Mediated Hematopoietic Suppression in Myelodysplastic Sydromes," *Cancer Research*, 65(19): 9029-9037 (2005).

Kotlyarov, A. et al. "MAPKAP Kinase 2 is essential for LPS-induced TNF-α biosynthesis," *Nature Cell Biology*, 1: 94-97 (1999).

Kumar, S. et al. "p38 Map Kinases: Key Signaling Molecules as Therapeutic Targets for Inflammatory Diseases," *Nature Reviews Drug Discovery*, 2: 717-726 (2003).

Kyriakis, JM et al. "Mammalian Mitogen-Activated Protein Kinase Signal Transduction Pathways Activated by Stress and Inflammation," *Physiological Reviews*, 81(2): 807-869 (2001).

Lee, JC et al. "A protein kinase involved in the regulation of inflammatory cytokine biosynthesis," *Nature*, 372(22/29): 739-746 (1994).

Miyaura, N. et al. "Palladium-Catalyzed Cross-Coupling Reactions of Organoboron Compounds," *Chem. Rev.*, 95(7): 2457-2483 (1995).

Negishi, E. et al. "Novel Stereoselective Alkenyl-Aryl Coupling via Nickel-catalysed Reaction of Alkenylalanes with Aryl Halides," *J.C.S. Chem. Comm.*, 596-597 (1976).

Moran, DB et al. "Synthesis of (Pyridinyl)-1,2,4-triazolo[4,3-*a*]pyridines," J. Heterocyclic Chem., 23: 1071-1077 (1986).

Nick, JA et al. "Selective Suppression of Neutrophil Accumulation in Ongoing Pulmonary Inflammation by Systemic Inhibition of p38 Mitogen-Activated Protein Kinase," *The Journal of Immunology*, 169: 5260-5269 (2002).

Pargellis, C. et al. "Inhibitors of p38 mitogen-activated protein kinase for the treatment of rheumatoid arthritis," *Current Opinion in Investigational Drugs*, 4(5): 566-571 (2003).

Sabio, G. et al. "p38γ regulates the localisation of SAP97 in the cytoskeleton by modulating its interaction with GKAP," *The EMBO Journal*, 24(6): 1134-1145 (2005).

Saccani, S. et al. "p38-dependent marking of inflammatory genes for increased NF-κB recruitment," *Nature Immunology*, 3(1): 69-75 (2002).

Schäfers, M. et al. "Tumor Necrosis Factor-α Induces Mechanical Allodynia After Spinal Nerve Ligation by Activation of p38 MAPK in Primary Sensory Neurons," *The Journal of Neuroscience*, 23(7): 2517-2521 (2003).

See, F. et al. "p38 MAP kinase as a therapeutic target in cardiovascular disease," *Drug Discovery Today: Therapeutic Strategies*, 1(2): 149-154 (2004).

Shi, Y. et al. "In the Cellular Garden of Forking Paths: How p38 MAPKs Signal for Downstream Assistance," *Biol. Chem.*, 383(10): 1519-1536 (2002).

Tamura, K. et al. "Requirement for p38α in Erythropoietin Expression: A Role for Stress Kinases in Erythropoiesis," *Cell*, 102: 221-231 (2000).

Tsuda, M. et al. "Activation of p38 Mitogen-Activated Protein Kinase in Spinal Hyperactive Microglia Contributes to Pain Hypersensitivity Following Peripheral Nerve Injury," *GLIA*, 89:89-95 (2004).

Underwood, DC et al. "SB 239063, a p38 MAPK inhibitor, reduces neutrophilia, inflammatory cytokines, MMP-9, and fibrosis in lung," *Am. J. Physiol. Lung Cell Mol. Physiol.*, 279: L895-L902 (2000).

Waetzig, GH et al. "p38 Mitogen-Activated Protein Kinase Is Activated and Linked to TNF-α Signaling in Inflammatory Bowel Disease," *The Journal of Immunology*, 168: 5342-5351 (2002).

English Language Abstract for JP 57-203068, which published on Dec. 13, 1982.

Gilman, H. et al. "Some Substituted Isoquinolines," *Journal of American Chemical Society* 69(8): 1946-1948 (1947).

\* cited by examiner

1,7-NAPHTHYRIDINE DERIVATIVES AS P38 MAP KINASE INHIBITORS

This application is a national stage filing under 35 U.S.C. §371 of International Application No. PCT/EP2007/006981 filed on 7 Aug. 2007, which claims priority of Spanish Patent Application No. P200602174, filed on 9 Aug. 2006. The contents of both applications are incorporated herein by reference.

The present invention relates to new inhibitors of the p38 mitogen-activated protein kinase.

MAP kinases are evolutionary conserved enzymes translating membrane signals into gene expression responses. In mammals, four MAPK families can be distinguished: extracellular signal-related kinases (ERK1/2), Jun amino terminal kinases (JNK1/2/3), p38 proteins (alpha, beta, gamma and delta) and ERK5. The regulation of these proteins is exerted by a three-tier cascade composed of MAPK, MAPK kinase, and MAPK kinase kinase.

p38 MAPK was originally identified as the target of CSAIDs (cytokine suppressive anti-inflammatory drugs), having a central role in the signal transduction pathway leading to the production of TNF-alpha and other cytokines (Lee et al, 1984). p38 is activated by phosphorylation in Thr and Tyr by either MKK3, MKK4, or MKK6 (Kyriakis and Avruch, 2001) in response to stress and pro-inflammatory stimuli. In turn, p38 phosphorylates its effectors in Ser and Thr residues, namely protein kinases phosphatases and transcription factors, such as ATF-2, MEF2, MAPKAPK2, MSK1/2 or MNK1/2. Altogether this activation cascade results in control of gene expression through four different mechanisms: transcription factor activation; mRNA stabilization; mRNA translation; and histone phosphorylation at NF-kB binding sites in chromatin (Shi and Gaestel, 2002; Sacanni et al, 2001).

There are four different p38 isoforms encoded by separate genes: p38 alpha, beta, gamma and delta, each one showing a distinct tissue expression pattern. As assessed by mRNA and protein levels (Beardmore et al, 2005; Wang et al, 1997), p38 alpha and beta are ubiquitously expressed, with p38 beta expression being more relevant in CNS tissues (brain, cortex, cerebellum, hippocampus, etc). The expression of p38 gamma is more prominent in skeletal muscle while p38 delta localizes mainly in heart, kidney, lung and adrenal gland. At the cellular level, p38 alpha and delta seem to be the most relevant isoforms in immune cells (monocytes, macrophages, neutrophils and T cells) (Hale et al, 1999). Pharmacological inhibition with specific p38alpha/beta inhibitors as well as gene targeting studies have indicated that p38alpha is the isoform regulating inflammatory responses most probably through its downstream substrate MAPKAP-K2 (Kotlyarov et al, 1999). Likewise, this isoform is necessary in early embryonic development as p38alpha KO (knock-out) mice die in embryonic day 12.5 due to placental insufficiency and vascular defects (Allen et al, 2000; Tamura et al, 2000; Adams et al, 2000), a phenotype that is also reproduced in the MKK3/MKK6 double KO mice (Brancho et al, 2003). In contrast, p38 beta, gamma and delta knock-out mice do not show any developmental deficiencies (Beardmore et at 2005; Sabio et al, 2005). p38 beta KO mice appear to respond similarly to pro-inflammatory stimuli (LPS) as wild type controls, indicating that this isoform does not have a role in inflammation (Beardmore et at 2005).

The contribution of the p38MAPK pathway to inflammation has been studied both in vitro and in vivo by employing different chemical series of p38 inhibitors (Pargellis and Regan, 2003; Kumar et al, 2003). The most widely used inhibitor molecule, SB203580, is, in fact, a dual p38alpha/beta inhibitor. Inhibition of p38 abrogates the release of TNF-alpha as well as other pro-inflammatory cytokines such as IL-1, IL-6, and IL-8, in PBMC, whole blood, or the human monocytic cell line THP-1.

By virtue of the involvement of p38 in TNFalpha production, inhibitors of p38 have been tested in animal models of diseases in which TNFalpha has a pathophysiological role. p38 inhibition decreases murine collagen-induced arthritis and rat adjuvant-induced arthritis severity (Pargellis and Regan, 2003). Furthermore, p38 inhibitors also improve bone resorption in animal models of arthritis, probably due to the implication of p38 MAPK in the differentiation of osteoclasts. p38 inhibition attenuates the inflammatory response in a murine model of Crohn's disease and diminishes TNF-alpha production in human Crohn's disease patient biopsies (Hollenbach et at 2005; Waetzig et al, 2002). Due to the exclusive usage of the p38 pathway by neutrophils, p38 has also been considered a target for chronic obstructive pulmonary disease (COPD) (Nick et al, 2002). p38 inhibition reduces neutrophilia, inflammatory cytokines, MMP-9 and fibrosis in lung (Underwood et al, 2000). In skin models of irradiation, inhibition of p38 protects the epidermis against acute ultraviolet radiation exposure by blocking apoptosis and inflammatory responses (Hildesheim et al, 2004). p38 inhibition also reverses hematopoietic defects in bone marrow from patients with myelodysplastic syndromes, in which TNF-alpha overproduction has a pathophysiological role (Katsoulidis et al, 2005).

In hematopoietic malignancies, a study has shown that p38 inhibitors can block the proliferation of multiple myeloma cells by inhibiting the production of IL-6 and VEGF in bone marrow stromal cells (Hideshima et al, 2002).

p38 is involved in key cellular mechanisms such as apoptosis, fibrosis and cellular hypertrophy, which are common to cardiac and vascular pathologies. Pharmacological inhibition of p38 has proven useful in improving ischemia-reperfusion injury, cerebral focal ischemia, acute coronary syndrome, chronic heart failure and post-myocardial infarction remodelling (See et al, 2004).

Experimental inhibition of p38 has been reported effective in reducing pain in animal models of neuropathy that rely on COX-2 expression and TNF-alpha production by glial cells (Schafers et al, 2003; Jin et al, 2003; Tsuda et al, 2004).

Therefore, the compounds of the invention may be useful in the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, immune and inflammatory diseases, destructive bone disorders, neoplastic disorders, neurodegenerative disorders, viral diseases, infectious diseases, cardiovascular diseases, angiogenesis-related disorders, and pain-related disorders.

Autoimmune diseases which may be prevented or treated include but are not limited to psoriasis, rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease.

Immune and inflammatory diseases which may be prevented or treated include but are not limited to asthma, COPD, respiratory distress syndrome, acute or chronic pancreatitis, graft versus-host disease, Behcet syndrome, inflammatory eye conditions such as conjunctivitis and uveitis, psoriasis, contact dermatitis, atopic dermatitis, sarcoidosis, gout, pyresis, transplant rejection, allergic rhinitis, allergic conjunctivitis, Cardiovascular diseases which may be prevented or treated include but are not limited to ischemia-reperfusion injury, cerebral focal ischemia, acute coronary syndrome, congestive heart failure, cardiomyopathy, myocarditis, atherosclerosis, vasculitis and restenosis.

Destructive bone disorders which may be prevented or treated include but are not limited to osteoporosis, osteoarthritis and multiple myeloma-related bone disorder.

Neoplastic disorders which may be prevented or treated include but are not limited to solid tumors such as Kaposi's sarcoma, metastatic melanoma, and hematopoietic malignancies such as acute or chronic myelogenous leukemia and multiple myeloma.

Neurodegenerative diseases which may be prevented or treated include but are not limited to Parkinson's disease, Alzheimer's disease, neurodegenerative disease caused by traumatic injury, or Huntington's disease.

Viral diseases which may be prevented or treated include but are not limited to acute hepatitis infection (including hepatitis A, hepatitis B and hepatitis C), HIV infection, Epstein-Barr infection, CMV retinitis, SARS or avian influenza A infection.

Infectious diseases which may be prevented or treated include but are not limited to sepsis, septic shock, endotoxic shock, Gram negative sepsis, toxic shock syndrome, Shigellosis, or cerebral malaria.

Angiogenesis-related disorders which may be prevented or treated include but are not limited to hemangiomas, ocular neovascularization, macular degeneration or diabetic retinopathy.

Pain-related disorders which may be prevented or treated include but are not limited to neuropathic pain (such as diabetic neuropathy, post-herpetic or trigeminal neuralgia), cancer-related pain, chronic pain (such as lower back pain syndrome), and inflammatory pain.

Other miscellaneous diseases or disorders which may be prevented or treated include but are not limited to myelodysplastic syndrome, cachexia, endometriosis, acute skin injuries such as sunburn, and wound healing.

In view of the physiological effects mediated by inhibition of the p38 mitogen-activated protein kinase, several compounds have been recently disclosed for the treatment or prevention of rheumatoid arthritis, ischemia-reperfusion injury, cerebral focal ischemia, acute coronary syndrome, COPD, Crohn's disease, irritable bowel syndrome, adult respiratory distress syndrome, osteoporosis, neurodegenerative diseases such as Alzheimer's disease, rheumatoid spondylitis, psoriasis, atherosclerosis, osteoarthritis, multiple myeloma. See for example WO 99/01449, WO 00/63204, WO 01/01986, WO 01/29042, WO 02/046184, WO 02/058695, WO 02/072576, WO 02/072579, WO 03/008413, WO 03/033502, WO 03/087087, WO 03/097062, WO 03/103590, WO 2004/010995, WO 2004/014900, WO 2004/020438, WO 2004/020440, WO 2005/018624, WO 2005/032551, WO 2005/073219.

It has now been found that certain 1,7-naphthyridine derivatives are novel potent inhibitors of the p38 mitogen-activated protein kinase and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by inhibition of the p38 mitogen-activated protein kinase; and methods of treatment of pathological conditions or diseases susceptible to amelioration by inhibition of the p38 mitogen-activated protein kinase comprising the administration of the compounds of the invention to a subject in need of treatment.

Thus, the present invention is directed to new 1,7-naphthyridine derivatives of formula (I)

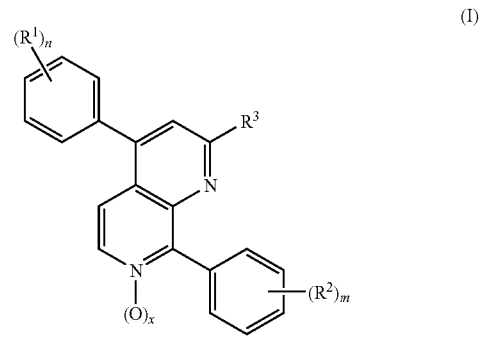

wherein:
$R^1$ represents a halogen atom, a $C_{1-4}$ alkyl group optionally substituted by one, two or three halogen atoms or $C_{1-4}$ alkoxy group.
$R^2$ represents a halogen atom or a group selected from hydroxy, $C_{1-4}$ alkyl, $C_{1-4}$ alkoxy, $C_{1-4}$ alkylthio, $C_{1-4}$ alkoxy-$C_{1-4}$ alkoxy, morpholin-$C_{1-4}$ alkoxy, $C_{1-4}$ alkanesulfonamide and $C_{1-4}$ alkoxy-$C_{1-4}$ alkylcarbamoyl.
$R^3$ represents a hydrogen atom or a group of formula -L-$G^1$ wherein L is a linker selected from the group consisting of a direct bond, —O—, —S— and —NH— and $G^1$ is a ring system selected from aromatic or non-aromatic heterocycles which cycles are optionally substituted with one or two groups selected from halogen atoms, amino groups, mono- or di-$C_{1-4}$ alkylamino groups, $C_{1-4}$ alkyl groups, $C_{1-4}$ alkoxy groups and $C_{3-6}$ cycloalkyl groups.
n is an integer from 0 to 4
m is an integer from 0 to 4
x has the value of zero or one;
and pharmaceutically acceptable salts thereof.

To avoid any confusion, it is clarified that in the above formula when x has the value of zero the compounds of formula (I) are 1,7-naphthyridines and when x has the value of one the compounds are 1,7-naphthyridine 7-oxides.

As used herein the term alkyl embraces optionally substituted, linear or branched radicals having 1 to 8, preferably 1 to 6 and more preferably 1 to 4 carbon atoms. The substituents in said alkyl groups are selected from halogen atoms.

Examples include methyl, ethyl, n-propyl, i-propyl, n-butyl, sec-butyl and tert-butyl radicals.

As used herein, the term alkoxy embraces optionally substituted, linear or brached oxy-containing radicals each having alkyl portions of 1 to 8, preferably 1 to 6 and more preferably 1 to 4 carbon atoms. The substituents in said alkoxy groups are selected from halogen atoms.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term alkylthio embraces radicals containing an optionally substituted, linear or brached alkyl radicals of 1 to 8, preferably 1 to 6 and more preferably 1 to 4 carbon atoms. The substituents in said alkylthio groups are selected from halogen atoms.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio or 2-hydroxypropylthio.

As used herein, the term monoalkylamino embraces radicals containing an optionally substituted, linear or brached alkyl radicals of 1 to 8 carbon atoms attached to a divalent —NH— radical. More preferred monoalkylamino radicals are "lower monoalkylamino" radicals having 1 to 6, more preferably 1 to 4 carbon atoms.

Preferred optionally substituted monoalkylamino radicals include methylamino, ethylamino, n-propylamino, i-propylamino, n-butylamino, sec-butylamino and t-butylamino.

As used herein, the term dialkylamino embraces radicals containing trivalent nitrogen atoms with two optionally substituted, linear or brached alkyl radicals of 1 to 8 carbon atoms attached thereto. More preferred dialkylamino radicals are "lower dialkylamino" radicals having 1 to 6, more preferably 1 to 4 carbon atoms in each alkyl radical.

Preferred optionally substituted dialkylamino radicals include dimethylamino, diethylamino, methyl(ethyl)amino, di(n-propyl)amino, n-propyl(methyl)amino, n-propyl(ethyl)amino, di(i-propyl)amino, i-propyl(methyl)amino, i-propyl(ethyl)amino, di(n-butyl)amino, n-butyl(methyl)amino, n-butyl(ethyl)amino, n-butyl(i-propyl)amino, di(sec-butyl)amino, sec-butyl(methyl)amino, sec-butyl(ethyl)amino, sec-butyl(n-propyl)amino, sec-butyl(i-propyl)amino, di(t-butyl)amino, t-butyl(methyl)amino, t-butyl(ethyl)amino, t-butyl(n-propyl)amino, t-butyl(i-propyl)amino.

As used herein, the term alkanesulfonamide embraces radicals containing an optionally substituted, linear or brached alkyl radical of 1 to 4 carbon atoms and attached to the sulphur atom of a —SO$_2$NH— radical.

Preferred alkanesulfonamide radicals are unsubstituted radicals selected from the list comprising methylsulfonamido, ethylsulfonamido, n-propylsulfonamido, i-propylsulfonamido, n-butylsulfonamido, sec-butylsulfonamido and t-butylsulfonamido.

As used herein, the term monoalkylcarbamoyl embraces radicals containing an optionally substituted, linear or brached alkyl radicals of 1 to 4 carbon atoms and attached to the nitrogen of a —NHCO— radical.

Preferred monoalkylcarbamoyl radicals include methylcarbamoyl, ethylcarbamoyl, n-propylcarbamoyl, i-propylcarbamoyl, n-butylcarbamoyl, sec-butylcarbamoyl, t-butylcarbamoyl.

As used herein, the term $C_{1-4}$alkoxy-$C_{1-4}$-alkylcarbamoyl embraces radicals containing an alkoxy radical of 1 to 4 carbon atoms attached to an alkylene radical having 1 to 4 carbon atoms which alkylene radical is attached to the nitrogen of a —NHCO— radical.

Preferred $C_{1-4}$alkoxy-$C_{1-4}$-alkylcarbamoyl radicals include methoxymethylcarbamoyl, methoxyethylcarbamoyl, ethoxymethylcarbamoyl, ethoxyethylcarbamoyl, methoxyproylcarbamoyl and ethoxyproylcarbamoyl.

As used herein, the term cyclic group embraces, unless otherwise specified, carbocyclic and heterocyclic radicals. The cyclic radicals can contain one or more rings. Carbocyclic radicals may be aromatic or alicyclic, for example cycloalkyl radicals. Heterocyclic radicals also include heteroaryl radicals.

As used herein, the term cycloalkyl embraces saturated carbocyclic radicals and, unless otherwise specified, a cycloalkyl radical typically has from 3 to 6 carbon atoms. Examples include cyclopropyl, cyclobutyl, cyclopentyl and cyclohexyl. It is preferably cyclopropyl, cyclopentyl or cyclohexyl. When a cycloalkyl radical carries 2 or more substituents, the substituents may be the same or different.

As used herein, the term aromatic group embraces typically a 5- to 14-membered aromatic ring system, such as a 5- or 6-membered ring which may contain one or more heteroatoms selected from O, S and N. When no heteroatoms are present the radical is named aryl radical and when at least one heteroatom is present it is named heteroaryl radical. The aromatic radical can be monocyclic such as phenyl or pyridyl or polycyclic, such as naphthyl or quinolyl. When an aromatic radical or moiety carries 2 or more substituents, the substituents may be the same or different.

As used herein, the term aryl radical embraces typically a $C_5$-$C_{14}$ monocyclic or polycyclic aryl radical such as phenyl or naphthyl, anthranyl or phenanthryl. Phenyl is preferred. When an aryl radical carries 2 or more substituents, the substituents may be the same or different.

As used herein, the term heteroaryl radical (also named aromatic heterocycle) embraces typically a 5- to 14-membered ring system comprising at least one heteroaromatic ring and containing at least one heteroatom selected from O, S and N. A heteroaryl radical may be a single ring or two or more fused rings wherein at least one ring contains a heteroatom.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl and pyrazolyl radicals. Pyridyl, thienyl, furanyl, pyridazinyl, pyrimidinyl and quinolyl radicals are preferred.

When a heteroaryl radical carries 2 or more substituents, the substituents may be the same or different.

As used herein, the term non-aromatic heterocyclic group embraces typically a non-aromatic, saturated or unsaturated $C_3$-$C_{10}$carbocyclic ring, such as a 5, 6 or 7 membered radical, in which one or more, for example 1, 2, 3 or 4 of the carbon atoms preferably 1 or 2 of the carbon atoms are replaced by a heteroatom selected from N, O and S. Saturated heterocyclyl radicals are preferred. A heterocyclic radical may be a single ring or two or more fused rings wherein at least one ring contains a heteroatom. When a heterocyclyl radical carries 2 or more substituents, the substituents may be the same or different.

Examples of heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl. Where a heterocyclyl radical carries 2 or more substituents, the substituents may be the same or different.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

When aromatic or non-aromatic heterocycles are substituted it is preferred that the substituents are selected from the group consisting of halogen atoms, $C_{1-4}$ alkyl groups, $C_{1-4}$ alkoxy groups and trifluoromethyl groups.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

In one embodiment of the present invention the compounds are 1,7-naphthyridine-7-oxides, i.e. compounds of formula (I) wherein x has a value of 1.

In another embodiment of the present invention n is 1 or 2 and each $R^1$ independently represents an halogen atom or a $C_{1-4}$ alkyl group. In a more specific embodiment at least one group $R^1$ is at an ortho position with respect to the carbon atom through which the phenyl group is attached to the naphtyridine core. In yet a more specific embodiment n is 2, and both groups $R^1$ are halogen atoms, preferably selected from chlorine or fluorine atoms.

In another embodiment of the present invention m is 1 or 2 and each $R^2$ independently represents an halogen atom or a $C_{1-4}$ alkyl group. In a more specific embodiment at least one group $R^2$ is at an ortho position with respect to the carbon atom through which the phenyl group is attached to the naphtyridine core. In yet a more specific embodiment m is 2 and the two groups $R^2$ are at an ortho position with respect to the carbon atom through which the phenyl group is attached to the naphthyridine core. In still a more specific embodiment both $R^2$ groups are halogen atoms, preferably selected from chlorine or fluorine atoms.

In another embodiment of the present invention $R^3$ represents a hydrogen atom or a group of formula -L-$G^1$ wherein L is a linker selected from the group consisting of a direct bond, —O—, —S— and —NH— and $G^1$ is a ring system selected from optionally substituted, nitrogen-containing, aromatic or non-aromatic heterocycles.

In a more specific embodiment of the present invention $R^3$ represents a hydrogen atom or a group of formula

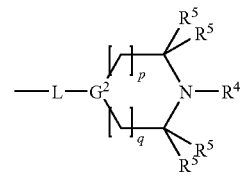

wherein $G^2$ is either a group selected from —CH— and —N— p and q are independently 0, 1 or 2, $R^4$ represents a hydrogen atom or a straight or branched $C_{1-4}$ alkyl group, and each $R^5$ independently represents a hydrogen atom or a methyl group In yet a more specific embodiment of the present invention $R^3$ represents a hydrogen atom or a group 1-tert-butylpiperidin-4-yl.

Particular individual compounds of the invention include:

4-(2,4-Difluorophenyl)-8-(2-methylphenyl)-1,7-naphthyridine 4-(2,4-Difluorophenyl)-8-(2-methoxyphenyl)-1,7-naphthyridine 4-[4-(2,4-Difluorophenyl)-1,7-naphthyridin-8-yl]-3-methylphenol 8-(1,3-Benzodioxol-4-yl)-4-(2,4-difluorophenyl)-1,7-naphthyridine 4-(2,4-Difluorophenyl)-8-(2,6-difluorophenyl)-1,7-naphthyridine 4-(2,4-Difluorophenyl)-8-[4-(2-methoxyethoxy)-2-methylphenyl]-1,7-naphthyridine 4-(2,4-Difluorophenyl)-8-[2-methyl-4-(2-morpholin-4-ylethoxy)phenyl]-1,7-naphthyridine 4-(2,4-Difluorophenyl)-8-(2,6-dimethylphenyl)-1,7-naphthyridine 4-(2,4-Difluorophenyl)-8-(2,6-dimethoxyphenyl)-1,7-naphthyridine 4-(2,4-Difluorophenyl)-8-(2-methylphenyl)-2-piperidin-4-yl-1,7-naphthyridine 8-(2-Chlorophenyl)-4-(2,4-difluorophenyl)-2-piperidin-4-yl-1,7-naphthyridine 4-(2,4-Difluorophenyl)-8-(2-fluorophenyl)-2-piperidin-4-yl-1,7-naphthyridine 4-(2,4-Difluorophenyl)-8-(2,6-difluorophenyl)-2-piperidin-4-yl-1,7-naphthyridine 8-(2,6-Dichlorophenyl)-4-(2,4-difluorophenyl)-2-piperidin-4-yl-1,7-naphthyridine 4-(2,4-Difluorophenyl)-8-(2-methylphenyl)-1,7-naphthyridine 7-oxide 4-(2,4-Difluorophenyl)-8-(2-methoxyphenyl)-1,7-naphthyridine 7-oxide 4-[4-(2,4-Difluorophenyl)-7-oxido-1,7-naphthyridin-8-yl]-3-methylphenol 8-(1,3-Benzodioxol-4-yl)-4-(2,4-difluorophenyl)-1,7-naphthyridine 7-oxide 4-(2,4-Difluorophenyl)-8-(2,6-difluorophenyl)-1,7-naphthyridine 7-oxide 4-(2,4-Difluorophenyl)-8-(2,6-dimethylphenyl)-1,7-naphthyridine 7-oxide 4-(2,4-Difluorophenyl)-8-(2,6-dimethoxyphenyl)-1,7-naphthyridine 7-oxide N-{4-[4-(2,4-Difluorophenyl)-7-oxido-1,7-naphthyridin-8-yl]-3-methylphenyl}methane-sulfonamide 8-(2-Chlorophenyl)-4-(2,4-difluorophenyl)-1,7-naphthyridine 7-oxide 4-(2,4-Difluorophenyl)-8-(2-fluorophenyl)-1,7-naphthyridine 7-oxide 8-(2,6-Dichlorophenyl)-4-(2,4-difluorophenyl)-1,7-naphthyridine 7-oxide 4-(2,4-Difluorophenyl)-8-(2-methylphenyl)-2-piperidin-4-yl-1,7-naphthyridine 7-oxide 8-(2-Chlorophenyl)-4-(2,4-difluorophenyl)-2-piperidin-4-yl-1,7-naphthyridine 7-oxide 4-(2,4-Difluorophenyl)-8-(2-fluorophenyl)-2-piperidin-4-yl-1,7-naphthyridine 7-oxide 4-(2,4-Difluorophenyl)-8-(2,6-difluorophenyl)-2-piperidin-4-yl-1,7-naphthyridine 7-oxide 8-(2,6-dichlorophenyl)-4-(2,4-difluorophenyl)-2-(piperidin-4-yl)-1,7-naphthyridine 7-oxide 4-(2,4-Difluorophenyl)-8-(2,6-difluorophenyl)-2-(1-methylpiperidin-4-yl)-1,7-naphthyridine 7-oxide 8-(2,6-Dichlorophenyl)-4-(2,4-difluorophenyl)-2-(1-methylpiperidin-4-yl)-1,7-naphthyridine 7-oxide 4-(2,4-Difluorophenyl)-8-(2,6-difluorophenyl)-2-(1-isopropylpiperidin-4-yl)-1,7-naphthyridine 7-oxide 8-(2,6-Dichlorophenyl)-4-(2,4-difluorophenyl)-2-(1-isopropylpiperidin-4-yl)-1,7-naphthyridine 7-oxide 2-(1-Tert-butylpiperidin-4-yl)-4-(2,4-difluorophenyl)-8-(2,6-difluorophenyl)-1,7-naphthyridine 7-oxide 2-(1-Tert-butylpiperidin-4-yl)-8-(2,6-dichlorophenyl)-4-(2,4-difluorophenyl)-1,7-naphthyridine 7-oxide 4-(2-Chloro-4-fluorophenyl)-8-(2,6-difluorophenyl)-2-piperidin-4-yl-1,7-naphthyridine 4-(2-Chloro-4-fluorophenyl)-8-(2,6-dichlorophenyl)-2-piperidin-4-yl-1,7-naphthyridine 4-(2-Chloro-4-fluorophenyl)-8-(2,6-difluorophenyl)-1,7-naphthyridine 7-oxide 4-(2-Chloro-4-fluorophenyl)-8-(2,6-dichlorophenyl)-1,7-naphthyridine 7-oxide 4-(2-Chloro-4-fluorophenyl)-8-(2-chlorophenyl)-2-piperidin-4-yl-1,7-naphthyridine 7-oxide 4-(2-Chloro-4-fluorophenyl)-8-(2,6-difluorophenyl)-2-piperidin-4-yl-1,7-naphthyridine 7-oxide 4-(2-Chloro-4-fluorophenyl)-8-(2,6-dichlorophenyl)-2-piperidin-4-yl-1,7-naphthyridine 7-oxide 4-(2-Chloro-4-fluorophenyl)-8-(2,6-difluorophenyl)-2-(1-methylpiperidin-4-yl)-1,7-naphthyridine 7-oxide 4-(2-Chloro-4-fluorophenyl)-8-(2,6-dichlorophenyl)-2-(1-methylpiperidin-4-yl)-1,7-naphthyridine 7-oxide 4-(2-Chloro-4-fluorophenyl)-8-(2,6-difluorophenyl)-2-(1-isopropylpiperidin-4-yl)-1,7-naphthyridine 7-oxide 4-(2-Chloro-4-fluorophenyl)-8-(2,6-dichlorophenyl)-2-(1-isopropylpiperidin-4-yl)-1,7-naphthyridine 7-oxide 2-(1-Tert-butylpiperidin-4-yl)-4-(2-chloro-4-fluorophenyl)-8-(2,6-difluorophenyl)-1,7-naphthyridine 7-oxide 2-(1-Tert-butylpiperidin-4-yl)-4-(2-chloro-4-fluorophenyl)-8-(2,6-dichlorophenyl)-1,7-naphthyridine 7-oxide 4-(2-Chlorophenyl)-8-(2,6-difluorophenyl)-2-piperidin-4-yl-1,7-naphthyridine 4-(2-Chlorophenyl)-8-(2,6-dichlorophenyl)-2-piperidin-4-yl-1,7-naphthyridine 4-(2-Chlorophenyl)-8-(2,6-difluorophenyl)-2-piperidin-4-yl-1,7-naphthyridine 7-oxide 4-(2-Chlorophenyl)-8-(2,6-dichlorophenyl)-2-piperidin-4-yl-1,7-naphthyridine 7-oxide 4-(2-Chlorophenyl)-8-(2,6-difluorophenyl)-2-(1-methylpiperidin-4-yl)-1,7-naphthyridine 7-oxide 4-(2-Chlorophenyl)-8-(2,6-dichlorophenyl)-2-(1-methylpiperidin-4-yl)-1,7-naphthyridine 7-oxide 4-(2-Chlorophenyl)-8-(2,6-difluorophenyl)-2-(1-isopropylpiperidin-4-yl)-1,7-naphthyridine 7-oxide 4-(2-Chlorophenyl)-8-(2,6-dichlorophenyl)-2-(1-isopropylpiperidin-4-yl)-1,7-naphthyridine 7-oxide 2-(1-Tert-butylpiperidin-4-yl)-4-(2-chlorophenyl)-8-(2,6-difluorophenyl)-1,7-naphthyridine 7-oxide 2-(1-Tert-butylpiperidin-4-yl)-4-(2-chlorophenyl)-8-(2,6-dichlorophenyl)-1,7-naphthyridine 7-oxide 8-(2,6-Difluorophenyl)-4-(2-methoxyphenyl)-1,7-naphthyridine 8-(2,6-Dimethylphenyl)-4-(2-methoxyphenyl)-1,7-naphthyridine N-{4-[4-(2-methoxyphenyl)-1,7-naphthyridin-8-yl]-3-methylphenyl}methanesulfonamide 8-(2,6-Difluorophenyl)-4-(2-methoxyphenyl)-1,7-naphthyridine 7-oxide 8-(2,6-Dimethylphenyl)-4-(2-methoxyphenyl)-1,7-naphthyridine 7-oxide N-{4-[4-(2-methoxyphenyl)-7-oxido-1,7-naphthyridin-8-yl]-3-methylphenyl}methane-sulfonamide 8-(2-Chlorophenyl)-4-(2-methoxyphenyl)-1,7-naphthyridine 7-oxide 4,8-Bis(2-methoxyphenyl)-1,7-naphthyridine 7-oxide 8-(2-Methoxyphenyl)-4-[3-(trifluoromethyl)phenyl]-1,7-naphthyridine 7-oxide 8-(2,6-Difluorophenyl)-4-[3-(trifluoromethyl)phenyl]-1,7-naphthyridine 7-oxide 8-(2,6-Dichlorophenyl)-4-[3-(trifluoromethyl)phenyl]-1,7-naphthyridine 7-oxide 8-(2-Methoxyphenyl)-4-[3-(trifluoromethyl)phenyl]-2-piperidin-4-yl-1,7-naphthyridine 7-oxide 8-(2,6-Difluorophenyl)-4-[3-(trifluoromethyl)phenyl]-2-piperidin-4-yl-1,7-naphthyridine 7-oxide 8-(2,6-Dichlorophenyl)-4-[3-(trifluoromethyl)phenyl]-2-piperidin-4-yl-1,7-naphthyridine 7-oxide 8-(2,6-Difluorophenyl)-4-[4-(trifluoromethyl)phenyl]-1,7-naphthyridine 7-oxide 8-(2,6-dichlorophenyl)-4-[4-(trifluoromethyl)phenyl]-1,7-naphthyridine 7-oxide 8-(2,6-difluorophenyl)-4-[4-(trifluoromethyl)phenyl]-2-piperidin-4-yl-1,7-naphthyridine 7-oxide 8-(2,6-Dichlorophenyl)-4-[4-(trifluoromethyl)phenyl]-2-piperidin-4-yl-1,7-naphthyridine 7-oxide 8-(2,6-Dichlorophenyl)-4-(2,4-difluorophenyl)-N-piperidin-4-yl-1,7-naphthyridin-2-amine 4-(2,4-Difluorophenyl)-8-(2,6-difluorophenyl)-N-piperidin-4-yl-1,7-naphthyridin-2-amine 8-(2-Chlorophenyl)-4-(2,4-difluorophenyl)-N-piperidin-4-yl-1,7-naphthyridin-2-amine
4-(2,4-Difluorophenyl)-8-(2-methylphenyl)-N-piperidin-4-yl-1,7-naphthyridin-2-amine
8-(2,6-Dichlorophenyl)-4-(2,4-difluorophenyl)-2-piperazin-1-yl-1,7-naphthyridine
4-(2,4-Difluorophenyl)-8-(2,6-difluorophenyl)-2-piperazin-1-yl-1,7-naphthyridine
8-(2-chlorophenyl)-4-(2,4-difluorophenyl)-2-piperazin-1-yl-1,7-naphthyridine
4-(2,4-difluorophenyl)-8-(2-methylphenyl)-2-piperazin-1-yl-1,7-naphthyridine
8-(2,6-Dichlorophenyl)-4-(2,4-difluorophenyl)-N-piperidin-4-yl-1,7-naphthyridin-2-amine 7-oxide
4-(2,4-Difluorophenyl)-8-(2,6-difluorophenyl)-N-piperidin-4-yl-1,7-naphthyridin-2-amine 7-oxide
8-(2-Chlorophenyl)-4-(2,4-difluorophenyl)-N-piperidin-4-yl-1,7-naphthyridin-2-amine 7-oxide
4-(2,4-Difluorophenyl)-8-(2-methylphenyl)-N-piperidin-4-yl-1,7-naphthyridin-2-amine 7-oxide
8-(2,6-Dichlorophenyl)-4-(2,4-difluorophenyl)-2-piperazin-1-yl-1,7-naphthyridine 7-oxide
4-(2,4-Difluorophenyl)-8-(2,6-difluorophenyl)-2-piperazin-1-yl-1,7-naphthyridine 7-oxide
8-(2-Chlorophenyl)-4-(2,4-difluorophenyl)-2-piperazin-1-yl-1,7-naphthyridine 7-oxide
4-(2,4-Difluorophenyl)-8-(2-methylphenyl)-2-piperazin-1-yl-1,7-naphthyridine 7-oxide
8-(2,6-Dichlorophenyl)-4-(2,4-difluorophenyl)-N-(1,2,2,6,6-pentamethylpiperidin-4-yl)-1,7-naphthyridin-2-amine 7-oxide
8-(2,6-Dichlorophenyl)-4-(2,4-difluorophenyl)-2-(piperidin-4-yloxy)-1,7-naphthyridine 7-oxide
4-(2,4-Difluorophenyl)-8-(2,6-difluorophenyl)-2-(piperidin-4-yloxy)-1,7-naphthyridine 7-oxide
Of outstanding interest are:
4-(2,4-Difluorophenyl)-8-(2,6-difluorophenyl)-1,7-naphthyridine 7-oxide
8-(2,6-Dichlorophenyl)-4-(2,4-difluorophenyl)-1,7-naphthyridine 7-oxide
4-(2,4-Difluorophenyl)-8-(2,6-difluorophenyl)-2-piperidin-4-yl-1,7-naphthyridine 7-oxide
8-(2,6-dichlorophenyl)-4-(2,4-difluorophenyl)-2-(piperidin-4-yl)-1,7-naphthyridine 7-oxide
2-(1-Tert-butylpiperidin-4-yl)-4-(2,4-difluorophenyl)-8-(2,6-difluorophenyl)-1,7-naphthyridine 7-oxide
2-(1-Tert-butylpiperidin-4-yl)-8-(2,6-dichlorophenyl)-4-(2,4-difluorophenyl)-1,7-naphthyridine 7-oxide
4-(2-Chloro-4-fluorophenyl)-8-(2,6-difluorophenyl)-1,7-naphthyridine 7-oxide
4-(2-Chloro-4-fluorophenyl)-8-(2,6-dichlorophenyl)-1,7-naphthyridine 7-oxide
4-(2-Chloro-4-fluorophenyl)-8-(2,6-difluorophenyl)-2-piperidin-4-yl-1,7-naphthyridine 7-oxide
4-(2-Chloro-4-fluorophenyl)-8-(2,6-dichlorophenyl)-2-piperidin-4-yl-1,7-naphthyridine 7-oxide
2-(1-Tert-butylpiperidin-4-yl)-4-(2-chloro-4-fluorophenyl)-8-(2,6-difluorophenyl)-1,7-naphthyridine 7-oxide
2-(1-Tert-butylpiperidin-4-yl)-4-(2-chloro-4-fluorophenyl)-8-(2,6-dichlorophenyl)-1,7-naphthyridine 7-oxide
4-(2-Chlorophenyl)-8-(2,6-difluorophenyl)-2-piperidin-4-yl-1,7-naphthyridine 7-oxide
4-(2-Chlorophenyl)-8-(2,6-dichlorophenyl)-2-piperidin-4-yl-1,7-naphthyridine 7-oxide
2-(1-Tert-butylpiperidin-4-yl)-4-(2-chlorophenyl)-8-(2,6-difluorophenyl)-1,7-naphthyridine 7-oxide
2-(1-Tert-butylpiperidin-4-yl)-4-(2-chlorophenyl)-8-(2,6-dichlorophenyl)-1,7-naphthyridine 7-oxide
8-(2,6-Dichlorophenyl)-4-(2,4-difluorophenyl)-N-piperidin-4-yl-1,7-naphthyridin-2-amine 7-oxide
4-(2,4-Difluorophenyl)-8-(2,6-difluorophenyl)-N-piperidin-4-yl-1,7-naphthyridin-2-amine 7-oxide
8-(2,6-Dichlorophenyl)-4-(2,4-difluorophenyl)-2-piperazin-1-yl-1,7-naphthyridine 7-oxide
4-(2,4-Difluorophenyl)-8-(2,6-difluorophenyl)-2-piperazin-1-yl-1,7-naphthyridine 7-oxide
4-(2,4-Difluorophenyl)-8-(2-methylphenyl)-2-piperazin-1-yl-1,7-naphthyridine 7-oxide
4-(2,4-Difluorophenyl)-8-(2,6-difluorophenyl)-2-(piperidin-4-yloxy)-1,7-naphthyridine 7-oxide According to a further feature of the present invention, compounds of general formula (I) wherein $R^3$ is a hydrogen atom are prepared following the synthetic scheme illustrated in Figure 1.

FIGURE 1

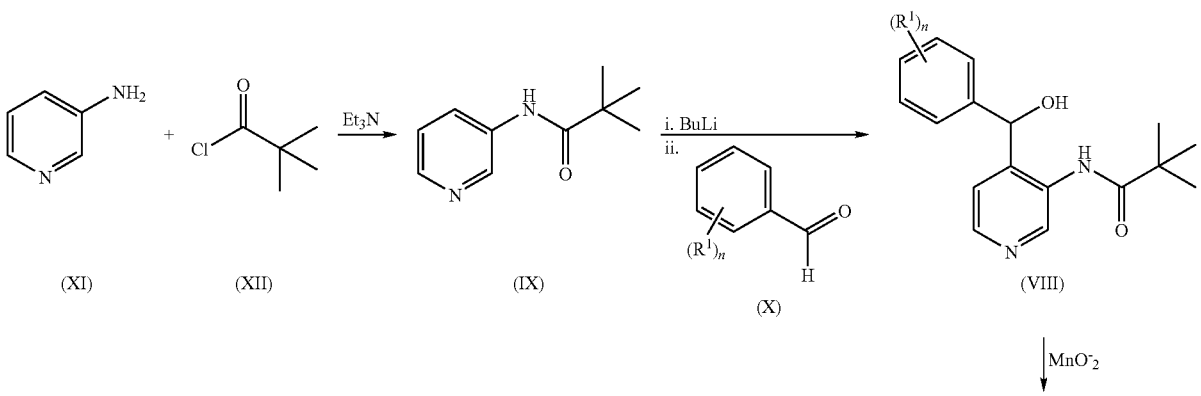

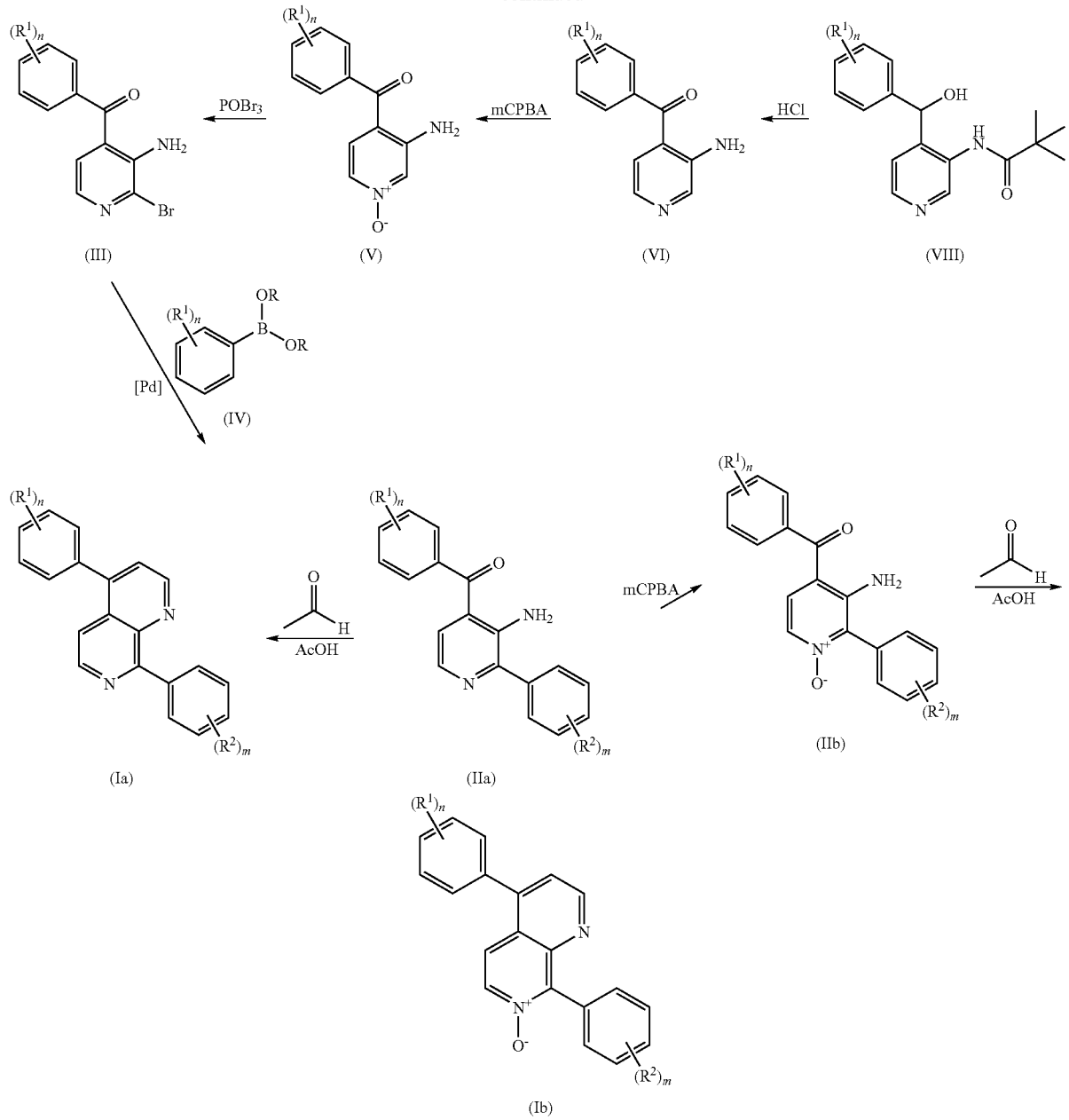

Reaction of 3-aminopyridine (XI) with an acyl chloride (XII) such as pivaloyl chloride in the presence of a base such as triethylamine, or diisopropylethylamine, using an halogenated solvent such as dichloromethane or an ether solvent such as dioxane at a temperature from 0° C. to 110° C. yields compound (IX).

Compounds of formula (VIII) can be obtained by lithiation of the compounds of formula (IX) with a solution of BuLi in hexanes, possibly in the presence of a cosolvent such as N,N,N',N'-tetramethylethane-1,2-diamine and subsequent addition of the corresponding aldehydes of formula (X) at a temperature from −78° C. to room temperature.

Oxidation of the alcohol compound (VIII) with an oxidizing agent such as manganese dioxide, Dess-Martin periodinane, tetrapropyl-ammonium perruthenate or pyridinium chlorochromate, preferably with manganese dioxide in an halogenated solvent such as chloroform at a temperature from room temperature to the boiling point of the solvent yields the compounds of formula (VII).

Subsequent hydrolysis of the pivalamide group in compounds of formula (VII) in acidic conditions such as treatment with HCl 5N using a solvent miscible with water such as ethanol at a temperature from 100° C. to 150° C. yields the aminopyridine of formula (VI).

Subsequent oxidation of the aminopyridine of formula (VI) with an oxidizing agent such as Oxone®, magnesium monoperoxyphthalate hexahydrate, hydrogen peroxide or meta-chloroperbenzoic acid, preferably with meta-chloroperbenzoic in an halogenated solvent such as dichloromethane and a temperature from 0° C. to the boiling point of the solvent, yields the pyridine N-oxide of formula (V).

The intermediate of formula (III) may be obtained by reacting the pyridine N-oxide of formula (V) with phosphorus oxybromide neat or in an halogenated solvent such as dichloromethane at a temperature from 60° C. to 140° C.

The compounds of formula (IIa) may be obtained by coupling a bromoderivative of formula (III) with the corresponding boronic acids or boronates of formula (IV) using Suzuki reactions (Miyaura, N.; Suzuki, A. *Chem. Rev.* 1995, 95, 2457). These reactions may be catalyzed by a palladium catalyst such as [1,1'-bis(diphenylphosphino)-ferrocene]dichloropalladium(II) complex with dichloromethane (1:1), tetrakis (triphenylphosphine)-palladium(0), bis(triphenylphosphine) palladium(II) chloride or tris(dibenzylideneacetone)-dipalladium(0) in an aprotic organic solvent such as dioxane, toluene, DMF or 1,2-dimethoxyethane and in the presence of a base such as cesium carbonate, sodium carbonate or potassium phosphate at a temperature from 80° C. to 140° C.

The nitrogen atom of the pyridine ring in the compounds of formula (IIa) may, when the groups $R^1$ and $R^2$ are selected from alkyl groups, alkoxy groups, hydroxy groups, halogens, carboxylic acid groups, amide groups not containing aminoalkyl chains, be oxidised with an oxidizing agent such as Oxone®, magnesium monoperoxyphthalate hexahydrate, hydrogen peroxide or meta-chloroperbenzoic acid, preferably with meta-chloroperbenzoic acid in an halogenated solvent such as dichloromethane, at a temperature from 0° C. to the boiling point of the solvent to yield the pyridine oxides of formula (IIb).

In the particular case where m is 2 and the groups $R^2$ are both in the ortho position and selected from alkyl groups, alkoxy groups or halogens the bromoderivative of formula (III) may be coupled with the corresponding boronic acid or boronate by a Suzuki reaction (Miyaura, N.; Suzuki, A. *Chem. Rev.* 1995, 95, 2457) using a palladium catalyst such as tris(dibenzylideneacetone)dipalladium(0) in the presence of a ligand such as 2-(dicyclohexylphosphino)-2',6'-dimethoxy-1-1'-biphenyl (S-PHOS) and a base such as potassium phosphate, and in a solvent such as toluene at a temperature from 80° C. to 140° C. to yield the compound of formula (IIa).

In the particular case where m is 2 and the two $R^2$ groups are fluor atoms, the bromoderivative (III) may be coupled with the corresponding 1,3-difluorobenzene by a Negishi reaction (Negishi, E.-I; Baba, S. *J. Chem. Soc., Chem Commun.* 1976, 596) to yield the compound (IIa). In this reaction, the first step is the lithiation of 1,3-difluorobenzene by treatment with a base such as BuLi at –78° C. using THF as solvent, afterwards a transmetalation step is carried out by treatment of the corresponding organolithium derivative with zinc dichloride at –50° C. and finally, the resulting organozinc is coupled with the bromoderivative of formula (III) using a palladium catalyst such as tetrakis(triphenylphosphine)palladium(0), bis(triphenylphosphine)-palladium(II) chloride or tris(dibenzylideneacetone)dipalladium(0) at a temperature between room temperature and the boiling point of the solvent.

The compounds of formula (Ia) and (Ib) may advantageously be obtained by an modified acid-catalyzed Friedländer cyclisation (Cheng, C. C.; Yan, S. J. *Org. Recat.* 1982, 28, 37) of the corresponding 3-amino-4-oxo-pyridine (IIa) or its N-oxide (IIb) and acetaldehyde in acetic acid as solvent at a temperature from 80° C. to 140° C. in a sealed vessel under microwave irradiation.

In the particular case where $R^3$ is a group of formula -L-$G^1$ wherein L represents a direct bond and $G^1$ represents a piperidinyl group, unsubstituted or substituted with akyl groups, the synthetic scheme of Figure 2 shown below may be used.

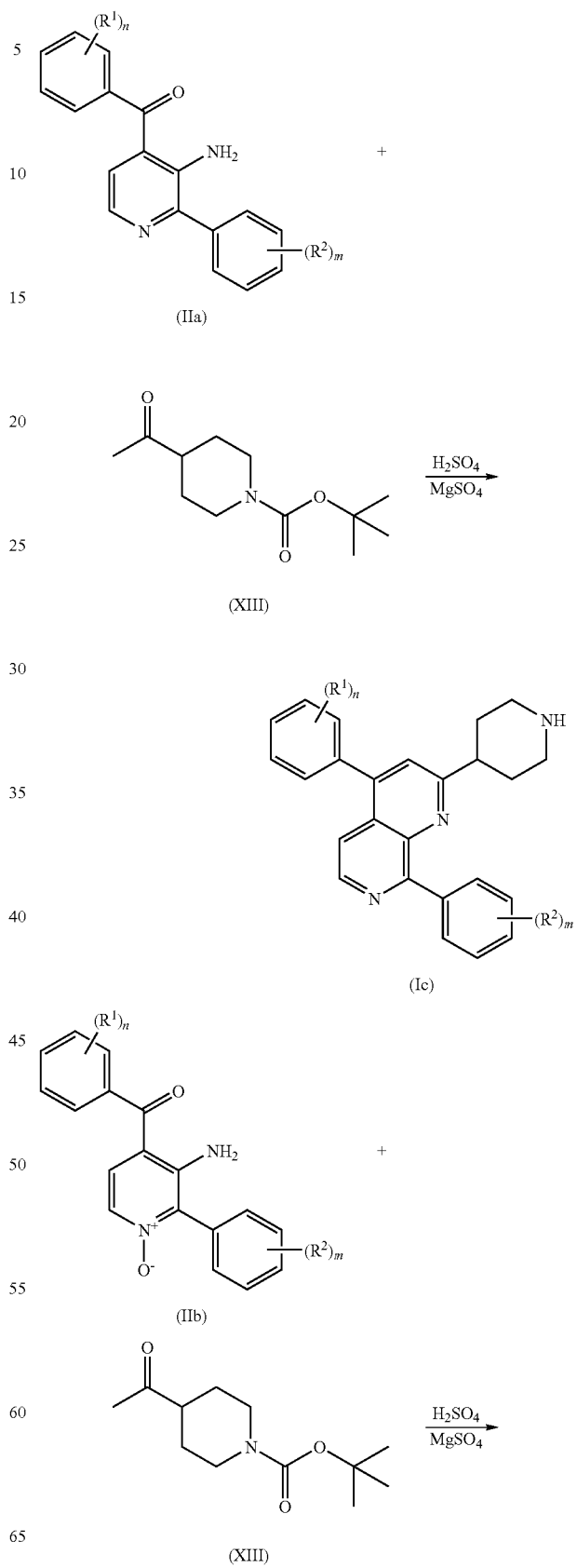

FIGURE 2

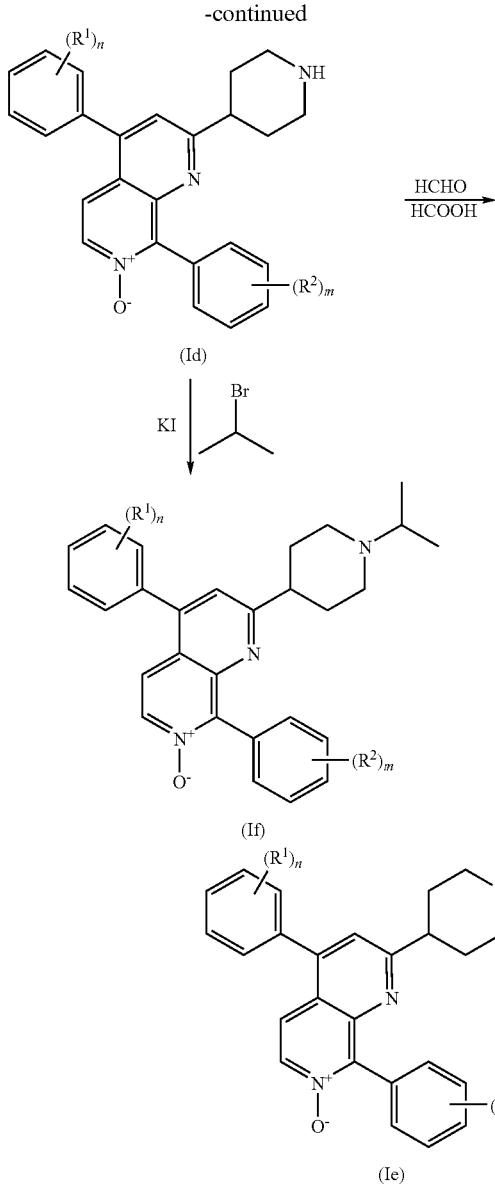

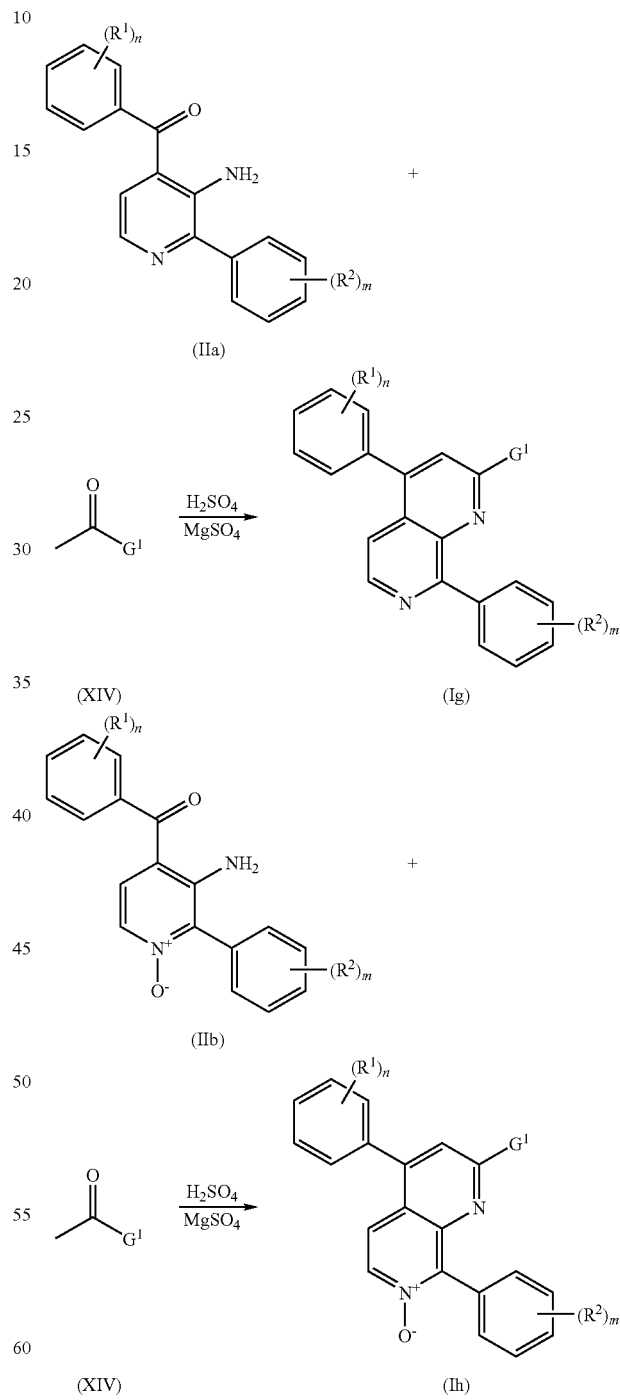

cesium carbonate, potassium carbonate, sodium carbonate or potassium phosphate at a temperature from room temperature to 140° C.

In the particular case where L is a direct bond and $G^1$ is a non-aromatic heterocyclic ring, the synthetic scheme of Figure 3 shown below may be used.

FIGURE 3

The compounds of formula (IIa) and (IIb) are reacted with the methyl ketone of formula (XIII) in the presence of a strong acid such as hydrochloric acid, sulfuric acid or perchloric acid in an aprotic organic solvent such as toluene or xilenes in the presence of a drying agent such as anhydrous magnesium sulphate or sodium sulphate at a temperature from 80° C. to 140° C. to yield, respectively, the compounds of formula (Ic) and (Id).

Compound (Ie) may be obtained by reaction of (Id) with methylating agents such as methyl iodide or methyl sulphate in an organic solvent such as acetone or ethyl methyl ketone at a temperature from room temperature to 140° C. Compound (Ie) may be also obtained from the corresponding piperidine derivative (Id) using formaldehyde in a solvent such as formic acid at a temperature from room temperature to 140° C.

Compound (If) may be obtained by reaction of (Id) with alkylating agents such as 2-bromopropane or 2-iodopropane in an aprotic organic solvent such as dioxane, toluene, DMF or 1,2-dimethoxyethane and in the presence of a base such as 3-Amino-4-oxo-pyridine (IIa) or its N-oxide (IIb) may be reacted with the methyl ketone of formula (XIV) in the presence of a strong acid such as hydrochloric acid, sulfuric acid or perchloric acid in an aprotic organic solvent such as toluene or xylenes in the presence of a drying agent such as anhydrous magnesium sulphate or sodium sulphate at a temperature from 80° C. to 140° C. to yield, respectively, the compounds of formula (Ig) and (Ih).

The present invention also provides a process, following the synthetic scheme illustrated in Figure 4, for the preparation of compounds of formula (I) wherein either (a) L is selected from the group consisting of —O—, —S— and —NH—, (b) L is a direct bond and $G^1$ comprises a basic heteroatom attached to the linker L, such as 4-aminopiperidine, 4-hydroxypiperidine, piperazine, homopiperazine, morpholine, N,N-dimethylethylendiamine, 3-aminopyrrolidine and the like or (c) L is a direct bond and $G^1$ is an aromatic heterocycle.

FIGURE 4

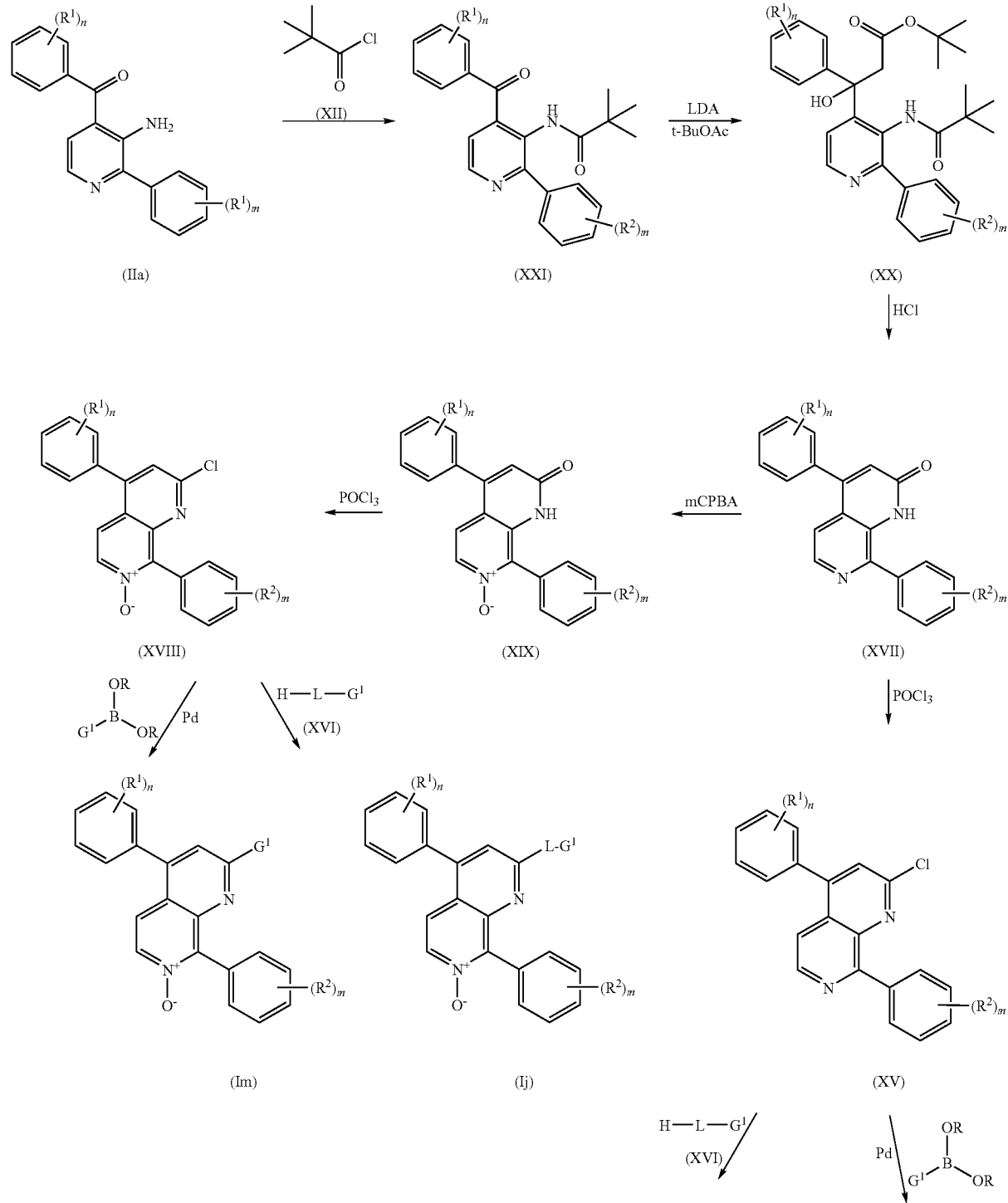

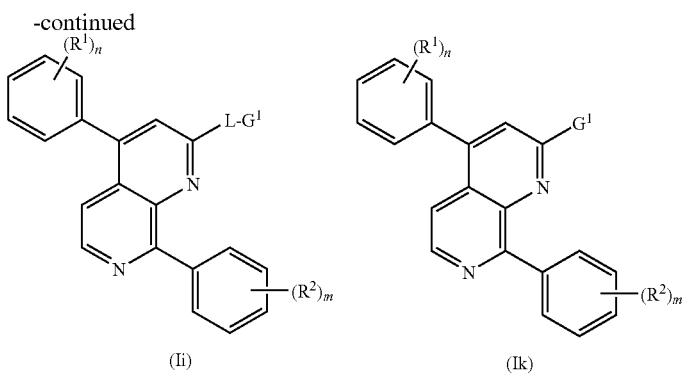

Reaction of 3-aminopyridine (IIa) with an acyl chloride (XII) such as pivaloyl chloride in the presence of a base such as triethylamine, or diisopropylethylamine, using an halogenated solvent such as dichloromethane or an ether solvent such as dioxane at a temperature from 0° C. to 110° C. yields compound (XXI).

Compounds of formula (XX) can be obtained by addition of the lithium enolate of an alkyl acetate such as tert-butyl acetate to intermediate compound (XXI) in a solvent such as THF at a temperature between −78° C. and room temperature. Lithium enolates can be obtained by procedures well known in the literature using a base such as LDA.

Reaction of compounds (XX) with organic or inorganic acids such as HCl 3M at a temperature between room temperature and 150° C. gave naphthyridones (XVII) after the intramolecular cyclization reaction.

The treatment of naphthyridones (XVII) with a halogenating reagent such as phosphorus oxychloride neat or in a halogenated solvent at a temperature between room temperature and 150° C. afforded chloronaphthyridines (XV).

When either (a) L is selected from the group consisting of —O—, —S— and —NH—, (b) L is a direct bond and $G^1$ comprises a basic heteroatom attached to the linker L, such as 4-aminopiperidine, 4-hydroxypiperidine, piperazine, homopiperazine, morpholine, N,N-dimethylethylendiamine, 3-aminopyrrolidine and the like, the reaction of compounds (XV) with compounds of formula (XVI) in protic solvents such as 2-ethoxyethanol or in aprotic solvents such as toluene, in the presence or not of a base such as diisopropylethylamine, triethylamine, cesium carbonate, potassium carbonate, sodium carbonate or potassium phosphate at a temperature between room temperature and 160° C. gave naphthyridines (Ii)

When L is a direct bond and $G^1$ is an aromatic heterocycle, the chloronaphthyridines (XV) may be coupled with the corresponding boronic acid or boronate by Suzuki reaction (Miyaura, N.; Suzuki, A. Chem Rev. 1995, 95, 2457) to yield the compounds of formula (Ik). These reactions may be catalized by a palladium catalyst like [1,1′-bis(diphenyl-phosphino)-ferrocene]dichloropalladium(II) complex with dichloromethane (1:1), tetrakis-(triphenylphosphine)-palladium(0), bis(triphenylphosphine)palladium(II) chloride or tris(dibenzylideneacetone)-dipalladium(0) in an aprotic organic solvent such as dioxane, toluene, DMF or 1,2-dimethoxyethane and in the presence of a base such as cesium carbonate, sodium carbonate or potassium phosphate at a temperature from 80° C. to 140° C.

On the other hand, it is possible to react naphthyridinone (XVII) with an oxidizing agent such as Oxone®, magnesium monoperoxyphthalate hexahydrate, hydrogen peroxide or meta-chloroperbenzoic acid, preferably with meta-chloroperbenzoic acid in a halogenated solvent such as dichloromethane and a temperature from 0° C. to the boiling point of the solvent, in order to obtain compounds of formula (XIX).

The treatment of naphthyridones (XIX) with an halogenating reagent such as phosphorus oxychloride neat or in an halogenated solvent at a temperature between room temperature and 150° C. afforded compounds of formula (XVIII).

When either (a) L is selected from the group consisting of —O—, —S— and —NH—, (b) L is a direct bond and $G^1$ comprises a basic heteroatom attached to the linker L, such as 4-aminopiperidine, 4-hydroxypiperidine, piperazine, homopiperazine, morpholine, N,N-dimethylethylendiamine, 3-aminopyrrolidine and the like, the reaction of compounds (XVIII) with compounds of formula (XVI) in protic solvents such as 2-ethoxyethanol or in aprotic solvents such as toluene, in the presence or not of a base such as diisopropylethylamine, triethylamine, cesium carbonate, potassium carbonate, sodium carbonate or potassium phosphate at a temperature between room temperature and 160° C. gave naphthyridines N-oxide (Ij).

When L is a direct bond and $G^1$ is an aromatic heterocycle, the chloronaphthyridine N-oxides (XVIII) may be coupled with the corresponding boronic acid or boronate by Suzuki reaction (Miyaura, N.; Suzuki, A. Chem Rev. 1995, 95, 2457) to yield the compounds of formula (Im). These reactions may be catalyzed by a palladium catalyst like [1,1′-bis(diphenylphosphino)-ferrocene]dichloropalladium(II) complex with dichloromethane (1:1), tetrakis-(triphenylphosphine)-palladium(0), bis(triphenylphosphine)palladium(II) chloride or tris(dibenzylideneacetone)-dipalladium(0) in an aprotic organic solvent such as dioxane, toluene, DMF or 1,2-dimethoxyethane and in the presence of a base such as cesium carbonate, sodium carbonate or potassium phosphate at a temperature from 80° C. to 140° C.

The intermediate methyl ketone (XIII) may be obtained by following the synthetic scheme of Figure 5 shown below.

FIGURE 5

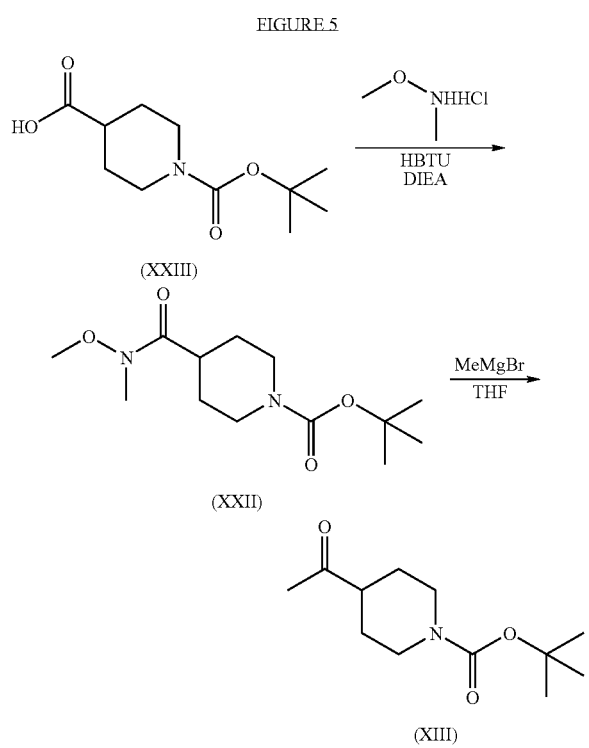

The acid compound of formula (XXIII) is reacted with N,O-dimethylhydroxylamine hydrochloride in the presence of an amidation reagent such as 2-benzotriazol-1-yl-N,N,N',N'-tetramethyluronium hexafluorphosphate (HBTU), 2-benzotriazol-1-yl-N,N,N',N'-tetramethyluronium tetrafluoroborate (TBTU) or 1-(3-dimethylaminopropyl)-3-ethylcarbodiimide hydrochloride (EDC) and an organic base such as diisopropylethylamine or triethylamine in an aprotic organic solvent such as DMF or acetonitrile at room temperature to yield the compound of formula (XXII).

The intermediate of formula (XIII) may be obtained by reacting the amide of formula (XXII) with organometallic reagents such as methyl magnesium chloride, methyl magnesium bromide or methyl lithium in an inert solvent such as dichloromethane, diethyl ether or tetrahydrofuran, at a temperature from −20° C. to the boiling point of the solvent.

The intermediate methyl ketone (XIV) may be obtained by following the synthetic scheme of Figure 6 shown below which illustrates the synthetic path in the particular case wherein $G^1$ is a tert-butylpiperidine group,

FIGURE 6

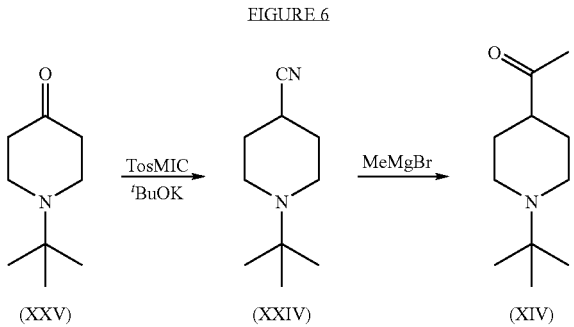

Compound (XXIV) may be obtained by reaction of the intermediate (XXV) (Amato, J. S.; Chung, J. Y. L.; Cvetovich, R. J.; Gong, X.; McLaughlin, M. and Reamer, R. A. *J. Org. Chem.* 2005, 70, 1930) with p-toluenesulfonylmethyl isocyanide (TOSMIC) in an aprotic organic solvent such as dioxane, toluene, DMF or 1,2-dimethoxyethane and in the presence of a base such as potassium Pert-butoxide or sodium ethoxide at a temperature from 0° C. to to the boiling point of the solvent.

The intermediate of formula (XIV) may be obtained by reacting the nitrile of formula (XXIV) with organometallic reagents such as methyl magnesium chloride, methyl magnesium bromide or methyl lithium in an inert solvent such as dichloromethane, diethyl ether or THF, at a temperature from −20° C. to the boiling point of the solvent.

The 1,7-naphthyridine derivatives of formula (I) can be converted by methods known per se into pharmaceutically acceptable salts or N-oxides. Preferred salts are acid addition salts obtainable by treatment with organic or inorganic acids such as fumaric, tartaric, succinic or hydrochloric acid.

Biological Testing
Inhibition Assay

Enzymatic activity assay was performed in 96-well microtiter plates (Corning, catalog number #3686) using a total volume of 50 µl of an assay buffer composed of 50 mM HEPES pH 7.5, 10 mM $MgCl_2$, 1.75 mM $Na_3VO_4$.

Various concentrations of the test compound or vehicle controls were pre-incubated for one hour with 0.055 µg/ml of the human p38alfa (SAPKa) enzyme (obtained from University of Dundee). The reaction started by addition of biotinylated ATF2 substrate and ATP in concentrations around their Km values (final concentration 0.62 µM and 60 µM respectively) and took place for one hour at 25° C. Addition of the detection reagents, streptavidin—XL665 and anti-phospho-residue antibody coupled to Europium cryptate, caused the juxtaposition of the cryptate and the XL665 fluorophore, resulting in fluorescence energy transfer (FRET). The FRET intensity depends on the amount of bounded cryptate antibody, which is proportional to the extent of substrate phosphorylation. FRET intensity was measured using Victor 2V spectrofluorometer. Data were analyzed by non-linear regression (Hill equation) to generate a dose-response curve. The calculated $IC_{50}$ value is the concentration of the test compound that caused a 50% decrease in the maximal FRET intensity.

Functional Assay

The activity of compounds in inhibiting TNFα production was measured in a cellular assay using the human monocytic cell line THP-1. For this purpose, $2 \times 10^5$ cells/well were plated in tissue-culture treated round-bottom 96-well plates in RPMI (containing 10% FCS, L-Gln 2 mM, Hepes buffer 10 mM, sodium pyruvate 1 mM, glucose 4.5 gr/L, $HNaCO_3$ 1.5 g/L and beta-mercaptoethanol 50 µM), together with compounds at the desired test concentration and LPS (Sigma, L2630) at a final 10 µg/ml concentration. Compounds were resuspended in 100% DMSO at a concentration of 1 mM and titrated thereof in 10× dilutions in medium. Controls included stimulated cells alone and stimulated cells treated with the highest concentration of compound vehicle (1% DMSO). Cells were incubated for 5 h at 37° C. in a 5% $CO_2$ atmosphere. Cell supernatant was recovered by centrifugation and diluted 5-fold prior to testing in a standard human TNFα ELISA (RnD systems).

Data were analyzed by non-linear regression (Hill equation) to generate a dose-response curve. The calculated $IC_{50}$ value is the concentration of the test compound that caused a 50% decrease in the maximal TNFα production.

Table 1 shows the activities in THP-1 assay of some compounds of the present invention.

TABLE 1

| Example | p38α IC$_{50}$ (nM) | THP-1 TNFα IC$_{50}$ (nM) |
|---|---|---|
| 19 | 57 | 223 |
| 25 | 28 | 14 |
| 29 | 0.90 | 2.45 |
| 30 | 1.5 | 1.6 |
| 35 | 2.8 | 3.4 |
| 36 | 1.2 | 1.6 |
| 39 | 87 | 63 |
| 40 | 14 | 43.5 |
| 43 | 0.40 | 2.9 |
| 48 | 1.6 | 3 |
| 49 | 0.55 | 0.46 |
| 52 | 0.27 | 4.2 |
| 53 | 0.34 | 0.53 |
| 59 | 0.41 | 0.1 |
| 86 | 0.37 | 0.9 |
| 87 | 0.29 | 1.9 |
| 90 | 1.1 | 0.8 |
| 91 | 0.63 | 4.1 |
| 95 | 0.92 | 0.2 |
| 96 | 0.22 | 3.2 |

It can be seen from Table 1 that the compounds of formula (I) are potent inhibitors of the p38 mitogen-activated protein kinase. Preferred naphthyridine derivatives of the invention possess an IC$_{50}$ value of inhibition of p38α of less than 1 μM, preferably less than 100 nM, more preferably less than 10 nM and most preferably less than 1 nM.

It can also be seen from Table 1 that the compounds of formula (I) are potent inhibitors of the TNFα production. Preferred naphthyridine derivatives of the invention possess an IC$_{50}$ value of inhibition of TNFα production of less than 1 μM, preferably less than 100 nM, more preferably less than 10 nM and most preferably less than 1 nM.

The naphthyridine derivatives of the invention are useful in the treatment or prevention of diseases known to be susceptible to improvement by inhibition of the p38 mitogen-activated protein kinase. Such diseases are, for example rheumatoid arthritis, ischemia-reperfusion injury, cerebral focal ischemia, acute coronary syndrome, COPD, Crohn's disease, irritable bowie syndrome, adult respiratory distress syndrome, osteoporosis Alzheimer's disease, rheumatoid spondylitis, psoriasis, atherosclerosis, osteoarthritis or multiple myeloma.

Accordingly, the naphthyridine derivatives of the invention and pharmaceutically acceptable salts thereof, and pharmaceutical compositions comprising such compound and/or salts thereof, may be used in a method of treatment of disorders of the human body which comprises administering to a subject requiring such treatment an effective amount of pyridin-3-amine derivative of the invention or a pharmaceutically acceptable salt thereof.

When the naphthyridine derivatives of the invention are used for the treatment of respiratory diseases such as asthma, chronic obstructive pulmonary disorder, pulmonary fibrosis or emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) leukotriene D4 antagonists, (6) inhibitors of egfr-kinase, (7) antagonists of the A2B adenosine receptor, (8) NK1 receptor agonists, (9) CRTh2 antagonists, (10) syk kinase inhibitors, (11) CCR3 antagonists and (12) VLA-4 antagonists.

Thus, the present invention also provides pharmaceutical compositions comprising a naphthyridine derivatives of the invention and another active compound selected from the groups consisting of (1) antagonists of M3 muscarinic receptors, (2) β2-agonists, (3) PDE 4 inhibitors, (4) cortiocosteroids, (5) leukotriene D4 antagonists, (6) inhibitors of egfr-kinase, (7) antagonists of the A2B adenosine receptor, (8) NK1 receptor agonists, (9) CRTh2 antagonists, (10) syk kinase inhibitors, (11) CCR3 antagonists and (12) VLA-4 antagonists.

The present invention also provides pharmaceutical compositions which comprise, as an active ingredient, at least a naphthyridine derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The syntheses of the compounds of the invention and of the intermediates for use therein are illustrated by the following Examples (1 to 96) including Preparation Examples (Preparations 1-56) which do not limit the scope of the invention in any way.

[1]H Nuclear Magnetic Resonance Spectra were recorded on a Varian Gemini 300 spectrometer. Melting points were recorded using a Büchi B-540 apparatus. The chromatographic separations were obtained using a Waters 2795 system equipped with a Symmetry C18 (2.1×100 mm, 3.5 mm) column. As detectors a Micromass ZMD mass spectrometer

PREPARATIONS

Preparation 1

[3-Amino-2-(2-methylphenyl)pyridin-4-yl](2,4-difluorophenyl)methanone a) 2,2-Dimethyl-N-pyridin-3-ylpropanamide To an ice-cooled solution of 3-aminopyridine (6 g, 63.8 mmol) and triethylamine (9.72 mL, 70.2 mmol) in 124 mL of dichloromethane under argon, was carefully added pivaloyl chloride (7.92 mL, 64.4 mmol) in 16 mL of dichloromethane. After the addition was completed, the reaction mixture was stirred at 0° C. for 15 minutes and at room temperature for 18 hours. The mixture was washed with water, aqueous 4% sodium bicarbonate, brine, dried over sodium sulphate and the solvent removed under reduced pressure. The residue was purified by column chromatography on silica flash, using hexane/ethyl acetate (85:15) as eluents, to yield the title compound (8.5 g, 75%) as a white solid.

b) N-{4-[(2,4-Difluorophenyl)(hydroxy)methyl]pyridin-3-yl}-2,2-dimethylpropanamide nBuLi (2.5M in hexanes, 56 mL, 140 mmol) was dropwise added to a solution of the title compound of Preparation 1a (10 g, 56.2 mmol) in dry THF (140 mL) at −78° C. under argon and the resulting mixture was stirred at that temperature for 15 minutes and at 0° C. for 3 hours. Then, the reaction mixture was cooled down to −78° C. and benzaldehyde (11.9 g, 84 mmol) in 14 mL of tetrahydrofuran was carefully added. After 15 minutes, the cooling bath was removed and the mixture stirred overnight at room temperature. Subsequently, the mixture was poured into water (600 mL) and it was extracted with ethyl acetate (3×300 mL). The organic solution was washed with brine, dried over anhydrous sodium sulphate and the solvent removed under reduced pressure. The residue was purified by column chromatography on silica flash, using n-hexane/ethyl acetate (1:4 to ethyl acetate) as eluents, to yield the title compound (9.5 g, 53%) as a white solid.

c) N-[4-(2,4-Difluorobenzoyl)pyridin-3-yl]-2,2-dimethylpropanamide

The title compound of Preparation 1b (20.1 g, 62.81 mmol) was dissolved in chloroform (550 mL) and activated manganese (IV) oxide (54.8 g, 628.1 mmol) was portionwise added during 1 hour. The suspension was stirred at room temperature for 16 hours. The mixture was filtered through Celite®, washed with more chloroform and the solvent evaporated to afford the title compound (19.9 g, 99%) as a solid.

d) (3-Aminopyridin-4-yl)(2,4-difluorophenyl)methanone

A solution of the title compound of Preparation 1c (19.9 g, 62.7 mmol) in 190 mL of ethanol was treated with HCl 5N (550 mL) and heated to 98° C. for 7 hours. The reaction mixture was cooled down, poured into ice water and the pH adjusted to 9-10 with concentrated aqueous ammonia. The solution was extracted with ethyl acetate (4×200 mL), the organic layer was washed with brine, dried over sodium sulphate and the solvent removed under reduced pressure to yield the title compound (12.2 g, 83%) as a yellowish solid.

e) (3-Amino-1-oxidopyridin-4-yl)(2,4-difluorophenyl)methanone

To a solution of the title compound of Preparation 1d (12.2 g, 52.07 mmol) in dichloromethane (290 mL) at 0° C. was portionwise added meta-chloroperbenzoic acid (17.9 g, 79.82 mmol) and the reaction mixture was stirred overnight at room temperature. Then, more dichloromethane was added (2 L) and the solution was washed with aqueous sodium bicarbonate 4% (4×200 ml) and brine. The organic layer was dried over sodium sulphate and concentrated under reduced pressure to give a residue that was triturated in a mixture of hexane and ethyl acetate (9:1) and filtered to yield the title compound (9.4 g, 72%) as a bright yellow solid.

f) (3-Amino-2-bromopyridin-4-yl)(2,4-difluorophenyl)methanone

The title compound of Preparation 1e (9.4 g, 37.6 mmol) was dissolved in 350 mL of dry dichloromethane and phosphorus oxybromide (31.3 g, 109.2 mmol) portionwise added. The mixture was stirred at 60° C. for 3 hours. The reaction was cooled down, poured into ice water and the pH adjusted to 10-11 with concentrated aqueous ammonia. The solution was extracted with ethyl acetate (2×500 mL), the organic layer was washed with brine, dried over sodium sulphate and the solvent removed under reduced pressure. The residue was purified by column chromatography on silica flash, using n-hexane/ethyl acetate (4:1) as eluents, to yield the title compound (6.85 g, 58%) as a bright yellow solid.
$^1$H-NMR δ (CDCl$_3$): 6.75 (bs, 2H), 6.88-7.09 (m, 2H), 7.12 (dd, J=2 and 4 Hz, 1H), 7.45-7.56 (m, 1H), 7.70 (d, J=6 Hz, 1H).

g) [3-Amino-2-(2-methylphenyl)pyridin-4-yl](2,4-difluorophenyl)methanone

In a Schlenk tube were charged the compound of Preparation 1f (700 mg, 2.23 mmol), 2-methylphenyl boronic acid (456 mg, 3.39 mmol), cesium carbonate (2M aqueous solution, 3.35 mL, 6.7 mmol) and dioxane (18 mL). The mixture was submitted to three vacuum-argon cycles, then [1,1'-bis(diphenylphosphino)ferrocene]dichloropalladium(II) complex with dichloromethane (1:1) (127 mg, 0.15 mmol) was added and the mixture purged in the same way. The reaction was stirred at 80° C. under argon for 17 h. Subsequently, water was added to the cold reaction mixture and it was extracted with ethyl acetate (3×50 ml), the organic solution was washed with brine, dried over sodium sulphate and the solvent removed under reduced pressure. The residue was purified by column chromatography on silica flash, using hexane/ethyl acetate (5:1) as eluents, to yield the title compound (656 mg, 90%) as a yellow solid.
LRMS (m/z): 325 (M+1)$^+$.
Retention Time: 16 min.
$^1$H-NMR δ (CDCl$_3$): 2.21 (s, 3H), 6.17 (brs, 2H), 6.91-7.09 (m, 2H), 7.13 (dd, J=5.1 and 2.7 Hz, 1H), 7.31-7.37 (m, 4H), 7.48-7.59 (m, 1H), 8.00 (d, J=5.1 Hz).

Experimental section for analytical methods: using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 μl. Diode array chromatograms were processed at 210 nm.

Preparation 2

[3-Amino-2-(2-methoxyphenyl)pyridin-4-yl](2,4-difluorophenyl)methanone

Obtained as a yellow solid (81%) from the title compound of Preparation 1f and 2-methoxyphenylboronic acid following the experimental procedure described in Preparation 1 g.

LRMS (m/z): 341 (M+1)+.
Retention Time: 14 min.
$^1$H-NMR δ (CDCl$_3$): 3.85 (s, 3H), 6.30 (brs, 2H), 6.91-7.14 (m, 5H), 7.37-7.57 (m, 3H), 8.00 (d, J=5.5 Hz, 1H).

Preparation 3

[3-Amino-2-(4-hydroxy-2-methylphenyl)pyridin-4-yl](2,4difluorophenyl)methanone Obtained as a yellow solid (58%) from the title compound of Preparation 1f and the title compound of Preparation 52 following the experimental procedure described in Preparation 1 g (18 h at 85° C.).

LRMS (m/z): 341 (M+1)+.
Retention Time: 14 min.
$^1$H-NMR δ (CDCl$_3$): 2.08 (s, 3H), 6.25 (brs, 2H), 6.58-6.62 (m, 2H), 6.90-7.10 (m, 3H), 7.18 (dd, J=2 and 4 Hz, 1H), 7.48-7.59 (m, 1H), 7.97 (d, J=6 Hz, 1H).

Preparation 4

[3-Amino-2-(1,3-benzodioxol-4-yl)pyridin-4-yl](2,4-difluorophenyl)methanone

Obtained as a yellow solid (56%) from the title compound of Preparation 1f and the title compound of Preparation 53 following the experimental procedure described in Preparation 1 g (18 h at 100° C.).

LRMS (m/z): 355 (M+1)+.
Retention Time: 15 min.
$^1$H-NMR δ (CDCl$_3$): 6.06 (s, 2H), 6.8 (brs, 2H), 6.90-7.11 (m, 5H), 7.16 (dd, J=2 and 6 Hz, 1H), 7.46-7.57 (m, 1H), 8.05 (d, J=6 Hz, 1H).

Preparation 5

[3-Amino-2-(2,6-difluorophenyl)pyridin-4-yl](2,4-difluorophenyl)methanone nBuLi (2.5M in hexanes, 0.56 mL) was dropwise added to a solution of 1,3-difluoro-benzene (146 mg, 1.28 mmol) in dry tetrahydrofuran (2 mL) at −78° C. under argon and the resulting mixture was stirred at that temperature for 30 minutes. Then, the reaction mixture was warmed up to −50° C. and ZnCl$_2$ (0.5M in THF, 2.8 mL) carefully added. After 20 minutes, the title compound from Preparation 1f (200 mg, 0.64 mmol, in 1.5 mL of THF) and tetrakis(triphenylphosphine)palladium(0) (66 mg, 0.06 mmol) were sequentially added. The mixture was then submitted to three vacuum-argon cycles and warmed, first to room temperature for 15 minutes and then to 40° C. for 48 hours. After this time the reaction was cooled down and the solvent evaporated under reduced pressure. The resulting crude was purified by column chromatography on silica flash using hexane/ethyl acetate (8:2 to 7:3) as eluents to yield the title compound (150 mg, 68%) as a yellow solid.

LRMS (m/z): 347 (M+1)+.
Retention Time: 15 min.
$^1$H-NMR δ (CDCl$_3$): 6.20 (brs, 2H), 6.93-7.14 (m, 4H), 7.22 (dd, J=5.4 and 3.1 Hz, 1H), 7.39-7.59 (m, 2H), 8.08 (d, J=5.5 Hz, 1H).

Preparation 6

[3-Amino-2-(2,6-dimethylphenyl)pyridin-4-yl](2,4-difluorophenyl)methanone

In a Schlenk tube were charged the compound of Preparation 1f (313 mg, 1 mmol), 2,6-dimethylphenyl boronic acid (299 mg, 2 mmol), potassium carbonate (636 mg, 3 mmol) and toluene (6.2 mL). The mixture was submitted to three vacuum-argon cycles, then 2-(dicyclohexylphosphino)2',6'-dimethoxy-1-1'biphenyl (S-PHOS) (24 mg, 0.06 mmol) and tris(dibenzylideneacetone)dipalladium(0) (27 mg, 0.03 mmol) was added and the mixture purged in the same way. The reaction was stirred at 100° C. under argon for 2 days. Subsequently, water was added to the cold reaction mixture and it was extracted with ethyl acetate (3×50 ml), the organic solution was washed with brine, dried over sodium sulphate and the solvent removed under reduced pressure. The residue was purified by column chromatography on silica flash, using hexane/ethyl acetate (6:1) as eluents, to yield the title compound (150 mg, 44%) as a yellow solid.

LRMS (m/z): 339 (M+1)+.
Retention Time: 17 min.
$^1$H-NMR δ (CDCl$_3$): 2.08 (s, 6H), 6.08 (brs, 2H), 6.91-7.30 (m, 6H), 7.55 (m, 1H), 8.04 (d, J=5.5 Hz, 1H).

Preparation 7

[3-Amino-2-(2,6-dimethoxyphenyl)pyridin-4-yl](2,4-difluorophenyl)methanone

Obtained as a yellow solid (77%) from the title compound of Preparation 1f and 2,6-dimethoxyphenylboronic acid following the experimental procedure described in Preparation 1 g.

LRMS (m/z): 371 (M+1)+.
Retention Time: 13 min.
$^1$H-NMR δ (CDCl$_3$): 3.76 (s, 6H), 6.20 (brs, 2H), 6.70 (d, J=8 Hz, 2H), 6.90-7.07 (m, 2H), 7.10 (dd, J=2 and 4 Hz, 1H), 7.40 (t, J=8 Hz, 1H), 7.45-7.57 (m, 1H), 8.03 (d, J=4 Hz, 1H).

Preparation 8

[3-Amino-2-(2-chlorophenyl)pyridin-4-yl](2,4-difluorophenyl)methanone

Obtained as a yellow solid (78%) from the title compound of Preparation 1f and 2-chlorophenylboronic acid following the experimental procedure described in Preparation 1 g.

LRMS (m/z): 345, 347 (M+1)+.
Retention Time: 16 min.
$^1$H-NMR δ (CDCl$_3$): 6.02 (brs, 2H), 6.92-7.10 (m, 2H), 7.18 (dd, J=5.5 and 2.8 Hz, 1H), 7.47-7.75 (m, 4H), 7.88 (m, 1H), 8.00 (d, J=5.4 Hz, 1H).

Preparation 9

[3-Amino-2-(2-fluorophenyl)pyridin-4-yl](2,4-difluorophenyl)methanone

Obtained as a yellow solid (86%) from the title compound of Preparation 1f and 2-fluorophenylboronic acid following the experimental procedure described in Preparation 1 g.

LRMS (m/z): 329 (M+1)+.

¹H-NMR δ (CDCl₃): 6.30 (brs, 2H), 6.91-7.09 (m, 2H), 7.17 (dd, J=2 and 4 Hz, 1H), 7.20-7.36 (m, 2H), 7.40-7.59 (m, 3H), 8.04 (d, J=6 Hz, 1H).

Preparation 10

[3-Amino-2-(2,6-dichlorophenyl)pyridin-4-yl](2,4-difluorophenyl)methanone

Obtained as a yellow solid (50%) from the title compound of Preparation 1f and 2,6-dichlorophenylboronic acid following the experimental procedure described in Preparation 6.
LRMS (m/z): 379, 381, 383 (M+1)⁺.
Retention Time: 16 min.
¹H-NMR δ (CDCl₃): 6.06 (brs, 2H), 6.91-7.10 (m, 2H), 7.23 (dd, J=5.5 and 3.1 Hz, 1H), 7.33-7.61 (m, 4H), 8.09 (d, J=5.4 Hz, 1H).

Preparation 11

[3-Amino-2-(2-methylphenyl)-1-oxidopyridin-4-yl](2,4-difluorophenyl)methanone

To a solution of the title compound from Preparation 1 g (500 mg, 1.54 mmol) in dichloromethane (5.7 mL) at 0° C. was portionwise added meta-chloroperbenzoic acid (516 mg, 2.31 mmol) and the reaction mixture was stirred overnight at room temperature. Then, more dichloromethane was added (50 mL) and the solution was washed with aqueous sodium bicarbonate 4% (3×30 ml) and brine. The organic layer was dried over sodium sulphate and concentrated under reduced pressure to give a residue that was purified by column chromatography on silica flash, using hexane/ethyl acetate (1:4) as eluents, to yield the title compound (473 mg, 90%) as a yellow solid.
LRMS (m/z): 341 (M+1)⁺.
Retention Time: 20 min.
¹H-NMR δ (CDCl₃): 2.21 (s, 3H), 6.40 (brs, 2H), 6.91-7.10 (m, 2H), 7.20 (dd, J=7.0 and 3.1 Hz, 1H), 7.29 (m, 1H), 7.35-7.57 (m, 4H), 7.64 (d, J=7.0 Hz, 1H).

Preparation 12

[3-amino-2-(2-methoxyphenyl)-1-oxidopyridin-4-yl](2,4-difluorophenyl)methanone

Obtained as a yellow solid (79%) from the title compound of Preparation 2 following the experimental procedure of Preparation 11.
LRMS (m/z): 357 (M+1)⁺.
Retention Time: 13 min.
¹H-NMR δ (CDCl₃): 3.85 (s, 3H), 6.45 (brs, 2H), 6.91-7.19 (m, 5H), 7.31 (m, 1H), 7.44-7.57 (m, 2H), 7.62 (d, J=7 Hz, 1H).

Preparation 13

[3-Amino-2-(4-hydroxy-2-methylphenyl)-1-oxidopyridin-4-yl](2,4-difluorophenyl)-methanone Obtained as a yellow solid (99%) from the title compound of Preparation 3 following the experimental procedure of Preparation 11.
LRMS (m/z): 357 (M+1)⁺.
Retention Time: 13 min.
¹H-NMR δ (DMSO-d₆): 1.94 (s, 3H), 6.70-6.80 (m, 2H), 6.88 (brs, 2H), 6.97 (d, J=8 Hz, 1H), 7.14 (dd, J=2 and 8 Hz, 1H), 7.20-7.30 (m, 1H), 7.40-7.50 (m, 1H), 7.51 (d, J=8 Hz, 1H), 7.60-7.70 (m, 1H).

Preparation 14

[3-Amino-2-(1,3-benzodioxol-4-yl)-1-oxidopyridin-4-yl](2,4-difluorophenyl)-methanone Obtained as a yellow solid (43%) from the title compound of Preparation 4 following the experimental procedure of Preparation 11.
LRMS (m/z): 371 (M+1)⁺.
Retention Time: 13 min.
¹H-NMR δ (CDCl₃): 6.06 (dd, J=2 and 12 Hz, 2H), 6.62 (brs, 2H), 6.88-7.09 (m, 5H), 7.19 (dd, J=4 and 8 Hz, 1H), 7.43-7.55 (m, 1H), 7.64 (d, J=8 Hz, 1H).

Preparation 15

[3-Amino-2-(2,6-difluorophenyl)-1-oxidopyridin-4-yl](2,4-difluorophenyl)methanone Obtained as a yellow solid (73%) from the title compound of Preparation 5 following the experimental procedure of Preparation 11.
LRMS (m/z): 363 (M+1)⁺.
Retention Time: 13 min.
¹H-NMR δ (CDCl₃): 6.49 (brs, 2H), 6.92-7.17 (m, 4H), 7.27 (m, 1H), 7.46-7.60 (m, 2H), 7.67 (d, J=7.1 Hz, 1H).

Preparation 16

[3-Amino-2-(2,6-dimethylphenyl)-1-oxidopyridin-4-yl](2,4-difluorophenyl)methanone Obtained as a yellow solid (73%) from the title compound of Preparation 6 following the experimental procedure of Preparation 11.
LRMS (m/z): 355 (M+1)⁺.
Retention Time: 14 min.
¹H-NMR δ (CDCl₃): 2.14 (s, 6H), 6.35 (brs, 2H), 6.92-7.10 (m, 2H), 7.19-7.38 (m, 4H), 7.53 (m, 1H), 7.67 (d, J=7.1 Hz, 1H).

Preparation 17

[3-Amino-2-(2,6-dimethoxyphenyl)-1-oxidopyridin-4-yl](2,4-difluorophenyl)-methanone Obtained as a yellow solid (83%) from the title compound of Preparation 7 following the experimental procedure of Preparation 11.
LRMS (m/z): 387 (M+1)⁺.
Retention Time: 13 min.
¹H-NMR δ (CDCl₃): 3.80 (s, 6H), 6.46 (brs, 2H), 6.72 (d, J=8 Hz, 2H), 6.90-7.08 (m, 2H), 7.14 (dd, J=2 and 8 Hz, 1H), 7.43-7.51 (m, 2H), 7.60 (d, J=8 Hz, 1H).

Preparation 18

N-{4-[3-Amino-4-(2,4-difluorobenzoyl)-1-oxidopyridin-2-yl]-3-methylphenyl}-methanesulfonamide a) N-{4-[3-Amino-4-(2,4-difluorobenzoyl)pyridin-2-yl]-3-methylphenyl}methane-sulfonamide Obtained as a yellow solid (54%) from the title compound of Preparation 1f and the title compound of Preparation 54 following the experimental procedure described in Preparation 1 g.
LRMS (m/z): 418 (M+1)$^+$.
Retention Time: 13.7 min.

b) N-{4-[3-Amino-4-(2,4-difluorobenzoyl)-1-oxidopyridin-2-yl]-3-methylphenyl}-methanesulfonamide Obtained as a yellow solid (54%) from the title compound of Preparation 18a following the experimental procedure of Preparation 11.
LRMS (m/z): 434 (M+1)$^+$.
Retention Time: 13 min.
$^1$H-NMR δ (CDCl$_3$): 2.18 (s, 3H), 3.06 (s, 3H), 6.40 (brs, 2H), 6.92-7.16 (m, 5H), 7.22 (dd, J=4 and 6 Hz, 1H), 7.47-7.58 (m, 1H), 7.69 (d, J=6 Hz, 1H), 7.81 (brs, 1H).

Preparation 19

[3-Amino-2-(2-chlorophenyl)-1-oxidopyridin-4-yl](2,4-difluorophenyl)methanone Obtained as a yellow solid (72%) from the title compound of Preparation 8 following the experimental procedure of Preparation 11.
LRMS (m/z): 361, 363 (M+1)$^+$.
Retention Time: 13 min.
$^1$H-NMR δ (CDCl$_3$): 6.38 (brs, 2H), 6.92-7.10 (m, 2H), 7.24 (dd, J=7.0 and 2.8 Hz, 1H), 7.38-7.58 (m, 4H), 7.62-7.67 (m, 2H).

Preparation 20

[3-Amino-2-(2-fluorophenyl)-1-oxidopyridin-4-yl](2,4-difluorophenyl)methanone Obtained as a yellow solid (100%) from the title compound of Preparation 9 following the experimental procedure of Preparation 11.
LRMS (m/z): 345 (M+1)$^+$.
$^1$H-NMR δ (CDCl$_3$): 6.51 (brs, 2H), 6.95-7.09 (m, 2H), 7.23-7.59 (m, 6H), 7.72 (d, J=6 Hz, 1H).

Preparation 21

[3-Amino-2-(2,6-dichlorophenyl)-1-oxidopyridin-4-yl](2,4-difluorophenyl)methanone Obtained as a yellow solid (87%) from the title compound of Preparation 10 following the experimental procedure of Preparation 11.
LRMS (m/z): 395, 397, 399 (M+1)$^+$.
Retention Time: 14 min.
$^1$H-NMR δ (CDCl$_3$): 6.35 (brs, 2H), 6.92-7.11 (m, 2H), 7.28 (dd, J=7.4 and 2.7 Hz, 1H), 7.40-7.59 (m, 4H), 7.67 (d, J=7.0 Hz, 1H).

Preparation 22

[3-Amino-2-(2,6-difluorophenyl)pyridin-4-yl](2-chloro-4-fluorophenyl)methanone a) N-{4-[(2-Chloro-4-fluorophenyl)(hydroxy)methyl]pyridin-3-yl}-2,2-dimethyl-propanamide nBuLi (2.5M in hexanes, 56.2 mL, 140.5 mmol) was dropwise added to a solution of the title compound of Preparation 1a (10 g, 56.2 mmol) and N,N,N',N'-tetramethylethylenediamine (TMEDA) (20.9 mL, 140.5 mmol) in diethyl ether (338 mL) at −78° C. under argon and the resulting mixture was stirred at that temperature for 15 minutes and at −10° C. for 2 hours. Then, the reaction mixture was cooled down to −78° C. and 2-chloro-4-fluorobenzal-dehyde (20 g, 140.5 mmol) in 34 mL of dry tetrahydrofuran was carefully added. After 15 minutes, the cooling bath was removed and the mixture stirred overnight at room temperature. Subsequently, water (100 mL) was added to the flask and it was extracted with ethyl acetate (3×200 mL), the organic solution was washed with brine, dried over sodium sulphate and the solvent removed under reduced pressure. The residue was purified by column chromatography on silica flash, using dichloromethane/ethyl acetate (7:3) as eluents, to yield the title compound (6.15 g, 33%) as a solid.

b) N-[4-(2-Chloro-4-fluorobenzoyl)pyridin-3-yl]-2,2-dimethylpropanamide

Obtained as a yellow solid (99%) from the title compound of Preparation 22a following the experimental procedure described in Preparation 1c.

c) (3-Aminopyridin-4-yl)(2-chloro-4-fluorophenyl)methanone

Obtained as a bright yellow solid (92%) from the title compound of Preparation 22b following the experimental procedure described in Preparation 1d.

d) (3-Amino-1-oxidopyridin-4-yl)(2-chloro-4-fluorophenyl)methanone

Obtained as a bright yellow solid (83%) from the title compound of Preparation 22c following the experimental procedure described in Preparation 1e.

e) (3-Amino-2-bromopyridin-4-yl)(2-chloro-4-fluorophenyl)methanone

Obtained as a bright yellow solid (46%) from the title compound of Preparation 22d following the experimental procedure described in Preparation 1f.
$^1$H-NMR δ (CDCl$_3$): 6.88 (brs, 2H), 6.96 (d, J=6 Hz, 1H), 7.08-7.17 (m, 1H), 7.23 (dd, J=2 and 8 Hz, 1H), 7.34 (dd, J=6 and 10 Hz, 1H), 7.65 (d, J=6 Hz, 1H).

f) [3-Amino-2-(2,6-difluorophenyl)pyridin-4-yl](2-chloro-4-fluorophenyl)methanone Obtained as a yellow solid (93%) from the title compound of Preparation 22e and 1,3-difluorobenzene following the experimental procedure of Preparation 5.
$^1$H-NMR δ (CDCl$_3$): 6.32 (brs, 2H), 7.03-7.18 (m, 4H), 7.27 (dd, J=2 and 8 Hz, 1H), 7.36-7.55 (m, 2H), 8.03 (d, J=6 Hz, 1H).

Preparation 23

[3-Amino-2-(2,6-dichlorophenyl)pyridin-4-yl](2-chloro-4-fluorophenyl)methanone Obtained as a yellow solid (26%) from the title compound of Preparation 22e and 2,6-dichlorophenylboronic acid following the experimental procedure described in Preparation 6.

LRMS (m/z): 395, 397, 399, 401 (M+1)$^+$.
$^1$H-NMR δ (CDCl$_3$): 6.16 (brs, 2H), 7.07 (d, J=6 Hz, 1H), 7.11-7.18 (m, 1H), 7.25-7.29 (m, 1H), 7.35-7.45 (m, 2H), 7.48-7.52 (m, 211), 8.04 (d, J=6 Hz, 1H).

Preparation 24

[3-Amino-2-(2,6-difluorophenyl)-1-oxidopyridin-4-yl](2-chloro-4-fluorophenyl)-methanone Obtained as a yellow solid (98%) from the title compound of Preparation 22f following the experimental procedure of Preparation 11.

LRMS (m/z): 379 (M+1)$^+$.
$^1$H-NMR δ (CDCl$_3$): 6.56 (brs, 2H), 7.10-7.20 (m, 4H), 7.27 (dd, J=2 and 8 Hz, 1H), 7.36-7.44 (m, 1H), 7.49-7.61 (m, 1H), 7.65 (d, J=8 Hz, 1H).

Preparation 25

[3-Amino-2-(2,6-dichlorophenyl)-1-oxidopyridin-4-yl](2-chloro-4-fluorophenyl)-methanone Obtained as a yellow solid (76%) from the title compound of Preparation 23 following the experimental procedure of Preparation 11.

$^1$H-NMR δ (CDCl$_3$): 6.40 (brs, 2H), 7.12 (d, J=8 Hz, 1H), 7.11-7.20 (m, 1H), 7.26 (dd, J=2 and 8 Hz, 1H), 7.39-7.57 (m, 4H), 7.63 (d, J=8 Hz, 1H).

Preparation 26

[3-Amino-2-(2-chlorophenyl)-1-oxidopyridin-4-yl](2-chloro-4-fluorophenyl)-methanone a) [3-Amino-2-(2-chlorophenyl)pyridin-4-yl](2-chloro-4-fluorophenyl)methanone Obtained as a yellow solid (69%) from the title compound of Preparation 22e and 2-chlorophenylboronic acid following the experimental procedure described in Preparation 1 g.

LRMS (m/z): 361, 363, 365 (M+1)$^+$.

b) [3-Amino-2-(2-chlorophenyl)-1-oxidopyridin-4-yl](2-chloro-4-fluorophenyl)-methanone Obtained as a yellow solid (38%) from the title compound of Preparation 26a following the experimental procedure of Preparation 11.

LRMS (m/z): 377, 379, 381 (M+1)$^+$.

Preparation 27

[3-Amino-2-(2,6-difluorophenyl)pyridin-4-yl](2-chlorophenyl)methanone a) N-{4-[(2-Chlorophenyl)(hydroxy)methyl]pyridin-3-yl}-2,2-dimethylpropanamide nBuLi (2.5M in hexanes, 30 mL, 75 mmol) was dropwise added to a solution of the title compound of Preparation 1a (5 g, 28.3 mmol) in dry tetrahydrofuran (70 mL) at −78° C. under argon and the resulting mixture was stirred at that temperature for 15 minutes and at 0° C. for 3 hours. Then, the reaction mixture was cooled down to −78° C. and benzaldehyde (4.93 g, 43.4 mmol) in 7 mL of tetrahydrofuran was carefully added. After 15 minutes, the cooling bath was removed and the mixture stirred overnight at room temperature. Subsequently, the mixture was poured into water (300 mL) and it was extracted with ethyl acetate (3×300 mL). The organic solution was washed with brine, dried over anhydrous sodium sulphate and the solvent removed under reduced pressure. The residue was purified by column chromatography on silica flash, using n-hexane/ethyl acetate (1:4) as eluents, to yield the title compound (2.98 g, 33%) as a white solid.

b) N-[4-(2-Chlorobenzoyl)pyridin-3-yl]-2,2-dimethylpropanamide)

Obtained as a yellow solid (97%) from the title compound of Preparation 27a following the experimental procedure described in Preparation 1c.

c) (3-Aminopyridin-4-yl)(2-chlorophenyl)methanone

Obtained as a bright yellow solid (95%) from the title compound of Preparation 27b following the experimental procedure described in Preparation 1d.

d) (3-Amino-1-oxidopyridin-4-yl)(2-chlorophenyl)methanone

Obtained as a bright yellow solid (88%) from the title compound of Preparation 27c following the experimental procedure described in Preparation 1e.

e) (3-Amino-2-bromopyridin-4-yl)(2-chlorophenyl)methanone

Obtained as a bright yellow solid (57%) from the title compound of Preparation 27d following the experimental procedure described in Preparation 1f.

$^1$H-NMR δ (CDCl$_3$): 6.90 (bs, 2H), 6.98 (d, J=6 Hz, 1H), 7.29-7.49 (m, 4H), 7.64 (d, J=6 Hz, 1H).

f) [3-Amino-2-(2,6-difluorophenyl)pyridin-4-yl](2-chlorophenyl)methanone

Obtained as a yellow solid (46%) from the title compound of Preparation 27e following the experimental procedure of Preparation 5.

LRMS (m/z): 345-347 (M+1)$^+$.
Retention Time: 15 min.
$^1$H-NMR δ (CDCl$_3$): 6.34 (brs, 2H), 7.05-7.13 (m, 3H), 7.38-7.51 (m, 5H), 8.03 (d, J=6 Hz, 1H).

Preparation 28

[3-Amino-2-(2,6-dichlorophenyl)pyridin-4-yl](2-chlorophenyl)methanone

Obtained as a yellow solid (46%) from the title compound of Preparation 27e and 2,6-dichlorophenylboronic acid following the experimental procedure described in Preparation 6.

LRMS (m/z): 377, 379, 381, 383 (M+1)$^+$.

¹H-NMR δ (CDCl₃): 6.18 (brs, 2H), 7.09 (d, J=4 Hz, 1H), 7.34-7.43 (m, 3H), 7.47-7.53 (m, 4H), 8.03 (d, J=4 Hz, 1H).

Preparation 29

[3-Amino-2-(2,6-difluorophenyl)-1-oxidopyridin-4-yl](2-chlorophenyl)methanone

Obtained as a yellow solid (70%) from the title compound of Preparation 27f following the experimental procedure of Preparation 11.
LRMS (m/z): 361-363 (M+1)⁺.
Retention Time: 14 min.
¹H-NMR δ (CDCl₃): 6.57 (brs, 2H), 7.09-7.17 (m, 3H), 7.36-7.56 (m, 5H), 7.62 (d, J=6 Hz, 1H).

Preparation 30

[3-Amino-2-(2,6-dichlorophenyl)-1-oxidopyridin-4-yl](2-chlorophenyl)methanone

Obtained as a yellow solid (61%) from the title compound of Preparation 28 following the experimental procedure of Preparation 11.
LRMS (m/z): 393, 395, 397, 399 (M+1)⁺.
¹H-NMR δ (CDCl₃): 6.42 (brs, 2H), 7.13 (d, J=6 Hz, 1H), 7.40-7.57 (m, 7H), 7.61 (d, J=6 Hz, 1H).

Preparation 31

[3-Amino-2-(2,6-difluorophenyl)pyridin-4-yl](2-methoxyphenyl)methanone a) N-{4-[Hydroxy(2-methoxyphenyl)methyl]pyridin-3-yl}-2,2-dimethylpropanamide nBuLi (2.5M in hexanes, 56.2 mL, 140.5 mmol) was dropwise added to a solution of the title compound of Preparation 1a (10 g, 56.2 mmol) and N,N,N',N'-tetramethylethylenediamine (TMEDA) (20.9 mL, 140.5 mmol) in diethyl ether (338 mL) at −78° C. under argon and the resulting mixture was stirred at that temperature for 15 minutes and at −10° C. for 2 hours. Then, the reaction mixture was cooled down to −78° C. and 2-methoxybenzaldehyde (19.52 g, 140.5 mmol) in 34 mL of dry tetrahydrofuran was carefully added. After 15 minutes, the cooling bath was removed and the mixture stirred overnight at room temperature. Subsequently, water (100 mL) was added to the flask and it was extracted with ethyl acetate (3×200 mL), the organic solution was washed with brine, dried over sodium sulphate and the solvent removed under reduced pressure. The residue was purified by column chromatography on silica flash, using hexane/ethyl acetate (4:1) as eluents, to yield the title compound (11.1 g, 63%) as a solid.

b) N-[4-(2-Methoxybenzoyl)pyridin-3-yl]-2,2-dimethylpropanamide

Obtained as a yellow solid (99%) from the title compound of Preparation 31a following the experimental procedure described in Preparation 1c.

c) (3-Aminopyridin-4-yl)(2-methoxyphenyl)methanone

Obtained as a bright yellow solid (85%) from the title compound of Preparation 31b following the experimental procedure described in Preparation 1d.

d) (3-Amino-1-oxidopyridin-4-yl)(2-methoxyphenyl)methanone

Obtained as a bright yellow solid (80%) from the title compound of Preparation 31c following the experimental procedure described in Preparation 1e.

e) (3-Amino-2-bromopyridin-4-yl)(2-methoxyphenyl)methanone

Obtained as a bright yellow solid (61%) from the title compound of Preparation 31d following the experimental procedure described in Preparation 1f.
¹H-NMR δ (CDCl₃): 3.75 (s, 3H), 6.79 (brs, 2H), 6.98-7.10 (m, 2H), 7.04 (d, J=6 Hz, 1H), 7.27-7.31 (m, 1H), 7.45-7.52 (m, 1H), 7.62 (d, J=6 Hz, 1H).

f) [3-Amino-2-(2,6-difluorophenyl)pyridin-4-yl](2-methoxyphenyl)methanone

Obtained as a yellow solid (60%) from the title compound of Preparation 31e and 1,3-difluorobenzene following the experimental procedure of Preparation 5.
LRMS (m/z): 341 (M+1)⁺.
Retention Time: 14 min.
¹H-NMR δ (CDCl₃): 3.80 (s, 3H), 6.24 (brs, 2H), 7.01-7.12 (m, 4H), 7.18 (d, J=6 Hz, 1H), 7.33 (dd, J=2 and 8 Hz, 1H), 7.37-7.54 (m, 2H), 8.01 (d, J=6 Hz, 1H).

Preparation 32

[3-Amino-2-(2,6-dimethylphenyl)pyridin-4-yl](2-methoxyphenyl)methanone

Obtained as a yellow solid (50%) from the title compound of Preparation 31e and 2,6-dimethylphenylboronic acid following the experimental procedure described in Preparation 6.
LRMS (m/z): 333 (M+1)⁺.
Retention Time: 15 min.
¹H-NMR δ (CDCl₃): 2.08 (s, 6H), 3.80 (s, 3H), 6.09 (brs, 2H), 7.01-7.25 (m, 6H), 7.34 (dd, J=2 and 8 Hz, 1H), 7.45-7.54 (m, 1H), 7.98 (d, J=6 Hz, 1H).

Preparation 33

N-{4-[3-Amino-4-(2-methoxybenzoyl)pyridin-2-yl]-3-methylphenyl}methanesulfonamide Obtained as a yellow solid (57%) from the title compound of Preparation 31e and the title compound of Preparation 54 following the experimental procedure described in Preparation 1g (18 h at 100° C.).
LRMS (m/z): 412 (M+1)⁺.
Retention Time: 13 min.
¹H-NMR δ (CDCl₃): 2.21 (s, 3H), 3.06 (s, 3H), 3.81 (s, 3H), 6.20 (brs, 2H), 7.01-7.16 (m, 5H), 7.25-7.36 (m, 2H), 7.46-7.55 (m, 1H), 7.96 (d, J=6 Hz, 1H).

Preparation 34

[3-Amino-2-(2,6-difluorophenyl)-1-oxidopyridin-4-yl](2-methoxyphenyl)methanone

Obtained as a yellow solid (71%) from the title compound of Preparation 31 following the experimental procedure of Preparation 11.

LRMS (m/z): 357 (M+1)+.

Retention Time: 13 min.

$^1$H-NMR δ (CDCl$_3$): 3.82 (s, 3H), 6.52 (brs, 2H), 7.01-7.23 (m, 5H), 7.32 (dd, J=2 and 8 Hz, 1H), 7.45-7.59 (m, 2H), 7.61 (d, J=6 Hz, 1H).

Preparation 35

[3-Amino-2-(2,6-dimethylphenyl)-1-oxidopyridin-4-yl](2-methoxyphenyl)methanone

Obtained as a yellow solid (70%) from the title compound of Preparation 32 following the experimental procedure of Preparation 11.

LRMS (m/z): 349 (M+1)+.

Retention Time: 14 min.

$^1$H-NMR δ (CDCl$_3$): 2.15 (s, 6H), 3.82 (s, 3H), 6.34 (brs, 2H), 7.01-7.12 (m, 2H), 7.17 (d, J=6 Hz, 1H), 7.20-7.24 (m, 2H), 7.30-7.36 (m, 2H), 7.45-7.54 (m, 1H), 7.61 (d, J=6 Hz, 1H).

Preparation 36

[3-amino-2-(4-amino-2-methylphenyl)-1-oxidopyridin-4-yl](2-methoxyphenyl)-methanesulfonamide Obtained as a yellow solid (68%) from the title compound of Preparation 33 following the experimental procedure of Preparation 11.

LRMS (m/z): 428 (M+1)+.

Retention Time: 12 min.

$^1$H-NMR δ (CDCl$_3$): 2.17 (s, 3H), 3.04 (s, 3H), 3.83 (s, 3H), 6.44 (brs, 2H), 6.99-7.15 (m, 5H), 7.20 (d, J=6 Hz, 1H), 7.34 (dd, J=2 and 8 Hz, 1H), 7.46-7.55 (m, 1H), 7.64 (d, J=6 Hz, 1H), 8.22 (brs, 1H).

Preparation 37

[3-Amino-2-(2-chlorophenyl)-1-oxidopyridin-4-yl](2-methoxyphenyl)methanone a) [3-Amino-2-(2-chlorophenyl)pyridin-4-yl](2-methoxyphenyl)methanone Obtained as a yellow solid (60%) from the title compound of Preparation 31e and 2-chlorophenylboronic acid following the experimental procedure described in Preparation 1 g.

LRMS (m/z): 339 (M+1)+.

b) [3-Amino-2-(2-chlorophenyl)-1-oxidopyridin-4-yl](2-methoxyphenyl)methanone

Obtained as a yellow solid (83%) from the title compound of Preparation 37a following the experimental procedure of Preparation 11.

LRMS (m/z): 355 (M+1)+.

Retention Time: 13 min.

$^1$H-NMR δ (CDCl$_3$): 3.82 (s, 3H), 6.39 (brs, 2H), 7.01-7.12 (m, 2H), 7.19 (d, J=6 Hz, 1H), 7.33 (dd, J=2 and 8 Hz, 1H), 7.38-7.54 (m, 4H), 7.60 (d, J=6 Hz, 1H), 7.60-7.66 (m, 1H).

Preparation 38

[3-Amino-2-(2-methoxyphenyl)-1-oxidopyridin-4-yl](2-methoxyphenyl)methanone a) [3-Amino-2-(2-methoxyphenyl)pyridin-4-yl](2-methoxyphenyl)methanone Obtained as a yellow solid (79%) from the title compound of Preparation 31e and 2-methoxyphenylboronic acid following the experimental procedure described in Preparation 1 g.

LRMS (m/z): 335 (M+1)+.

$^1$H-NMR δ (CDCl$_3$): 3.80 (s, 3H), 3.84 (s, 3H), 6.35 (brs, 2H), 7.00-7.15 (m, 4H), 7.08 (d, J=6 Hz, 1H), 7.29-7.52 (m, 4H), 7.93 (d, J=6 Hz, 1H).

b) [3-Amino-2-(2-methoxyphenyl)-1-oxidopyridin-4-yl](2-methoxyphenyl)methanone

Obtained as a yellow solid (93%) from the title compound of Preparation 38a following the experimental procedure of Preparation 11.

LRMS (m/z): 351 (M+1)+.

Retention Time: 12 min.

$^1$H-NMR δ (CDCl$_3$): 3.82 (s, 3H), 3.84 (s, 3H), 6.47 (brs, 2H), 7.00-7.19 (m, 4H), 7.12 (d, J=6 Hz, 1H), 7.27-7.34 (m, 2H), 7.44-7.55 (m, 2H), 7.57 (d, J=6 Hz, 1H).

Preparation 39

[3-Amino-2-(2-methoxyphenyl)-1-oxidopyridin-4-yl][3-(trifluoromethyl)phenyl]-methanone a) N-(4-{Hydroxy[3-(trifluoromethyl)phenyl]methyl}pyridin-3-yl)-2,2-dimethylpropanamide nBuLi (2.5M in hexanes, 56.2 mL, 140.5 mmol) was dropwise added to a solution of the title compound of Preparation 1a (10 g, 56.2 mmol) and N,N,N',N'-tetramethylethylenediamine (TMEDA) (20.9 mL, 140.5 mmol) in diethyl ether (338 mL) at −78° C. under argon and the resulting mixture was stirred at that temperature for 15 minutes and at −10° C. for 2 hours. Then, the reaction mixture was cooled down to −78° C. and 3-(trifluoromethyl)-benzaldehyde (24.5 g, 140.5 mmol) in 34 mL of dry tetrahydrofuran was carefully added. After 15 minutes, the cooling bath was removed and the mixture stirred overnight at room temperature. Subsequently, water (100 mL) was added to the flask and it was extracted with ethyl acetate (3×200 mL), the organic solution was washed with brine, dried over sodium sulphate and the solvent removed under reduced pressure. The residue was purified by recrystallization in hexane (300 mL)/ethyl acetate (50 mL) to yield the title compound (10.29 g, 52%) as a solid.

b) 2,2-Dimethyl-N-{4-[3-(trifluoromethyl)benzoyl]pyridin-3-yl}propanamide

Obtained as a yellow solid (96%) from the title compound of Preparation 39a following the experimental procedure described in Preparation 1c.

c) (3-Aminopyridin-4-yl)[3-(trifluoromethyl)phenyl]methanone

Obtained as a bright yellow solid (89%) from the title compound of Preparation 39b following the experimental procedure described in Preparation 1d.

d) (3-Amino-1-oxidopyridin-4-yl)[3-(trifluoromethyl)phenyl]methanone

Obtained as a bright yellow solid (33%) from the title compound of Preparation 39c following the experimental procedure described in Preparation 1e.

e) (3-Amino-2-bromopyridin-4-yl)[3-(trifluoromethyl)phenyl]methanone

Obtained as a bright yellow solid (42%) from the title compound of Preparation 39d following the experimental procedure described in Preparation 1f.

$^1$H-NMR δ (CDCl$_3$): 6.53 (brs, 2H), 7.18 (d, J=4 Hz, 1H), 7.63-7.68 (m, 1H), 7.74 (d, J=4 Hz, 1H), 7.83-7.88 (m, 2H), 7.94 (s, 1H).

f) [3-Amino-2-(2-methoxyphenyl)pyridin-4-yl][3-(trifluoromethyl)phenyl]methanone Obtained as a yellow solid (90%) from the title compound of Preparation 39e and 2-methoxyphenylboronic acid following the experimental procedure of Preparation 1 g.

LRMS (m/z): 373 (M+1)$^+$.

g) [3-Amino-2-(2-methoxyphenyl)-1-oxidopyridin-4-yl][3-(trifluoromethyl)phenyl]-methanone Obtained as a yellow solid (54%) from the title compound of Preparation 39f following the experimental procedure of Preparation 11.

LRMS (m/z): 389 (M+1)$^+$.

$^1$H-NMR δ (CDCl$_3$): 3.84 (s, 3H), 6.35 (brs, 2H), 7.10-7.20 (m, 2H), 7.26 (d, J=8 Hz, 1H), 7.31 (dd, J=2 and 8 Hz, 1H), 7.49-7.58 (m, 1H), 7.62-7.70 (m, 1H), 7.65 (d, J=8 Hz, 1H), 7.80-7.86 (m, 2H), 7.92 (s, 1H).

Preparation 40

[3-Amino-2-(2,6-difluorophenyl)-1-oxidopyridin-4-yl][3-(trifluoromethyl)phenyl]-methanone a) [3-Amino-2-(2,6-difluorophenyl)pyridin-4-yl][3-(trifluoromethyl)phenyl]methanone Obtained as a yellow solid (17%) from the title compound of Preparation 39e and 1,3-difluorobenzene following the experimental procedure of Preparation 5.

LRMS (m/z): 379 (M+1)$^+$.

$^1$H-NMR δ (CDCl$_3$): 5.97 (brs, 2H), 7.04-7.15 (m, 2H), 7.27 (d, J=6 Hz, 1H), 7.40-7.55 (m, 1H), 7.63-7.71 (m, 1H), 7.86-7.94 (m, 2H), 8.01 (s, 1H), 8.12 (d, J=6 Hz, 1H).

b) [3-Amino-2-(2,6-difluorophenyl)-1-oxidopyridin-4-yl][3-(trifluoromethyl)phenyl]-methanone Obtained as a yellow solid (79%) from the title compound of Preparation 40a following the experimental procedure of Preparation 11.

LRMS (m/z): 395 (M+1)$^+$.

$^1$H-NMR δ (CDCl$_3$): 6.40 (brs, 2H), 7.10-7.18 (m, 2H), 7.36 (d, J=8 Hz, 1H), 7.49-7.64 (m, 2H), 7.70 (d, J=8 Hz, 1H), 7.83-7.87 (m, 2H), 7.94 (s, 1H).

Preparation 41

[3-Amino-2-(2,6-dichlorophenyl)-1-oxidopyridin-4-yl][3-(trifluoromethyl)phenyl]-methanone a) [3-Amino-2-(2,6-dichlorophenyl)pyridin-4-yl][3-(trifluoromethyl)phenyl]methanone Obtained as a yellow solid (36%) from the title compound of Preparation 39e and 2,6-dichlorophenylboronic acid following the experimental procedure described in Preparation 6.

LRMS (m/z): 411, 413, 415 (M+1)$^+$.

b) [3-Amino-2-(2,6-dichlorophenyl)-1-oxidopyridin-4-yl][3-(trifluoromethyl)phenyl]-methanone Obtained as a yellow solid (49%) from the title compound of Preparation 41a following the experimental procedure of Preparation 11.

LRMS (m/z): 427, 429, 431(M+1)$^+$.

$^1$H-NMR δ (CDCl$_3$): 6.29 (brs, 2H), 7.37 (d, J=6 Hz, 1H), 7.41-7.58 (3H), 7.63-7.71 (m, 1H), 7.69 (d, J=8 Hz, 1H), 7.84-7.88 (m, 2H), 7.94 (s, 1H).

Preparation 42

[3-Amino-2-(2,6-difluorophenyl)-1-oxidopyridin-4-yl][4-(trifluoromethyl)phenyl]-methanol a) N-(4-{Hydroxy[4-(trifluoromethyl)phenyl]methyl}pyridin-3-yl)-2,2-dimethylpropanamide nBuLi (2.5M in hexanes, 56.2 mL, 140.5 mmol) was dropwise added to a solution of the title compound of Preparation 1a (10 g, 56.2 mmol) and N,N,N',N'-tetramethylethylenediamine (TMEDA) (20.9 mL, 140.5 mmol) in diethyl ether (338 mL) at −78° C. under argon and the resulting mixture was stirred at that temperature for 15 minutes and at −10° C. for 2 hours. Then, the reaction mixture was cooled down to −78° C. and 4-(trifluoromethyl)-benzaldehyde (21.86 g, 125.6 mmol) in 34 mL of dry tetrahydrofuran was carefully added. After 15 minutes, the cooling bath was removed and the mixture stirred overnight at room temperature. Subsequently, water (100 mL) was added to the flask and it was extracted with ethyl acetate (3×200 mL), the organic solution was washed with brine, dried over sodium sulphate and the solvent removed under reduced pressure. The residue was purified by recrystallization in hexane (140 mL)/ethyl acetate (140 mL) to yield the title compound (10.56 g, 53%) as a solid.

b) 2,2-Dimethyl-N-{4-[4-(trifluoromethyl)benzoyl]pyridin-3-yl}propanamide

Obtained as a yellow solid (95%) from the title compound of Preparation 42a following the experimental procedure described in Preparation 1c.

c) (3-Aminopyridin-4-yl)[4-(trifluoromethyl)phenyl] methanone

Obtained as a bright yellow solid (89%) from the title compound of Preparation 42b following the experimental procedure described in Preparation 1d.

d) (3-Amino-1-oxidopyridin-4-yl)[4-(trifluoromethyl)phenyl]methanone

Obtained as a bright yellow solid (74%) from the title compound of Preparation 42c following the experimental procedure described in Preparation 1e.

e) (3-Amino-2-bromopyridin-4-yl)[4-(trifluoromethyl)phenyl]methanone

Obtained as a bright yellow solid (58%) from the title compound of Preparation 42d following the experimental procedure described in Preparation 1f.

f) [3-Amino-2-(2,6-difluorophenyl)pyridin-4-yl][4-(trifluoromethyl)phenyl]methanone Obtained as a yellow solid (68%) from the title compound of Preparation 42e following the experimental procedure of Preparation 5.
LRMS (m/z): 379 (M+1)$^+$.
$^1$H-NMR δ (CDCl$_3$): 6.03 (brs, 2H), 7.06-7.14 (m, 2H), 7.29 (d, J=4 Hz, 1H), 7.40-7.55 (m, 1H), 7.77-7.87 (m, 4H), 8.10 (d, J=4 Hz, 1H).

g) [3-Amino-2-(2,6-difluorophenyl)-1-oxidopyridin-4-yl][4-(trifluoromethyl)phenyl]-methanol Obtained as a yellow solid (80%) from the title compound of Preparation 42f following the experimental procedure of Preparation 11.
LRMS (m/z): 395 (M+1)$^+$.
$^1$H-NMR δ (CDCl$_3$): 6.44 (brs, 2H), 7.10-7.18 (m, 2H), 7.36 (d, J=8 Hz, 1H), 7.49-7.64 (m, 1H), 7.68 (d, J=8 Hz, 1H), 7.74-7.84 (m, 4H).

Preparation 43

[3-Amino-2-(2,6-dichlorophenyl)-1-oxidopyridin-4-yl][4-(trifluoromethyl)phenyl]-methanone a) [3-Amino-2-(2,6-dichlorophenyl)pyridin-4-yl][4-(trifluoromethyl)phenyl]methanone Obtained as a yellow solid (34%) from the title compound of Preparation 42e and 2,6-dichlorophenylboronic acid following the experimental procedure described in Preparation 6.
LRMS (m/z): 411, 413, 415 (M+1)$^+$.
$^1$H-NMR δ (CDCl$_3$): 5.92 (brs, 2H), 7.30 (d, J=6 Hz, 1H), 7.34-7.53 (m, 3H), 7.77-7.87 (m, 4H), 8.11 (d, J=6 Hz, 1H).

b) [3-Amino-2-(2,6-dichlorophenyl)-1-oxidopyridin-4-yl][4-(trifluoromethyl)phenyl]-methanone Obtained as a yellow solid (78%) from the title compound of Preparation 43a following the experimental procedure of Preparation 11.
LRMS (m/z): 427, 429, 431 (M+1)$^+$.

$^1$H-NMR δ (CDCl$_3$): 6.32 (brs, 2H), 7.37 (d, J=6 Hz, 1H), 7.41-7.58 (m, 3H), 7.67 (d, J=6 Hz, 1H), 7.75-7.84 (m, 4H).

Preparation 44

2-Chloro-8-(2,6-dichlorophenyl)-4-(2,4-difluorophenyl)-1,7-naphthyridine a) N-[2-(2,6-Dichlorophenyl)-4-(2,4-difluorobenzoyl)pyridin-3-yl]-2,2-dimethylpropanamide To a solution of the title compound of Preparation 10 (0.5 g, 1.31 mmol) and diisopropylethylamine 0.345 mL, 1.97 mmol) in 5 mL of dioxane under argon, was carefully added pivaloyl chloride (0.226 mL, 1.83 mmol) in 2 mL of dioxane. After the addition was completed, the reaction mixture was stirred at 110° C. for 18 hours. The mixture was diluted with ethyl acetate, washed with water, aqueous 4% sodium bicarbonate, brine, dried over sodium sulphate and the solvent removed under reduced pressure. The residue was purified by column chromatography on silica flash, using hexane/diethylether (0 to 100% of diethylether) as eluents, to yield the title compound (0.447 g, 73%) as a white solid.

b) 3-[2-(2,6-Dichlorophenyl)-3-(2,2-dimethylpropionylamino)-pyridin-4-yl]-3-(2,4-difluorophenyl)-3-hydroxypropionic acid tert-butyl ester nBuLi (1.6M in hexanes, 1.8 mL, 3.02 mmol) was dropwise added to a solution of diisopropylamine in dry tetrahydrofuran (2.1 mL) at −78° C. under argon and the resulting mixture was stirred at room temperature for 20 minutes. Then, the reaction mixture was cooled down to −78° C. and tert-butylacetate (0.350 g, 3.02 mmol) in dry tetrahydrofuran (1 mL) was added. Afterwards, the title compound of Preparation 44a (0.350 g, 0.75 mmol) in dry tetrahydrofuran (2 mL) was added and the mixture stirred overnight at room temperature. Subsequently, the solvent was removed under reduced pressure and the residue was partitioned between ethyl acetate (50 mL) and water (50 mL). The organic solution was washed with brine, dried over anhydrous sodium sulphate and the solvent removed under reduced pressure to yield the title compound (0.435 g, 100%) as a solid.

c) 8-(2,6-Dichlorophenyl)-4-(2,4-difluorophenyl)-1,7-naphthyridin-2(1H)-one

A mixture of the title compound of Preparation 44b (5.97 g, 9.29 mmol) and HCl (63 mL, 5M) was stirred at 100° C. overnight. The reaction was carefully neutralised with a saturated solution of potassium carbonate in water and the precipitated solid was filtered to yield the title compound (3.4 g, 90%) as a solid.

d) 2-Chloro-8-(2,6-dichlorophenyl)-4-(2,4-difluorophenyl)-1,7-naphthyridine

A mixture of the title compound of Preparation 44c (0.3 g, 0.74 mmol) and phosphorus oxychloride (2.22 mL) was heated at 110° C. in a sealed tube for 2 h. The reaction was cooled down, poured into ice water and the pH adjusted to 10-11 with concentrated aqueous ammonia. The solution was extracted with ethyl acetate (2×50 mL), the organic layer was washed with brine, dried over sodium sulphate and the solvent removed under reduced pressure to yield the title compound (311.95 g, 100%) as a solid.

¹H-NMR δ (CDCl₃): 7.06-7.17 (m, 2H), 7.36-7.43 (m, 1H), 7.45-7.55-7.58 (m, 2H), 8.76 (dd, J=2.75 and 5.75 Hz, 1H).

Preparation 45

2-Chloro-4-(2,4-difluorophenyl)-8-(2,6-difluorophenyl)-1,7-naphthyridine a) N-[4-(2,4-Difluorobenzyl)-2-(2,6-difluorophenyl)pyridin-3-yl]-2,2-dimethylpropanamide Obtained as a white solid (82%) from the title compound of Preparation 5 following the experimental procedure described in Preparation 44a.

b) 3-(2,4-Difluorophenyl)-3-[2-(2,6-difluorophenyl)-3-(2,2-dimethylpropionylamino)-pyridin-4-yl]-3-hydroxypropionic acid tert-butyl ester Obtained as a pale yellow solid (100%) from the title compound of Preparation 45a following the experimental procedure described in Preparation 44b.

c) 4-(2,4-difluorophenyl)-8-(2,6-difluorophenyl)-1,7-naphthyridin-2(1H)-one

Obtained as a white solid (88%) from the title compound of Preparation 45b following the experimental procedure described in Preparation 44c.

d) 2-Chloro-4-(2,4-difluorophenyl)-8-(2,6-difluorophenyl)-1,7-naphthyridine

Obtained as a white solid (91%) from the title compound of Preparation 45c following the experimental procedure described in Preparation 44d.
¹H-NMR δ (CDCl₃): 7.06-7.13 (m, 4H), 7.40-7.51 (m, 2H), 7.55-7.58 (m, 2H), 8.76 (d, J=5.77 Hz, 1H).

Preparation 46

2-Chloro-8-(2-chlorophenyl)-4-(2,4-difluorophenyl)-1,7-naphthyridine a) N-[2-(2-Chlorophenyl)-4-(2,4-difluorobenzoyl)pyridin-3-yl]-2,2-dimethylpropanamide Obtained as a pale yellow solid (98%) from the title compound of Preparation 8 following the experimental procedure described in Preparation 44a.

b) 3-[2-(2-Chlorophenyl)-3-(2,2-dimethylpropionylamino)pyridin-4-yl]-3-(2,4-difluorophenyl)-3-hydroxypropionic acid tert-butyl ester Obtained as a pale yellow solid (43%) from the title compound of Preparation 46a following the experimental procedure described in Preparation 44b.

c) 8-(2-Chlorophenyl)-4-(2,4-difluorophenyl)-1,7-naphthyridin-2(1H)-one

Obtained as a pale yellow solid (71%) from the title compound of Preparation 46b following the experimental procedure described in Preparation 44c.

d) 2-Chloro-8-(2-chlorophenyl)-4-(2,4-difluorophenyl)-1,7-naphthyridine

Obtained as a white solid (86%) from the title compound of Preparation 46c following the experimental procedure described in Preparation 44d.
¹H-NMR δ (CDCl₃): 7.06-7.16 (m, 2H), 7.42-7.47 (m, 3H), 7.51-7.57 (m, 4H), 8.71 (dd, J=1.24 and 5.81 Hz, 1H).

Preparation 47

2-Chloro-4-(2,4-difluorophenyl)-8-(2-methylphenyl)-1,7-naphthyridine a) N-[4-(2,4-Difluorobenzyl)-2-(2-methylphenyl)-3-yl]-2,2-dimethylpropionamide Obtained as a yellow solid (89%) from the title compound of Preparation 1 following the experimental procedure described in Preparation 44a.

b) 3-(2,4-Difluorophenyl)-3-[3-(2,2-dimethylpropionylamino)-2-(2-methylphenyl)pyridin-4-yl]-3-hydroxypropionic acid tert-butyl ester Obtained as a yellow solid (100%) from the title compound of Preparation 47a following the experimental procedure described in Preparation 44b.

c) 4-(2,4-Difluorophenyl)-8-(2-methylphenyl)-1,7-naphthyridin-2(1H)-one

Obtained as a beige solid (88%) from the title compound of Preparation 47b following the experimental procedure described in Preparation 44c.

d) 2-Chloro-4-(2,4-difluorophenyl)-8-(2-methylphenyl)-1,7-naphthyridine

Obtained as a white solid (100%) from the title compound of Preparation 47c following the experimental procedure described in Preparation 44d.
¹H-NMR δ (CDCl₃): 2.20 (s, 3H) 7.06-7.17 (m, 2H) 7.34-7.50 (m, 6H) 7.54 (s, 1H) 8.71 (d, J=5.77 Hz, 1H).

Preparation 48

2-Chloro-8-(2,6-dichlorophenyl)-4-(2,4-difluorophenyl)-1,7-naphthyridine 7-oxide a) 8-(2,6-dichlorophenyl)-4-(2,4-difluorophenyl)-1,7-naphthyridin-2(1H)-one 7-oxide To an ice cooled solution of the title compound of Preparation 44c (3.1 g, 7.69 mmol) in 58 mL of dichloromethane under nitrogen, was added meta-chloroperbenzoic acid (2.57 g, 11.53 mmol). After the addition was completed, the reaction mixture was stirred at room temperature for 16 hours. The mixture was diluted with dichloromethane (50 mL), washed with a saturated solution of sodium bicarbonate, dried over sodium sulphate and the solvent removed under reduced pressure to yield the title compound (2.77 g, 86%) as a solid.

b) 2-Chloro-8-(2,6-dichlorophenyl)-4-(2,4-difluorophenyl)-1,7-naphthyridine 7-oxide A mixture of the title compound of Preparation 48a (2:67 g, 6.36 mmol) and phosphorus oxychloride (27 mL) was heated at 110° C. in a sealed tube for 2 h. The reaction was cooled down, poured into ice water and the pH adjusted to 10-11 with concentrated aqueous ammonia. The solution was extracted with ethyl acetate (2×100 mL), the organic layer was washed with brine, dried over sodium sulphate and the solvent removed under reduced pressure. The residue was crystallised with isopropanol to yield the title compound (1.71 g, 62%) as a yellow solid.

$^1$H-NMR δ (CDCl$_3$): 7.06-7.17 (m, 2H), 7.38 (s, 1H), 7.41-7.55 (m, 5H), 8.32 (d, J=7.4 Hz, 1H).

Preparation 49

2-Chloro-4-(2,4-difluorophenyl)-8-(2,6-difluorophenyl)-1,7-naphthyridine 7-oxide a) 4-(2,4-difluorophenyl)-8-(2,6-difluorophenyl)-1,7-naphthyridin-2(1H)-one 7-oxide A mixture of the title compound of Preparation 45c (0.3 g, 0.81 mmol), acetic acid (8 mL) and hydrogen peroxide (27 mL) was heated at 95° C. in a sealed tube for 16 h. The reaction mixture was diluted with water (50 mL) and extracted with ethyl acetate (3×40 mL). The organic layer was dried over sodium sulphate and the solvent removed under reduced pressure to yield the title compound (0.289 g, 85%) as a solid.

b) 2-Chloro-4-(2,4-difluorophenyl)-8-(2,6-difluorophenyl)-1,7-naphthyridine 7-oxide Obtained as a solid (62%) from the title compound of Preparation 49a following the experimental procedure described in Preparation 48b. (Reaction time: 1 h)

$^1$H-NMR δ (DMSO-d$_6$): 7.34-7.48 (m, 3H), 7.63-7.83 (m, 4H), 7.86 (s, 1H), 8.54 (d, J=7.4 Hz, 1H).

Preparation 50

2-Chloro-8-(2-chlorophenyl)-4-(2,4-difluorophenyl)-1,7-naphthyridine 7-oxide a) 8-(2-Chlorophenyl)-4-(2,4-difluorophenyl)-1,7-naphthyridin-2(1H)-one 7-oxide Obtained as a solid (84%) from the title compound of Preparation 46c following the experimental procedure described in Preparation 48a.

b) 2-Chloro-8-(2-chlorophenyl)-4-(2,4-difluorophenyl)-1,7-naphthyridine 7-oxide

Obtained as a solid (34%) from the title compound of Preparation 50a following the experimental procedure described in Preparation 48b. (Reaction time: 1 h)

$^1$H-NMR δ (CDCl$_3$): 7.07-7.16 (m, 2H), 7.37 (d, J=1.7 Hz, 1H), 7.42-7.53 (m, 5H), 7.61 (d, J=7.0 Hz, 1H), 8.32 (dd, J=7.5, 2.1 Hz, 1H).

Preparation 51

2-Chloro-4-(2,4-difluorophenyl)-8-(2-methylphenyl)-1,7-naphthyridine 7-oxide a) 4-(2,4-Difluorophenyl)-8-(2-methylphenyl)-1,7-naphthyridin-2(1H)-one 7-oxide Obtained as a yellow solid (96%) from the title compound of Preparation 47c following the experimental procedure described in Preparation 48a.

b) 2-Chloro-4-(2,4-difluorophenyl)-8-(2-methylphenyl)-1,7-naphthyridine 7-oxide

Obtained as a brown oil (99%) from the title compound of Preparation 51a following the experimental procedure described in Preparation 48b. (Reaction time: 1 h)

$^1$H-NMR δ (CDCl$_3$): 2.17 (s, 3H), 7.05-7.16 (m, 2H), 7.31-7.48 (m, 7H), 8.33 (d, J=7.4 Hz, 1H).

Preparation 52

3-Methyl-4-(4,4,5,5-tetramethyl-[1,3,2]dioxaborolan-2-yl)-phenol

In a Schlenk tube a mixture of 4-bromo-3-methylphenol (805 mg, 4.23 mmol), 4,4,5,5,4',4',5',5'-Octamethyl-[2,2]bi[[1,3,2]dioxaborolanyl] (1.64 g, 6.45 mmol), [1,1'-bis(diphenyl-phosphino)ferrocene]dichloropalladium(II) complex with dichloromethane (1:1) (344 mg, 0.42 mmol) and potassium acetate (2.1 g, 21 mmol) in N,N-dimethyl formamide (15 mL) was heated at 80° C. for 18 hours. The cooled mixture was diluted with ethyl acetate, washed with water, brine and dried over sodium sulphate. The solvent was removed under reduced pressure and the residue was purified by column chromatography on silica flash, using hexane/ethyl acetate (7:1) as eluents, to yield the title compound (617 mg, 63%) as a white solid.

$^1$H-NMR δ (CDCl$_3$): 1.32 (s, 12H), 2.49 (s, 3H), 6.62-6.64 (m, 2H), 7.64-7.69 (d, J=10H, 1H).

Preparation 53

1,3-Benzodioxole-4-boronic acid nBuLi (2.5M in hexanes, 2.38 mL, 5.97 mmol) was dropwise added to a solution of 4-bromo-1,3-benzodioxole (1 g, 4.97 mmol) and triisopropyl borate (1.49 mL, 6.47 mmol) in 50 mL of dry tetrahydrofuran at −78° C. under argon. The reaction was maintained at that temperature for 3 hours, then warmed up to room temperature and cooled back to 0° C. immediately. The solution was acidified to pH=2 with HCl 2N and neutralized to pH=7 with NaOH 2N, it was then extracted with ethyl acetate (3×25 ml), the organic solution was washed with brine, dried over sodium sulphate and the solvent removed under reduced pressure to yield the title compound (570 mg, 69%) as a white solid.

$^1$H-NMR δ (CD$_3$OD): 5.92 (s, 2H), 6.80-6.86 (m, 3H).

Preparation 54

N-(4-(4,4,5,5-Tetramethyl-[1,3,2]dioxaborolan-2-yl)-3-methylphenyl)methanesulfonamide a) (4-Bromo-3-methylphenyl)amine Activated Raney Nickel® (0.4 g) was added to a suspension of 1-bromo-2-methyl-4-nitrobenzene (4 g, 18.51 mmol)

in 200 mL of methanol and the mixture was stirred under hydrogen atmosphere (30 psi) for 3 hours. After this time, the reaction mixture was filtered through Celite®, the solvent eliminated under reduced pressure and the residue dried under vacuum to afford the title compound (3.4 g, 99%) as a white solid.

$^1$H-NMR δ (CDCl$_3$): 2.28 (s, 3H), 3.39 (brs, 2H), 6.38 (d, J=8 Hz, 1H), 6.55 (s, 1H), 7.27 (d, J=8 Hz, 1H).

b)
N-(4-Bromo-3-methylphenyl)methanesulfonamide

Methanesulfonyl chloride (2.64 g, 20.96 mmol) was dropwise added to a solution of the title compound of Preparation 54a (3.25 g, 17.47 mmol) in 87 mL of piridine and the reaction mixture was stirred at room temperature for 18 hours. The solvent was evaporated and the residue partitioned between ethyl acetate (250 mL) and 5% citric acid (125 mL). The organic layer was washed again with 5% citric acid, dried over sodium sulphate and the solvent evaporated under reduced pressure to give a residue which was purified by column chromatography on silica flash, using dichloromethane as eluent (isocratic), to yield the title compound (3.7 g, 80%).

$^1$H-NMR δ (CDCl$_3$): 2.38 (s, 3H), 3.02 (s, 3H), 6.97 (dd, J=2 and 8 Hz, 1H), 7.03 (brs, 1H), 7.12 (d, J=2 Hz, 1H), 7.49 (d, J=8 Hz, 1H).

c) N-(4-(4,4,5,5-Tetramethyl-[1,3,2]dioxaborolan-2-yl-3-methylphenyl)methanesulfonamide In a Schlenk tube a mixture of the title compound of Preparation 54b (3.7 g, 14 mmol), 4,4,5,5,4',4',5',5'-Octamethyl-[2,2']bi[[1,3,2]dioxaborolanyl] (5.33 g, [1,1'-bis(diphenylphosphino)ferrocene]dichloropalladium(II) complex with dichloromethane (1:1) (114 mg, 0.14 mmol) and potassium acetate (6.86 g, 70 mmol) in N,N-dimethyl formamide (48 mL) was heated at 80° C. for 18 hours. The cooled mixture was diluted with ethyl acetate, washed with water, brine and dried over sodium sulphate. The solvent was removed under reduced pressure and the residue was purified by column chromatography on silica flash, using dichloromethane/ethyl acetate (1:3) as eluents, to yield the title compound (1.9 g, 43%) as a white solid.

$^1$H-NMR δ (CDCl$_3$): 1.34 (s, 12H), 2.53 (s, 3H), 3.02 (s, 3H), 6.75 (brs, 1H), 6.99 (s, 1H), 7.01 (d, J=8 Hz, 1H), 7.74 (d, J=8 Hz, 1H).

Preparation 55

Tert-butyl 4-acetylpiperidine-1-carboxylate a) Tert-butyl 4-{[methoxy(methyl)amino]carbonyl}piperidine-1-carboxylate To a solution of N,O-dimethylhydroxylamine hydrochloride (894 mg, 9.17 mmol), 2-benzotriazol-1-yl-N,N,N',N'-tetramethyluronio hexafluorphosphate (HBTU) (3.48 g, 9.17 mmol) and diisopropylethylamine (DIPEA) in N,N-dimethylformamide (40 mL) was carefully added 1-(tert-butoxycarbonyl)piperidine-4-carboxylic acid (2 g, 8.73 mmol) and the reaction mixture was stirred at room temperature for 2 days. The mixture was diluted with water (200 mL), extracted with ethyl acetate, washed with aqueous citric acid 5%, aqueous sodium bicarbonate 4%, water, and brine and dried over sodium sulphate. The solvent was removed under reduced pressure and the residue was purified by column chromatography on silica flash, using ethyl acetate as eluent (isocratic), to yield the title compound (2.63 g, 99%) as yellowish oil.

$^1$H-NMR δ (CDCl$_3$): 1.46 (s, 9H), 1.63-1.74 (m, 4H), 2.70-2.84 (m, 3H), 3.19 (s, 3H), 3.72 (s, 3H), 4.11-4.18 (m, 2H).

b) Tert-butyl 4-acetylpiperidine-1-carboxylate

Methyl magnesium bromide (3M in dietyhl ether, 2.45 mL, 7.35 mmol) was dropwise added to an ice-cooled solution of the title compound of Preparation 55a (1 g, 3.67 mmol) under argon and the mixture was stirred at that temperature for 18 hours. The reaction was quenched by the addition of ice and vigorously stirred for 30 minutes. The mixture was extracted with ethyl acetate, washed with brine and dried over sodium sulphate. The solvent was removed under reduced pressure and the residue was purified by column chromatography on silica flash, using hexane/ethyl acetate (1:1) as eluents, to yield the title compound (680 mg, 82%) as colourless oil.

$^1$H-NMR δ (CDCl$_3$): 1.46 (s, 9H), 1.41-1.62 (m, 2H), 1.78-1.88 (m, 2H), 2.17 (m, 3H), 2.38-2.54 (m, 1H), 2.71-2.86 (m, 2H), 4.05-4.15 (m, 2H).

Preparation 56

1-(1-Tert-butylpiperidin-4-yl)ethanone a) 1-Tert-butylpiperidine-4-carbonitrile

1-Tert-butylpiperidin-4-one (Amato, J. S.; Chung, J. Y. L.; Cvetovich, R. J.; Gong, X.; McLaughlin, M. and Reamer, R. A. *J. Org. Chem.* 2005, 70, 1930) (500 mg, 3.22 mmol) was added to a solution of para-toluenesulfonylmethyl isocyanide (TOSMIC) (1.13 g, 5.80 mmol) in 1,2-dimethoxyethane (20 mL) and the mixture was stirred under argon at room temperature for 10 min. The mixture was cooled with an ice-water bath and then absolute ethanol (0.46 mL) was added. Potassium Pert-butoxide 95% (1.32 g, 11.2 mmol) was portionwise added and the reaction mixture stirred under argon at 0-5° C. for 1 h, at room temperature for 3 h and at 40° C. for 3 additional hours. The reaction was diluted with water (100 mL), neutralised with HCl 2N, rebasified to pH=10 with NaOH 2N and extracted with ethyl acetate (3×80 mL). The combined organic phases were washed with brine and dried over anhydrous sodium sulphate. Evaporation of the solvent under reduced pressure gave 680 mg of brownish oil. The crude oil was purified by Flash chromatography on SP1 system from Biotage®, using dichloromethane/methanol/NH$_4$OH (95:5:0.5) as eluents. An oily residue was isolated (220 mg, 34%) and identified by $^1$H NMR as final product.

$^1$H-NMR δ (DMSO-d$_6$): 1.12 (s, 9H), 1.71-1.81 (m, 2H), 1.90-2.00 (m, 2H), 2.40-2.50 (m, 2H), 2.75-2.80 (m, 2H), 2.93 (m, 1H).

b) 1-(1-Tert-butylpiperidin-4-yl)ethanone

Methyl magnesium bromide (3M in dietyhl ether, 1.45 mL, 4.35 mmol) was dropwise added to an ice-cooled solution of the title compound of Preparation 56a (174 mg, 1.048 mmol) in tetrahydrofuran (4 mL) under argon and the mixture was stirred at that temperature for 18 hours. The reaction was quenched by the addition of ice and vigorously stirred for 30 minutes, it was acidified with HCl 2N (pH=2), rebasified to pH=10 with NaOH 2N and extracted with ethyl acetate (3×80 mL). The combined organic phases were washed with brine and dried over anhydrous sodium sulphate. Evaporation of the solvent under reduced pressure gave 118 mg of brownish oil. The crude oil was purified by Flash chromatography on SP1 system from Biotage®, using dichloromethane/methanol/NH$_4$OH (95:5:0.5) as eluents, to yield the title compound (91 mg, 43%) as a brownish oil.

$^1$H-NMR δ (CDCl$_3$): 1.12 (s, 9H), 1.62-1.75 (m, 2H), 1.89-1.96 (m, 2H), 2.13-2.21 (m, 2H), 2.19 (s, 3H), 2.30 (m, 1H), 3.08-3.14 (m, 2H).

EXAMPLES

Example 1

4-(2,4-Difluorophenyl)-8-(2-methylphenyl)-1,7-naphthyridine

To a solution of the title compound of Preparation 1 (20 mg, 0.062 mmol) in 0.4 mL of glacial acetic acid was added acetaldehyde (0.3 mL) and the mixture was heated in a microwave system ("Initiator sixty" from Biotage®) at 100° C. for 45 minutes. The cooled reaction was poured into water (50 mL) and the pH adjusted to 6-7 using 2M NaOH. The solution was extracted with ethyl acetate (3×25 mL). The combined organic layers were washed with brine, dried over sodium sulphate and the solvent removed under reduced pressure. The residue was purified by column chromatography on silica flash, using hexane/ethyl acetate (8:2) as eluents, to yield the title compound (12 mg, 56%) as a white solid.

LRMS (m/z): 333 (M+1)$^+$.

Retention Time: 17 min.

$^1$H-NMR δ (CDCl$_3$): 2.15 (s, 3H), 7.03-7.17 (m, 2H), 7.33-7.54 (m, 7H), 8.67 (d, J=6 Hz, 1H), 9.04 (d, J=4 Hz, 1H).

Example 2

4-(2,4-Difluorophenyl)-8-(2-methoxyphenyl)-1,7-naphthyridine

Obtained as an off-white solid (61%) from the title compound of Preparation 2 following the experimental procedure of Example 1.

LRMS (m/z): 349 (M+1)$^+$.

Retention Time: 15 min.

$^1$H-NMR δ (CDCl$_3$): 3.74 (s, 3H), 7.02-7.18 (m, 4H), 7.40-7.52 (m, 5H), 8.67 (d, J=6 Hz, 1H), 9.03 (d, J=4 Hz, 1H).

Example 3

4-[4-(2,4-Difluorophenyl)-1,7-naphthyridin-8-yl]-3-methylphenol

Obtained as an off-white solid (99%) from the title compound of Preparation 3 following the experimental procedure of Example 1.

LRMS (m/z): 349 (M+1)$^+$.

Retention Time: 15 min.

$^1$H-NMR δ (CDCl$_3$): 2.10 (s, 3H), 6.70-6.76 (m, 2H), 7.03-7.17 (m, 2H), 7.27-7.54 (m, 3H), 7.55 (d, J=4 Hz, 1H), 8.66 (d, J=6 Hz, 1H), 9.07 (d, J=4 Hz, 1H).

Example 4

8-(1,3-Benzodioxol-4-yl)-4-(2,4-difluorophenyl)-1,7-naphthyridine

Obtained as an off-white solid (59%) from the title compound of Preparation 4 following the experimental procedure of Example 1.

LRMS (m/z): 363 (M+1)$^+$.

Retention Time: 15 min.

$^1$H-NMR δ (CDCl$_3$): 6.03 (s, 2H), 6.96-7.16 (m, 4H), 7.27-7.43 (m, 2H), 7.51 (dd, J=2 and 4 Hz, 1H), 7.56 (d, J=6 Hz, 1H), 8.71 (d, J=6 Hz, 1H), 9.09 (d, J=4 Hz, 1H).

Example 5

4-(2,4-Difluorophenyl)-8-(2,6-difluorophenyl)-1,7-naphthyridine

Obtained as an off-white solid (20%) from the title compound of Preparation 5 following the experimental procedure of Example 1.

LRMS (m/z): 355 (M+1)$^+$.

Retention Time: 15 min.

$^1$H-NMR δ (CDCl$_3$): 7.03-7.16 (m, 4H), 7.38-7.52 (m, 2H), 7.55-7.62 (m, 2H), 8.74 (d, J=6 Hz, 1H), 9.05 (d, J=4 Hz, 1H).

Example 6

4-(2,4-Difluorophenyl)-8-[4-(2-methoxyethoxy)-2-methylphenyl]-1,7-naphthyridine

To a solution of the title compound of Example 3 (57 mg, 0.16 mmol) in 1.5 mL of acetonitrile were added 1-chloro-2-methoxyethane (22.6 mg, 0.24 mmol) and potassium carbonate (86 mg, 0.62 mmol) and the mixture was heated at 80° C. for 12 hours. The solvent was removed under reduced pressure and the residue purified by column chromatography (C-18 silica from Waters©, reverse phase water/acetonitrile as eluents [0.1% v/v formic acid buffered] 0% to 60%) to give the title compound as an off-white solid (9 mg, 9% yield).

LRMS (m/z): 407 (M+1)$^+$.

Retention Time: 15 min.

$^1$H-NMR δ (CDCl$_3$): 2.16 (s, 3H), 3.48 (s, 3H), 3.77-3.82 (m, 2H), 4.18-4.23 (m, 2H), 6.89-7.16 (m, 4H), 7.28-7.41 (m, 2H), 7.48 (dd, J=2 and 4 Hz, 1H), 7.52 (d, J=4 Hz, 1H), 8.66 (d, J=6 Hz, 1H), 9.05 (d, J=4 Hz, 1H).

Example 7

4-(2,4-Difluorophenyl)-8-[2-methyl-4-(2-morpholin-4-ylethoxy)phenyl]-1,7-naphthyridine To a solution of the title compound of Example 3 (57 mg, 0.16 mmol) in 1.5 mL of acetonitrile were added 4-(2-chloroethyl)morpholine hydrochloride (45 mg, 0.24 mmol) and potassium carbonate (89 mg, 0.62 mmol) and the mixture was heated at 80° C. for 12 hours. The solvent was removed under reduced pressure and the residue purified by column chromatography (C-18 silica from Waters©, reverse phase water/acetonitrile as eluents [0.1% v/v formic acid buffered] 0% to 60%) to give the title compound as an off-white solid (17 mg, 23% yield).

LRMS (m/z): 462 (M+1)$^+$.

Retention Time: 10 min.

$^1$H-NMR δ (CDCl$_3$): 2.15 (s, 3H), 2.60-2.72 (m, 4H), 2.85-2.93 (m, 2H), 3.71-3.84 (m, 4H), 4.19-4.27 (m, 2H), 6.88-7.10 (m, 4H), 7.28-7.41 (m, 2H), 7.48 (dd, J=2 and 4 Hz, 1H), 7.52 (d, J=4 Hz, 1H), 8.65 (d, J=6 Hz, 1H), 9.05 (d, J=4 Hz, 1H).

Example 8

4-(2,4-Difluorophenyl)-8-(2,6-dimethylphenyl)-1,7-naphthyridine

Obtained as an off-white solid (66%) from the title compound of Preparation 6 following the experimental procedure of Example 1.
LRMS (m/z): 347 (M+1)$^+$.
Retention Time: 17 min.
$^1$H-NMR δ (CDCl$_3$): 1.95 (s, 6H), 7.05-7.33 (m, 4H), 7.40-7.54 (m, 4H), 8.70 (d, J=6 Hz, 1H), 9.02 (d, J=4 Hz, 1H).

Example 9

4-(2,4-Difluorophenyl)-8-(2,6-dimethoxyphenyl)-1,7-naphthyridine

Obtained as an off-white solid (47%) from the title compound of Preparation 7 following the experimental procedure of Example 1.
LRMS (m/z): 379 (M+1)$^+$.
Retention Time: 14 min.
$^1$H-NMR δ (CDCl$_3$): 3.68 (s, 6H), 6.75 (d, J=8 Hz, 2H), 7.02-7.14 (m, 2H), 7.38-7.52 (m, 3H), 7.41 (d, J=8 Hz, 1H), 8.70 (d, J=6 Hz, 1H), 9.01 (d, J=4 Hz, 1H).

Example 10

4-(2,4-Difluorophenyl)-8-(2-methylphenyl)-2-piperidin-4-yl-1,7-naphthyridine

Sulfuric acid 98% (0.47 mL) was dropwise added to a suspension of the title compound of Preparation 1 (470 mg, 1.45 mmol), anhydrous magnesium sulphate (940 mg) and the title compound of Preparation 55 (725 mg, 3.19 mmol) in 15 mL of toluene and the mixture was vigorously stirred in a pre-heated oil bath at 115° C. After 60 minutes, the reaction was cooled down and the solvent discarded. The residue was washed with ethyl acetate, dissolved in methanol and filtered through a sintered glass to eliminate most of the inorganic salts. The solvent was removed under reduced pressure and the oily material purified by column chromatography (C-18 silica from Waters©, reverse phase water/acetonitrile as eluents [0.1% v/v formic acid buffered] 0% to 30%). The acetonitrile from the appropriate fractions was evaporated and the aqueous phase basified to pH=10. It was extracted with ethyl acetate, dried over sodium sulphate and the solvent removed under reduced pressure to give the title compound as an off-white solid (542 mg, 90% yield).
LRMS (m/z): 416 (M+1)$^+$.
Retention Time: 11 min.
$^1$H-NMR δ (DMSO-d$_6$): 1.47-1.60 (m, 2H), 1.72-1.79 (m, 2H), 2.05 (s, 3H), 2.47-2.58 (m, 2H), 2.88-3.00 (m, 3H), 7.25-7.40 (m, 5H), 7.45 (dd, J=2 and 4 Hz, 1H), 7.50-7.74 (m, 3H), 8.59 (d, J=6 Hz, 1H).

Example 11

8-(2-Chlorophenyl)-4-(2,4-difluorophenyl)-2-piperidin-4-yl-1,7-naphthyridine

Obtained as an off-white solid (84%) from the title compound of Preparation 8 following the experimental procedure of Example 10.
LRMS (m/z): 436, 438 (M+1)$^+$.
Retention Time: 14 min.
$^1$H-NMR δ (DMSO-d$_6$): 1.45-1.60 (m, 2H), 1.70-1.80 (m, 2H), 2.45-2.58 (m, 2H), 2.85-3.00 (m, 3H), 7.28-7.40 (m, 1H), 7.45-7.65 (m, 6H), 7.66-7.75 (m, 2H), 8.60 (d, J=6 Hz, 1H).

Example 12

4-(2,4-Difluorophenyl)-8-(2-fluorophenyl)-2-piperidin-4-yl-1,7-naphthyridine

Obtained as an off-white solid (97%) from the title compound of Preparation 9 following the experimental procedure of Example 10.
LRMS (m/z): 420 (M+1)$^+$.
Retention Time: 11 min.
$^1$H-NMR δ (DMSO-d$_6$): 1.45-1.64 (m, 2H), 1.72-1.82 (m, 2H), 2.48-2.60 (m, 2H), 2.85-3.00 (m, 3H), 7.28-7.40 (m, 3H), 7.50 (dd, J=4 and 6 Hz, 1H), 7.53-7.74 (m, 5H), 8.62 (d, J=6 Hz, 1H).

Example 13

4-(2,4-Difluorophenyl)-8-(2,6-difluorophenyl)-2-piperidin-4-yl-1,7-naphthyridine Obtained as an off-white solid (82%) from the title compound of Preparation 5 following the experimental procedure of Example 10.
LRMS (m/z): 438 (M+1)$^+$.
Retention Time: 11 min.
$^1$H-NMR δ (DMSO-d$_6$): 1.45-1.62 (m, 2H), 1.72-1.82 (m, 2H), 2.45-2.60 (m, 2H), 2.85-3.00 (m, 3H), 7.22-7.40 (m, 3H), 7.51-7.77 (m, 5H), 8.66 (d, J=6 Hz, 1H).

Example 14

8-(2,6-Dichlorophenyl)-4-(2,4-difluorophenyl)-2-piperidin-4-yl-1,7-naphthyridine Obtained as an off-white solid (40%) from the title compound of Preparation 10 following the experimental procedure of Example 10.
LRMS (m/z): 470, 472, 474 (M+1)$^+$.
Retention Time: 12 min.
$^1$H-NMR δ (CDCl$_3$): 1.65-2.20 (m, 4H), 2.70-3.25 (m, 5H), 7.00-7.15 (m, 2H), 7.35-7.60 (m, 6H), 8.67 (d, J=6 Hz, 1H).

Example 15

4-(2,4-Difluorophenyl)-8-(2-methylphenyl)-1,7-naphthyridine 7-oxide

To a solution of the title compound of Preparation 11 (500 mg, 1.47 mmol) in 2 mL of glacial acetic acid was added acetaldehyde (2 mL) and the mixture was heated in a microwave system ("Initiator sixty" from Biotage®) at 110° C. for 18 hours. The cooled reaction was poured into water (50 mL) and the pH adjusted to 6-7 using 2M NaOH. The solution was extracted with ethyl acetate (3×25 mL). The combined organic layers were washed with brine, dried over sodium sulphate and the solvent removed under reduced pressure. The residue was purified by column chromatography on silica flash, using hexane/ethyl acetate (3:7) as eluents, to yield the title compound (232 mg, 45%) as a white solid.

LRMS (m/z): 349 (M+1)+.
Retention Time: 14 min.
¹H-NMR δ (CDCl₃): 2.18 (s, 3H), 7.03-7.18 (m, 2H), 7.30-7.54 (m, 7H), 8.33 (d, J=8 Hz, 1H), 8.96 (d, J=6 Hz, 1H).

Example 16

4-(2,4-Difluorophenyl)-8-(2-methoxyphenyl)-1,7-naphthyridine 7-oxide

Obtained as an off-white solid (55%) from the title compound of Preparation 12 following the experimental procedure of Example 15.
LRMS (m/z): 365 (M+1)+.
Retention Time: 13 min.
¹H-NMR δ (CDCl₃): 3.80 (s, 3H), 7.02-7.21 (m, 4H), 7.33-7.59 (m, 5H), 8.32 (d, J=8 Hz, 1H), 8.96 (d, J=4 Hz, 1H).

Example 17

4-[4-(2,4-Difluorophenyl)-7-oxido-1,7-naphthyridin-8-yl]-3-methylphenol

Obtained as an off-white solid (32%) from the title compound of Preparation 13 following the experimental procedure of Example 15.
LRMS (m/z): 365 (M+1)+.
Retention Time: 12 min.
¹H-NMR δ (CDCl₃): 2.09 (s, 3H), 6.64-6.69 (m, 2H), 7.04-7.16 (m, 3H), 7.38-7.44 (m, 2H), 7.54 (dd, J=2 and 8 Hz, 1H), 8.37 (d, J=6 Hz, 1H), 9.02 (d, J=4 Hz, 1H).

Example 18

8-(1,3-Benzodioxol-4-yl)-4-(2,4-difluorophenyl)-1,7-naphthyridine 7-oxide

Obtained as an off-white solid (54%) from the title compound of Preparation 14 following the experimental procedure of Example 15.
LRMS (m/z): 379 (M+1)+.
Retention Time: 12 min.
¹H-NMR δ (CDCl₃): 6.00 (d, J=2 Hz, 1H), 6.08 (d, J=2 Hz, 1H), 6.99-7.15 (m, 5H), 7.35-7.41 (m, 2H), 7.50 (dd, J=2 and 8 Hz, 1H), 8.33 (d, J=8 Hz, 1H), 9.01 (d, J=4 Hz, 1H).

Example 19

4-(2,4-Difluorophenyl)-8-(2,6-difluorophenyl)-1,7-naphthyridine 7-oxide

Obtained as an off-white solid (17%) from the title compound of Preparation 15 following the experimental procedure of Example 15.
LRMS (m/z): 371 (M+1)+.
Retention Time: 14 min.
¹H-NMR δ (CDCl₃): 7.06-7.16 (m, 4H), 7.37-7.55 (m, 3H), 7.57 (dd, J=2 and 6 Hz, 1H), 8.34 (d, J=8 Hz, 1H), 8.97 (d, J=6 Hz, 1H).

Example 20

4-(2,4-Difluorophenyl)-8-(2,6-dimethylphenyl)-1,7-naphthyridine 7-oxide

Obtained as an off-white solid (53%) from the title compound of Preparation 16 following the experimental procedure of Example 15.
LRMS (m/z): 363 (M+1)+.
Retention Time: 14 min.
¹H-NMR δ (CDCl₃): 2.03 (s, 6H), 7.04-7.17 (m, 1H), 7.11 (d, J=8 Hz, 1H), 7.22-7.26 (m, 2H), 7.35 (d, J=6 Hz, 1H), 7.38-7.47 (m, 2H), 7.53 (dd, J=2 and 8 Hz, 1H), 8.36 (d, J=8 Hz, 1H), 8.96 (d, J=6 Hz, 1H).

Example 21

4-(2,4-Difluorophenyl)-8-(2,6-dimethoxyphenyl)-1,7-naphthyridine 7-oxide

Obtained as an off-white solid (63%) from the title compound of Preparation 17 following the experimental procedure of Example 15.
LRMS (m/z): 395 (M+1)+.
Retention Time: 13 min.
¹H-NMR δ (CDCl₃): 3.74 (s, 6H), 6.76 (d, J=8 Hz, 2H), 7.02-7.16 (m, 2H), 7.33 (d, J=6 Hz, 1H), 7.35-7.53 (m, 2H), 7.47 (d, J=8 Hz, 1H), 8.30 (d, J=8 Hz, 1H), 8.94 (d, J=6 Hz, 1H).

Example 22

N-{4-[4-(2,4-Difluorophenyl)-7-oxido-1,7-naphthyridin-8-yl]-3-methylphenyl}methanesulfonamide Obtained as an off-white solid (21%) from the title compound of Preparation 18 following the experimental procedure of Example 15.
LRMS (m/z): 442 (M+1)+.
Retention Time: 12 min.
¹H-NMR δ (CDCl₃): 2.15 (s, 3H), 3.08 (s, 3H), 7.04-7.23 (m, 5H), 7.39-7.45 (m, 2H), 7.57 (dd, J=2 and 6 Hz, 1H), 8.00 (brs, 1H), 8.37 (d, J=8 Hz, 1H), 8.99 (d, J=6 Hz, 1H).

Example 23

8-(2-Chlorophenyl)-4-(2,4-difluorophenyl)-1,7-naphthyridine 7-oxide

Obtained as an off-white solid (85%) from the title compound of Preparation 19 following the experimental procedure of Example 15.
LRMS (m/z): 369, 371 (M+1)+.
Retention Time: 14 min.
¹H-NMR δ (DMSO-d₆): 7.30-7.41 (m, 1H), 7.45-7.70 (m, 8H), 8.38 (d, J=8 Hz, 1H), 8.94 (d, J=4 Hz, 1H).

Example 24

4-(2,4-Difluorophenyl)-8-(2-fluorophenyl)-1,7-naphthyridine 7-oxide

Obtained as an off-white solid (51%) from the title compound of Preparation 20 following the experimental procedure of Example 15.
LRMS (m/z): 353 (M+1)+.
Retention Time: 13 min.
¹H-NMR δ (DMSO-d₆): 7.30-7.42 (m, 1H), 7.50-7.74 (m, 8H), 8.38 (d, J=6 Hz, 1H), 8.96 (d, J=4 Hz, 1H).

Example 25

8-(2,6-Dichlorophenyl-4-(2,4-difluorophenyl)-1,7-naphthyridine 7-oxide

Obtained as an off-white solid (57%) from the title compound of Preparation 21 following the experimental procedure of Example 15.

LRMS (m/z): 403, 405, 407 (M+1)⁺.
Retention Time: 14 min.
¹H-NMR δ (CDCl₃): 7.04-7.20 (m, 2H), 7.39-7.61 (m, 6H), 8.33 (d, J=8 Hz, 1H), 8.96 (d, J=6 Hz, 1H).

Example 26

4-(2,4-Difluorophenyl)-8-(2-methylphenyl)-2-piperidin-4-yl-1,7-naphthyridine 7-oxide Obtained as an off-white solid (43%) from the title compound of Preparation 11 following the experimental procedure of Example 10 (90 min. at 115° C.).
LRMS (m/z): 432 (M+1)⁺.
Retention Time: 9 min.
¹H-NMR δ (CDCl₃): 1.8-2.20 (m, 4H), 2.15 (s, 3H), 2.80-3.00 (m, 2H), 3.05-3.35 (m, 3H), 7.03-7.15 (m, 2H), 7.29-7.43 (m, 6H), 7.49 (dd, J=4 and 8 Hz, 1H), 8.32 (d, J=6 Hz, 1H).

Example 27

8-(2-Chlorophenyl)-4-(2,4-difluorophenyl)-2-piperidin-4-yl-1,7-naphthyridine 7-oxide Obtained as an off-white solid (27%) from the title compound of Preparation 19 following the experimental procedure of Example 10 (90 min. at 115° C.).
LRMS (m/z): 452, 454 (M+1)⁺.
Retention Time: 9 min.
¹H-NMR δ (CDCl₃): 1.53-1.90 (m, 4H), 2.64-2.76 (m, 2H), 2.82-3.00 (m, 1H), 3.10-3.16 (m, 2H), 7.00-7.16 (m, 2H), 7.36-7.62 (m, 7H), 8.28 (d, J=8 Hz, 1H).

Example 28

4-(2,4-Difluorophenyl)-8-(2-fluorophenyl)-2-piperidin-4-yl-1,7-naphthyridine 7-oxide Obtained as an off-white solid (75%) from the title compound of Preparation 20 following the experimental procedure of Example 10 (90 min. at 115° C.).
LRMS (m/z): 436 (M+1)⁺.
Retention Time: 9 min.
¹H-NMR δ (DMSO-d₆): 1.38-1.55 (m, 2H), 1.65-1.75 (m, 2H), 2.42-2.56 (m, 2H), 2.75-3.00 (m, 3H), 7.30-7.40 (m, 3H), 7.50-7.72 (m, 6H), 8.32 (d, J=8 Hz, 1H).

Example 29

4-(2,4-Difluorophenyl)-8-(2,6-difluorophenyl)-2-piperidin-4-yl-1,7-naphthyridine 7-oxide Obtained as an off-white solid (68%) from the title compound of Preparation 15 following the experimental procedure of Example 10 (90 min. at 115° C.).
LRMS (m/z): 454 (M+1)⁺.
Retention Time: 9 min.
¹H-NMR δ (CDCl₃): 1.65-1.95 (m, 4H), 2.65-2.80 (m, 2H), 2.85-3.00 (m, 1H), 3.10-3.25 (m, 2H), 7.02-7.16 (m, 4H), 7.29-7.60 (m, 4H), 8.28 (d, J=8 Hz, 1H).

Example 30

8-(2,6-dichlorophenyl)-4-(2,4-difluorophenyl)-2-(piperidin-4-yl)-1,7-naphthyridine 7-oxide Obtained as an off-white solid (73%) from the title compound of Preparation 21 following the experimental procedure of Example 10 (90 min. at 115° C.).

LRMS (m/z): 486, 488, 490 (M+1)⁺.
Retention Time: 9 min.
¹H-NMR δ (CDCl₃): 1.55-1.94 (m, 4H), 2.64-2.77 (m, 2H), 2.84-3.00 (m, 1H), 3.08-3.20 (m, 2H), 7.02-7.16 (m, 2H), 7.29-7.55 (m, 6H), 8.28 (d, J=8 Hz, 1H).

Example 31

4-(2,4-Difluorophenyl)-8-(2,6-difluorophenyl)-2-(1-methylpiperidin-4-yl)-1,7-naphthyridine 7-oxide Formic acid (0.075 mL, 1.99 mmol) and formaldehyde (37% in water) (0.15 mL, 1.99 mmol) were added to the title compound of Example 29 (90 mg, 0.199 mmol) and the reaction was heated at 80° C. for 4 hours and at room temperature for 16 hours. The mixture was purified directly by column chromatography (C-18 silica from Waters©, reverse phase water/acetonitrile as eluents [0.1% v/v formic acid buffered] 0% to 40%). The acetonitrile from the appropriate fractions was evaporated and the aqueous phase basified to pH=10. It was extracted with ethyl acetate, dried over sodium sulphate and the solvent removed under reduced pressure to give the title compound as an yellowish solid (70 mg, 75% yield).
LRMS (m/z): 468 (M+1)⁺.
Retention Time: 9 min.
¹H-NMR δ (CDCl₃): 1.75-2.12 (m, 6H), 2.30 (s, 3H), 2.75-2.84 (m, 1H), 2.85-3.00 (m, 2H), 7.01-7.15 (m, 4H), 7.29 (s, 1H), 7.34-7.58 (m, 3H), 8.28 (d, J=8 Hz, 1H).

Example 32

8-(2,6-Dichlorophenyl)-4-(2,4-difluorophenyl)-2-(1-methylpiperidin-4-yl)-1,7-naphthyridine 7-oxide Obtained as an off-white solid (58%) from the title compound of Example 30 following the experimental procedure of Example 31.
LRMS (m/z): 500, 502, 504 (M+1)⁺.
Retention Time: 9 min.
¹H-NMR δ (CDCl₃): 1.75-1.90 (m, 4H), 2.00-2.10 (m, 2H), 2.27 (s, 3H), 2.70-2.80 (m, 1H), 2.84-3.00 (m, 2H), 7.01-7.16 (m, 2H), 7.29-7.51 (m, 5H), 7.53 (dd, J=4 and 6 Hz, 1H), 8.28 (d, J=8 Hz, 1H).

Example 33

4-(2,4-Difluorophenyl)-8-(2,6-difluorophenyl)-2-(1-isopropylpiperidin-4-yl)-1,7-naphthyridine 7-oxide 2-Bromopropane (0.083 mL, 0.88 mmol), potassium iodide (7 mg, 0.044 mmol) and potassium carbonate (61 mg, 0.44 mmol) were sequentially added to a solution of the title compound of Example 29 (100 mg, 0.22 mmol) in 3 mL of acetonitrile and the mixture was stirred at 80° C. for 7 hours. After cooling down, the reaction mixture was filtered through a sintered glass to eliminate most of the inorganic salts. The solvent was removed under reduced pressure and the oily material purified by column chromatography (C-18 silica from Waters©, reverse phase water/acetonitrile as eluents [0.1% v/v formic acid buffered] 0% to 100%). The acetonitrile from the appropriate fractions was evaporated and the aqueous phase basified to pH=10. It was extracted with ethyl acetate, dried over sodium sulphate and the solvent removed under reduced pressure to give the title compound as an off-white solid (47 mg, 43% yield).

LRMS (m/z): 496 (M+1)+.
Retention Time: 9 min.
$^1$H-NMR δ (CDCl$_3$): 1.08 (d, J=6 Hz, 6H), 1.80-2.10 (m, 4H), 2.25-2.45 (m, 2H), 2.80-2.88 (m 2H), 2.94-3.04 (m, 2H), 7.01-7.16 (m, 4H), 7.31-7.56 (m, 3H), 7.50 (dd, J=2 and 8 Hz, 1H), 8.29 (d, J=8 Hz, 1H).

Example 34

8-(2,6-Dichlorophenyl)-4-(2,4-difluorophenyl)-2-(1-isopropylpiperidin-4-yl)-1,7-naphthyridine 7-oxide Obtained as an off-white solid (73%) from the title compound of Example 30 following the experimental procedure of Example 33.
LRMS (m/z): 528, 530, 532 (M+1)+.
Retention Time: 10 min.
$^1$H-NMR δ (CDCl$_3$): 1.06 (d, J=6 Hz, 6H), 1.65-2.00 (m, 4H), 2.15-2.35 (m, 2H), 2.67-2.85 (m 2H), 2.86-3.00 (m, 2H), 7.02-7.16 (m, 2H), 7.31 (s, 1H), 7.37-7.55 (m, 5H), 8.28 (d, J=8 Hz, 1H).

Example 35

2-(1-Tert-butylpiperidin-4-yl)-4-(2,4-difluorophenyl)-8-(2,6-difluorophenyl)-1,7-naphthyridine 7-oxide Sulfuric acid 98% (0.18 mL) was dropwise added to a suspension of the title compound of Preparation 15 (152 mg, 0.42 mmol), anhydrous magnesium sulphate (365 mg) and the title compound of Preparation 56 (120 mg, 0.65 mmol) in 4 mL of toluene and the mixture was vigorously stirred in a pre-heated oil bath at 115° C. After 90 minutes, the reaction was cooled down and the solvent discarded. The residue was washed with ethyl acetate, dissolved in methanol and filtered through a sintered glass to eliminate most of the inorganic salts. The solvent was removed under reduced pressure and the oily material purified by column chromatography (C-18 silica from Waters©, reverse phase water/acetonitrile as eluents [0.1% v/v formic acid buffered] 0% to 30%). The acetonitrile from the appropriate fractions was evaporated and the aqueous phase basified to pH=10. A white solid precipitated. It was filtered, washed with water and dried under vacuum (45° C.) for 18 hours to give the title compound as a white solid (130 mg, 61% yield).
LRMS (m/z): 510 (M+1)+.
Retention Time: 10 min.
$^1$H-NMR δ (CDCl$_3$): 1.08 (s, 9H), 1.71-1.85 (m, 2H), 1.94-1.97 (m, 2H), 2.17-2.23 (m, 2H), 2.77 (m, 1H), 3.08-3.12 (m, 2H), 7.03-7.13 (m, 4H), 7.32 (s, 1H), 7.38 (m, 1H), 7.48-7.56 (m, 2H), 8.28 (d, J=6 Hz, 1H).

Example 36

2-(1-Tert-butylpiperidin-4-yl)-8-(2,6-dichlorophenyl)-4-(2,4-difluorophenyl)-1,7-naphthyridine 7-oxide Obtained as a white solid (68%) from the title compound of Preparation 21 following the experimental procedure of Example 35.
LRMS (m/z): 542, 544, 546 (M+1)+.
Retention Time: 10 min.
$^1$H-NMR δ (CDCl$_3$): 1.08 (s, 9H), 1.73-1.81 (m, 2H), 1.92-1.96 (m, 2H), 2.17-2.23 (m, 2H), 2.77 (m, 1H), 3.05-3.09 (m, 2H), 7.04-7.14 (m, 2H), 7.32 (s, 1H), 7.39-7.44 (m, 2H), 7.47-7.53 (m, 3H), 8.27 (d, J=6 Hz, 1H).

Example 37

4-(2-Chloro-4-fluorophenyl)-8-(2,6-difluorophenyl)-2-piperidin-4-yl-1,7-naphthyridine Obtained as an off-white solid (77%) from the title compound of Preparation 22 following the experimental procedure of Example 10.
LRMS (m/z): 454, 456 (M+1)+.
Retention Time: 12 min.
$^1$H-NMR δ (CDCl$_3$): 1.95-2.10 (m, 2H), 2.12-2.30 (m, 2H), 2.90-3.20 (m, 3H), 3.30-3.45 (m, 2H), 7.05-7.24 (m, 3H), 7.32-7.53 (m, 5H), 8.69 (d, J=6H, 1H).

Example 38

4-(2-Chloro-4-fluorophenyl)-8-(2,6-dichlorophenyl)-2-piperidin-4-yl-1,7-naphthyridine Obtained as an off-white solid (36%) from the title compound of Preparation 23 following the experimental procedure of Example 10.
LRMS (m/z): 486, 488, 450, 452 (M+1)+.
Retention Time: 13 min.
$^1$H-NMR δ (DMSO-d$_6$): 1.62-1.72 (m, 2H), 1.90-1.95 (m, 2H), 2.45-2.55 (m, 2H), 2.74-2.80 (m, 1H), 3.09-3.12 (m, 2H), 7.43-7.50 (m, 2H), 7.55-7.72 (m, 5H), 7.75-7.79 (m, 1H), 8.32 (s, 1H, NH), 8.66 (d, J=4 Hz, 1H).

Example 39

4-(2-Chloro-4-fluorophenyl)-8-(2,6-difluorophenyl)-1,7-naphthyridine 7-oxide

Obtained as an off-white solid (17%) from the title compound of Preparation 24 following the experimental procedure of Example 15.
LRMS (m/z): 387, 389 (M+1)+.
Retention Time: 15 min.
$^1$H-NMR δ (CDCl$_3$): 7.08-7.22 (m, 3H), 7.34-7.44 (m, 4H), 7.51-7.60 (m, 1H), 8.31 (d, J=8 Hz, 1H), 8.99 (d, J=4 Hz, 1H).

Example 40

4-(2-Chloro-4-fluorophenyl)-8-(2,6-dichlorophenyl)-1,7-naphthyridine 7-oxide

Obtained as an off-white solid (16%) from the title compound of Preparation 25 following the experimental procedure of Example 15.
LRMS (m/z): 419, 421, 423, 425 (M+1)+.
Retention Time: 16 min.
$^1$H-NMR δ (CDCl$_3$): 7.27-7.57 (m, 8H), 8.30 (d, J=6 Hz, 1H), 8.98 (d, J=4 Hz, 1H).

Example 41

4-(2-Chloro-4-fluorophenyl)-8-(2-chlorophenyl)-2-piperidin-4-yl-1,7-naphthyridin-7-oxide Obtained as an off-white solid (34%) from the title compound of Preparation 26 following the experimental procedure of Example 10 (90 min. at 115° C.).

LRMS (m/z): 468, 470, 472 (M+1)⁺.
Retention Time: 10 min.
¹H-NMR δ (CDCl₃): 1.75-1.80 (m, 2H), 1.92-1.94 (m, 2H), 2.23-2.25 (m, 2H), 2.70-2.78 (m, 1H), 2.91-2.95 (m, 2H), 7.17-7.22 (m, 1H), 7.35-7.43 (m, 5H), 7.48-7.52 (m, 3H), 8.24 (d, J=4 Hz, 1H).

Example 42

4-(2-Chloro-4-fluorophenyl)-8-(2,6-difluorophenyl)-2-piperidin-4-yl-1,7-naphthyridine 7-oxide Obtained as an off-white solid (34%) from the title compound of Preparation 24 following the experimental procedure of Example 10 (90 min. at 115° C.).
LRMS (m/z): 470, 472 (M+1)⁺.
Retention Time: 10 min.
¹H-NMR δ (CDCl₃): 1.58-1.74 (m, 2H), 1.87-1.93 (m, 2H), 2.66-2.77 (m, 2H), 2.84-3.00 (m, 1H), 3.12-3.18 (m, 2H), 7.05-7.25 (m, 4H), 7.32-7.39 (m, 3H), 7.45-7.60 (m, 1H), 8.26 (d, J=8 Hz, 1H).

Example 43

4-(2-Chloro-4-fluorophenyl)-8-(2,6-dichlorophenyl)-2-piperidin-4-yl-1,7-naphthyridine 7-oxide Obtained as an off-white solid (36%) from the title compound of Preparation 25 following the experimental procedure of Example 10 (90 min. at 115° C.).
LRMS (m/z): 502, 504, 506, 508 (M+1)⁺.
Retention Time: 10 min.
¹H-NMR δ (CDCl₃): 2.04-2.10 (m, 2H), 2.25-2.36 (m, 2H), 3.00-3.10 (m, 2H), 3.19 (m, 1H), 3.28-3.34 (m, 2H), 7.16-7.26 (m, 2H), 7.35-7.54 (m, 6H), 8.28 (d, J=8 Hz, 1H).

Example 44

4-(2-Chloro-4-fluorophenyl)-8-(2,6-difluorophenyl)-2-(1-methylpiperidin-4-yl)-1,7-naphthyridine 7-oxide Obtained as an off-white solid (69%) from the title compound of Example 42 following the experimental procedure of Example 31.
LRMS (m/z): 484, 486 (M+1)⁺.
Retention Time: 9 min.
¹H-NMR δ (CDCl₃): 1.69-1.95 (m, 4I), 2.04-2.08 (m, 2H), 2.29 (s, 3H), 2.76-2.80 (m, 1H), 2.90-2.93 (m, 2H), 7.05-7.11 (m, 2H), 7.18-7.21 (m, 1H), 7.25 (s, 1H), 7.33-7.38 (m, 3H), 7.47-7.55 (m, 1H), 8.25 (d, J=4 Hz, 1H).

Example 45

4-(2-Chloro-4-fluorophenyl)-8-(2,6-dichlorophenyl)-2-(1-methylpiperidin-4-yl)-1,7-naphthyridine 7-oxide Obtained as an off-white solid (17%) from the title compound of Example 43 following the experimental procedure of Example 31.
LRMS (m/z): 516, 518, 520, 522 (M+1)⁺.
Retention Time: 10 min.
¹H-NMR δ (CDCl₃): 1.76-1.87 (m, 4H), 2.00-2.08 (m, 21-1), 2.27 (s, 3H), 2.76-2.80 (m, 1H), 2.80-2.93 (m, 2H), 7.05-7.11 (m, 2H), 7.38-7.52 (m, 5H), 7.55-7.60 (m, 1H), 8.24 (d, J=4 Hz, 1H).

Example 46

4-(2-Chloro-4-fluorophenyl)-8-(2,6-difluorophenyl)-2-(1-isopropylpiperidin-4-yl)-1,7-naphthyridine 7-oxide Obtained as an off-white solid (30%) from the title compound of Example 42 following the experimental procedure of Example 33.
LRMS (m/z): 512, 514 (M+1)⁺.
Retention Time: 10 min.
¹H-NMR δ (CDCl₃): 1.06 (d, J=4 Hz, 6H), 1.84-1.86 (m, 2H), 1.95-2.00 (m, 2H), 2.26-2.28 (m, 2H), 2.74-2.80 (m, 2H), 2.94-2.97 (m, 2H), 7.06-7.12 (m, 2H), 7.16-7.21 (m, 1H), 7.31-7.38 (m, 4H), 7.47-7.55 (m, 1H), 8.25 (d, J=4 Hz, 1H).

Example 47

4-(2-Chloro-4-fluorophenyl)-8-(2,6-dichlorophenyl)-2-(1-isopropylpiperidin-4-yl)-1,7-naphthyridine 7-oxide Obtained as an off-white solid (67%) from the title compound of Example 43 following the experimental procedure of Example 33.
LRMS (m/z): 544, 546, 548, 560 (M+1)⁺.
Retention Time: 10 min.
¹H-NMR δ (CDCl₃): 1.05 (d, J=6 Hz, 6H), 1.73-1.83 (m, 2H), 1.93-1.96 (m, 2H), 2.22-2.27 (m, 2H), 2.69-2.75 (m 1H), 2.76-2.83 (m, 1H), 2.91-2.94 (m, 2H), 7.17-7.22 (m, 1H), 7.27 (s, 1H), 7.35-7.44 (m, 4H), 7.48-7.51 (m, 2H), 8.25 (d, J=8 Hz, 1H).

Example 48

2-(1-Tert-butylpiperidin-4-yl)-4-(2-chloro-4-fluorophenyl)-8-(2,6-difluorophenyl)-1,7-naphthyridine 7-oxide Obtained as a white solid (67%) from the title compound of Preparation 24 following the experimental procedure of Example 35.
LRMS (m/z): 526, 528 (M+1)⁺.
Retention Time: 10 min.
¹H-NMR δ (CDCl₃): 1.09 (s, 9H), 1.77-1.84 (m, 2H), 1.96-2.00 (m, 2H), 2.18-2.23 (m, 2H), 2.79 (m, 1H), 3.09-3.13 (m, 2H), 7.06-7.12 (m, 2H), 7.18 (dd, J=3 and 9 Hz, 1H), 7.28 (s, 1H), 7.32-7.38 (m, 3H), 7.52 (m, 1H), 8.25 (d, J=9 Hz, 1H).

Example 49

2-(1-Tert-butylpiperidin-4-yl)-4-(2-chloro-4-fluorophenyl)-8-(2,6-dichlorophenyl)-1,7-naphthyridine 7-oxide Obtained as a white solid (32%) from the title compound of Preparation 25 following the experimental procedure of Example 35.
LRMS (m/z): 558, 560, 562, 564 (M+1)⁺.
Retention Time: 10 min.
¹H-NMR δ (CDCl₃): 1.08 (s, 9H), 1.75-1.81 (m, 2H), 1.93-1.96 (m, 2H), 2.17-2.23 (m, 2H), 2.78 (m, 1H), 3.06-3.10 (m, 2H), 7.21 (m, 1H), 7.29 (s, 1H), 7.36-7.45 (m, 4H), 7.49-7.53 (m, 2H), 8.25 (d, J=9 Hz, 1H).

Example 50

4-(2-Chlorophenyl)-8-(2,6-difluorophenyl)-2-piperidin-4-yl-1,7-naphthyridine Obtained as an off-white solid (71%) from the title compound of Preparation 27 following the experimental procedure of Example 10.
LRMS (m/z): 436, 438 (M+1)$^+$.
Retention Time: 12 min.
$^1$H-NMR δ (CDCl$_3$): 1.76-1.80 (m, 2H), 1.96-2.00 (m, 2H), 2.74-2.80 (m, 2H), 2.99-3.01 (m, 1H), 3.17-3.20 (m, 2H), 7.04-7.10 (m, 2H), 7.25-7.50 (m, 6H), 7.58-7.62 (m, 1H), 8.64 (d, J=4 Hz, 1H).

Example 51

4-(2-Chlorophenyl)-8-(2,6-dichlorophenyl)-2-piperidin-4-yl-1,7-naphthyridine Obtained as an off-white solid (65%) from the title compound of Preparation 28 following the experimental procedure of Example 10.
LRMS (m/z): 468, 470, 472, 474 (M+1)$^+$.
Retention Time: 12 min.
$^1$H-NMR δ (CDCl$_3$): 1.76-1.80 (m, 2H), 1.96-2.00 (m, 2H), 2.74-2.80 (m, 2H), 2.99-3.01 (m, 1H), 3.17-3.20 (m, 2H), 7.31-7.51 (m, 8H), 7.58-7.64 (m, 1H), 8.63 (d, J=4 Hz, 1H).

Example 52

4-(2-Chlorophenyl)-8-(2,6-difluorophenyl)-2-piperidin-4-yl-1,7-naphthyridine 7-oxide Obtained as an off-white solid (47%) from the title compound of Preparation 29 following the experimental procedure of Example 10 (90 min. at 115° C.).
LRMS (m/z): 452, 454 (M+1)$^+$.
Retention Time: 9 min.
$^1$H-NMR δ (CDCl$_3$): 1.72-1.84 (m, 2H), 1.95-2.00 (m, 2H), 2.70-2.86 (m, 2H), 2.95-3.02 (m, 1H), 3.16-3.25 (m, 2H), 7.06-7.16 (m, 2H), 7.28-7.63 (m, 7H), 8.26 (d, J=8 Hz, 1H).

Example 53

4-(2-Chlorophenyl)-8-(2,6-dichlorophenyl)-2-piperidin-4-yl-1,7-naphthyridine 7-oxide Obtained as an off-white solid (43%) from the title compound of Preparation 30 following the experimental procedure of Example 10 (90 min. at 115° C.).
LRMS (m/z): 484, 486, 488, 490 (M+1)$^+$.
Retention Time: 10 min.
$^1$H-NMR δ (CDCl$_3$): 1.75-1.82 (m, 2H), 2.01-2.04 (m, 2H), 2.78-2.84 (m, 2H), 3.00 (m, 1H), 3.17-3.20 (m, 2H), 7.27-7.30 (m, 1H), 7.38-7.54 (m, 7H), 7.56-7.64 (m, 1H), 8.24 (d, J=6 Hz, 1H).

Example 54

4-(2-Chlorophenyl)-8-(2,6-difluorophenyl)-2-(1-methylpiperidin-4-yl)-1,7-naphthyridine 7-oxide Obtained as an off-white solid (87%) from the title compound of Example 52 following the experimental procedure of Example 31.
LRMS (m/z): 466, 468 (M+1)$^+$.
Retention Time: 9 min.
$^1$H-NMR δ (CDCl$_3$): 1.85-2.00 (m 4H), 2.04-2.15 (m, 2H), 2.29 (s, 3H), 2.75-2.82 (m, 1H), 2.90-2.94 (m, 2H), 7.04-7.10 (m, 2H), 7.26-7.37 (m, 3H), 7.42-7.52 (m, 3H), 7.59 (dd, J=2 and 4 Hz, 1H), 8.25 (d, J=4 Hz, 1H).

Example 55

4-(2-Chlorophenyl)-8-(2,6-dichlorophenyl)-2-(1-methylpiperidin-4-yl)-1,7-naphthyridine 7-oxide Obtained as an off-white solid (52%) from the title compound of Example 53 following the experimental procedure of Example 31.
LRMS (m/z): 498, 500, 502, 504 (M+1)$^+$.
Retention Time: 10 min.
$^1$H-NMR δ (CDCl$_3$): 1.75-1.95 (m 4H), 2.02-2.11 (m, 2H), 2.28 (s, 3H), 2.75-2.82 (m, 1H), 2.87-2.92 (m, 2H), 7.28 (s, 1H), 7.38-7.52 (m, 7H), 7.60 (dd, J=2 and 4 Hz, 1H), 8.24 (d, J=4 Hz, 1H).

Example 56

4-(2-Chlorophenyl)-8-(2,6-difluorophenyl)-2-(1-isopropylpiperidin-4-yl)-1,7-naphthyridine 7-oxide Obtained as an off-white solid (49%) from the title compound of Example 52 following the experimental procedure of Example 33.
LRMS (m/z): 494, 496 (M+1)$^+$.
Retention Time: 10 min.
$^1$H-NMR δ (CDCl$_3$): 1.08 (d, J=4 Hz, 1H), 1.85-2.05 (m, 4H), 2.30-2.38 (m, 2H), 2.80-2.90 (m, 2H), 2.95-3.05 (m, 2H), 7.07-7.12 (m, 2H), 7.30-7.39 (m, 3H), 7.44-7.55 (m, 3H), 7.58-7.62 (m, 1H), 8.25 (d, J=4 Hz, 1H).

Example 57

4-(2-Chlorophenyl)-8-(2,6-dichlorophenyl)-2-(1-isopropylpiperidin-4-yl)-1,7-naphthyridine 7-oxide Obtained as an off-white solid (49%) from the title compound of Example 53 following the experimental procedure of Example 33.
LRMS (m/z): 526, 528, 530, 532 (M+1)$^+$.
Retention Time: 10 min.
$^1$H-NMR δ (CDCl$_3$): 1.07 (d, J=6 Hz, 6H), 1.65-2.00 (m, 4H), 2.15-2.35 (m, 2H), 2.67-2.85 (m, 2H), 2.86-3.00 (m, 211), 7.30 (s, 1H), 7.38-7.52 (m, 7H), 7.60 (dd, J=2 and 4 Hz, 1H), 8.24 (d, J=4 Hz, 1H).

Example 58

2-(1-Tert-butylpiperidin-4-yl)-4-(2-chlorophenyl)-8-(2,6-difluorophenyl)-1,7-naphthyridine 7-oxide Obtained as a white solid (58%) from the title compound of Preparation 29 following the experimental procedure of Example 35.
LRMS (m/z): 508, 510 (M+1)$^+$.
Retention Time: 10 min.
$^1$H-NMR δ (CDCl$_3$): 1.08 (s, 9H), 1.72-1.84 (m, 2H), 1.95-1.99 (m, 2H), 2.16-2.24 (m, 2H), 2.78 (m, 1H), 3.08-3.12 (m, 2H), 7.06-7.13 (m, 2H), 7.30 (s, 1H), 7.33-7.61 (m, 6H), 8.24 (d, J=6 Hz, 1H).

Example 59

2-(1-Tert-butylpiperidin-4-yl)-4-(2-chlorophenyl)-8-(2,6-dichlorophenyl)-1,7-naphthyridine 7-oxide Obtained as a white solid (48%) from the title compound of Preparation 30 following the experimental procedure of Example 35.
LRMS (m/z): 540, 542, 544, 546 (M+1)$^+$.
Retention Time: 10 min.
$^1$H-NMR δ (CDCl$_3$): 1.07 (s, 9H), 1.73-1.82 (m, 2H), 1.93-1.96 (m, 2H), 2.18-2.23 (m, 2H), 2.79 (m, 1H), 3.05-3.09 (m, 2H), 7.30 (s, 1H), 7.38-7.51 (m, 7H), 7.60 (m, 1H), 8.24 (d, J=9 Hz, 1H).

Example 60

8-(2,6-Difluorophenyl)-4-(2-methoxyphenyl)-1,7-naphthyridine

Obtained as an off-white solid (49%) from the title compound of Preparation 31 following the experimental procedure of Example 1.
LRMS (m/z): 349 (M+1)$^+$.
Retention Time: 16 min.
$^1$H-NMR δ (CDCl$_3$): 3.77 (s, 3H), 7.05-7.19 (m, 4H), 7.30 (dd, J=2 and 8 Hz, 1H), 7.42-7.57 (m, 4H), 8.65 (d, J=6 Hz, 1H), 9.02 (d, J=4 Hz, 1H).

Example 61

8-(2,6-Dimethylphenyl)-4-(2-methoxyphenyl)-1,7-naphthyridine

Obtained as an off-white solid (81%) from the title compound of Preparation 32 following the experimental procedure of Example 1.
LRMS (m/z): 341 (M+1)$^+$.
Retention Time: 16 min.
$^1$H-NMR δ (CDCl$_3$): 1.94 (s, 3H), 2.00 (s, 3H), 3.78 (s, 3H), 7.10-7.34 (m, 5H), 7.46-7.54 (m, 4H), 8.62 (d, J=6 Hz, 1H), 8.99 (d, J=4 Hz, 1H).

Example 62

N-{4-[4-(2-methoxyphenyl)-1,7-naphthyridin-8-yl]-3-methylphenyl}methanesulfonamide Obtained as an off-white solid (52%) from the title compound of Preparation 33 following the experimental procedure of Example 1.
LRMS (m/z): 420 (M+1)$^+$.
Retention Time: 14 min.
$^1$H-NMR δ (CDCl$_3$): 2.18 (s, 3H), 3.08 (s, 3H), 3.78 (s, 3H), 6.79 (brs, 1H), 7.10-7.19 (m, 4H), 7.30 (dd, J=2 and 8 Hz, 1H), 7.43-7.58 (m, 4H), 8.60 (d, J=6 Hz, 1H), 9.02 (d, J=4 Hz, 1H).

Example 63

8-(2,6-Difluorophenyl)-4-(2-methoxyphenyl)-1,7-naphthyridine 7-oxide

Obtained as an off-white solid (45%) from the title compound of Preparation 34 following the experimental procedure of Example 15.
LRMS (m/z): 365 (M+1)$^+$.
Retention Time: 14 min.
$^1$H-NMR δ (CDCl$_3$): 3.78 (s, 3H), 7.08-7.18 (m, 4H), 7.27-7.31 (m, 1H), 7.37 (d, J=4 Hz, 1H), 7.47-7.60 (m, 3H), 8.27 (d, J=6 Hz, 1H), 8.94 (d, J=4 Hz, 1H).

Example 64

8-(2,6-Dimethylphenyl)-4-(2-methoxyphenyl)-1,7-naphthyridine 7-oxide

Obtained as an off-white solid (49%) from the title compound of Preparation 35 following the experimental procedure of Example 15.
LRMS (m/z): 357 (M+1)$^+$.
Retention Time: 14 min.
$^1$H-NMR δ (CDCl$_3$): 2.02 (s, 3H), 2.07 (s, 3H), 3.79 (s, 3H), 7.09-7.25 (m, 4H), 7.30-7.40 (m, 2H), 7.36 (d, J=6 Hz, 1H), 7.50 (d, J=8 Hz, 1H), 7.49-7.58 (m, 1H), 8.29 (d, J=8 Hz, 1H), 8.93 (d, J=6 Hz, 1H).

Example 65

N-{4-[4-(2-methoxyphenyl)-7-oxido-1,7-naphthyridin-8-yl]-3-methylphenyl}methanesulfonamide Obtained as an off-white solid (24%) from the title compound of Preparation 36 following the experimental procedure of Example 15.
LRMS (m/z): 436 (M+1)$^+$.
Retention Time: 12 min.
$^1$H-NMR δ (CDCl$_3$): 2.14 and 2.19 (2 s, 3H, diastereomers), 3.07 (s, 3H), 3.80 (s, 3H), 7.06-7.20 (m, 4H), 7.27-7.41 (m, 3H), 7.50-7.59 (m, 2H), 8.12 and 8.16 (2 brs, 1H, diastereomers), 8.30 (d, J=8 Hz, 1H), 8.96 (d, J=4 Hz, 1H).

Example 66

8-(2-Chlorophenyl)-4-(2-methoxyphenyl)-1,7-naphthyridine 7-oxide

Obtained as an off-white solid (25%) from the title compound of Preparation 37 following the experimental procedure of Example 15.
LRMS (m/z): 363-365 (M+1)$^+$.
Retention Time: 14 min.
$^1$H-NMR δ (CDCl$_3$): 3.79 (s, 3H), 7.09-7.19 (m, 2H), 7.26-7.37 (m, 2H), 7.46-7.65 (m, 6H), 8.26 (d, J=8 Hz, 1H), 8.93 (d, J=6 Hz, 1H).

Example 67

4,8-Bis(2-methoxyphenyl)-1,7-naphthyridine 7-oxide

Obtained as an off-white solid (49%) from the title compound of Preparation 38 following the experimental procedure of Example 15.

LRMS (m/z): 359 (M+1)⁺.

Retention Time: 13 min.

¹H-NMR δ (CDCl₃): 3.78, 3.79, 3.80 and 3.82 (4 s, 6H, diastereomers), 7.08-7.21 (m, 4H), 7.27-7.58 (m, 6H), 8.24 (d, J=6 Hz, 1H), 8.93 (d, J=4 Hz, 1H).

Example 68

8-(2-Methoxyphenyl)-4-[3-(trifluoromethyl)phenyl]-1,7-naphthyridine 7-oxide

Obtained as an off-white solid (37%) from the title compound of Preparation 39 following the experimental procedure of Example 15.

LRMS (m/z): 397 (M+1)⁺.

Retention Time: 14 min.

¹H-NMR δ (CDCl₃): 3.80 (s, 3H), 7.11-7.22 (m, 2H), 7.36 (d, J=4 Hz, 1H), 7.36-7.41 (m, 1H), 7.51-7.59 (m, 1H), 7.63 (d, J=8 Hz, 1H), 7.70-7.85 (m, 4H), 8.33 (d, J=8 Hz, 1H), 8.96 (d, J=4 Hz, 1H).

Example 69

8-(2,6-Difluorophenyl)-4-[3-(trifluoromethyl)phenyl]-1,7-naphthyridine 7-oxide

Obtained as an off-white solid (59%) from the title compound of Preparation 40 following the experimental procedure of Example 15.

LRMS (m/z): 403 (M+1)⁺.

Retention Time: 15 min.

¹H-NMR δ (CDCl₃): 7.08-7.17 (m, 2H), 7.41 (d, J=4 Hz, 1H), 7.48-7.62 (m, 1H), 7.70-7.86 (m, 4H), 7.71 (d, J=8 Hz, 1H), 8.35 (d, J=8 Hz, 1H), 8.98 (d, J=4 Hz, 1H).

Example 70

8-(2,6-Dichlorophenyl)-4-[3-(trifluoromethyl)phenyl]-1,7-naphthyridine 7-oxide

Obtained as an off-white solid (57%) from the title compound of Preparation 41 following the experimental procedure of Example 15.

LRMS (m/z): 435, 437, 439 (M+1)⁺.

Retention Time: 16 min.

¹H-NMR δ (CDCl₃): 7.42 (d, J=6 Hz, 1H), 7.44-7.57 (m, 3H), 7.73-7.76 (m, 2H), 7.74 (d, J=8 Hz, 1H), 7.80-7.88 (m, 2H), 8.34 (d, J=8 Hz, 1H), 8.97 (d, J=6 Hz, 1H).

Example 71

8-(2-Methoxyphenyl)-4-[3-(trifluoromethyl)phenyl]-2-piperidin-4-yl-1,7-naphthyridine 7-oxide Obtained as an off-white solid (43%) from the title compound of Preparation 39 following the experimental procedure of Example 10 (90 min. at 115° C.).

LRMS (m/z): 480 (M+1)⁺.

Retention Time: 10 min.

¹H-NMR δ (CDCl₃): 1.75-1.95 (m, 2H), 2.00-2.20 (m, 2H), 2.75-3.00 (m, 2H), 3.00-3.10 (m, 1H), 3.15-3.30 (m, 2H), 3.80 (s, 3H), 7.08-7.20 (m, 2H), 7.27 (s, 1H), 7.34-7.40 (m, 1H), 7.50-7.60 (m, 2H), 7.70-7.85 (m, 4H), 8.30 (d, J=8 Hz, 1H).

Example 72

8-(2,6-Difluorophenyl)-4-[3-(trifluoromethyl)phenyl]-2-piperidin-4-yl-1,7-naphthyridine 7-oxide Obtained as an off-white solid (31%) from the title compound of Preparation 40 following the experimental procedure of Example 10 (90 min. at 115° C.).

LRMS (m/z): 486 (M+1)⁺.

Retention Time: 10 min.

¹H-NMR δ (CDCl₃): 1.74-1.92 (m, 2H), 1.98-2.08 (m, 2H), 2.76-2.90 (m, 2H), 2.97-3.10 (m, 1H), 3.20-3.30 (m, 2H), 7.08-7.16 (m, 2H), 7.31 (s, 1H), 7.47-7.85 (m, 6H), 8.32 (d, J=8 Hz, 1H).

Example 73

8-(2,6-Dichlorophenyl)-4-[3-(trifluoromethyl)phenyl]-2-piperidin-4-yl-1,7-naphthyridine 7-oxide Obtained as an off-white solid (30%) from the title compound of Preparation 41 following the experimental procedure of Example 10 (90 min. at 115° C.).

LRMS (m/z): 518, 520, 522 (M+1)⁺.

Retention Time: 11 min.

¹H-NMR δ (CDCl₃): 1.64-1.75 (m, 2H), 1.85-1.95 (m, 2H), 2.66-2.80 (m, 2H), 2.85-3.00 (m, 1H), 3.10-3.20 (m, 2H), 7.30 (s, 1H), 7.38-7.54 (m, 3H), 7.67 (d, J=8 Hz, 1H), 7.70-7.85 (m, 4H), 8.30 (d, J=8 Hz, 1H).

Example 74

8-(2,6-Difluorophenyl)-4-[4-(trifluoromethyl)phenyl]-1,7-naphthyridine 7-oxide

Obtained as an off-white solid (51%) from the title compound of Preparation 42 following the experimental procedure of Example 15.

LRMS (m/z): 403 (M+1)⁺.

Retention Time: 16 min.

¹H-NMR δ (CDCl₃): 7.09-7.17 (m, 2H), 7.40 (d, J=4 Hz, 1H), 7.48-7.60 (m, 1H), 7.65 (d, J=8 Hz, 2H), 7.73 (d, J=8 Hz, 1H), 7.87 (d, J=8 Hz, 2H), 8.35 (d, J=8 Hz, 1H), 8.99 (d, J=4 Hz, 1H).

Example 75

8-(2,6-dichlorophenyl)-4-[4-(trifluoromethyl)phenyl]-1,7-naphthyridine 7-oxide

Obtained as an off-white solid (64%) from the title compound of Preparation 43 following the experimental procedure of Example 15.

LRMS (m/z): 435, 437, 439 (M+1)⁺.

Retention Time: 16 min.

$^1$H-NMR δ (CDCl$_3$): 7.41 (d, J=6 Hz, 1H), 7.46-7.57 (m, 3H), 7.68 (d, J=8 Hz, 2H), 7.75 (d, J=8 Hz, 1H), 7.88 (d, J=8 Hz, 2H), 8.34 (d, J=8 Hz, 1H), 8.97 (d, J=4 Hz, 1H).

Example 76

8-(2,6-difluorophenyl)-4-[4-(trifluoromethyl)phenyl]-2-piperidin-4-yl-1,7-naphthyridine 7-oxide Obtained as an off-white solid (68%) from the title compound of Preparation 42 following the experimental procedure of Example 10 (90 min. at 115° C.).
LRMS (m/z): 486 (M+1)$^+$.
Retention Time: 11 min.
$^1$H-NMR δ (CDCl$_3$): 1.62-1.74 (m, 2H), 1.86-1.95 (m, 2H), 2.64-2.81 (m, 2H), 2.85-3.10 (m, 1H), 3.13-3.22 (m, 2H), 7.05-7.16 (m, 2H), 7.29 (s, 1H), 7.46-7.57 (m, 1H), 7.63 (d, J=8 Hz, 2H), 7.66 (d, J=8 Hz, 1H), 7.85 (d, J=8 Hz, 2H), 8.30 (d, J=8 Hz, 1H).

Example 77

8-(2,6-Dichlorophenyl)-4-[4-(trifluoromethyl)phenyl]-2-piperidin-4-yl-1,7-naphthyridine 7-oxide Obtained as an off-white solid (40%) from the title compound of Preparation 43 following the experimental procedure of Example 10 (90 min. at 115° C.).
LRMS (m/z): 518, 520, 522 (M+1)$^+$.
Retention Time: 11 min.
$^1$H-NMR δ (CDCl$_3$): 1.62-1.74 (m, 2H), 1.82-1.95 (m, 2H), 2.64-2.78 (m, 2H), 2.85-2.97 (m, 11-1), 3.10-3.18 (m, 2H), 7.29 (s, 1H), 7.38-7.54 (m, 3H), 7.67 (d, J=8 Hz, 1H), 7.69 (d, J=8 Hz, 1H), 7.86 (d, J=8 Hz, 2H), 8.29 (d, J=8 Hz, 1H).

Example 78

8-(2,6-Dichlorophenyl)-4-(2,4-difluorophenyl)-N-piperidin-4-yl-1,7-naphthyridin-2-amine a) 4-[8-(2,6-Dichlorophenyl)-4-(2,4-difluorophenyl)-1,7-naphthyridin-2-ylamino]piperidine-1-carboxylic acid tert-butyl ester A mixture of the title compound of Preparation 44d (179 mg, 0.40 mmol) and tent-butyl 4-aminopiperidine-1-carboxylate (352 mg, 1.76 mmol) in ethoxyethanol (2 mL) was heated at 130° C. in a sealed tube for 50 h. The reaction was cooled down, diluted with ethyl acetate (40 mL), washed with water, brine, dried over sodium sulphate and the solvent was removed under reduced pressure. The residue was purified by column chromatography (C-18 silica from Waters©, reverse phase water/acetonitrile as eluents [0.1% v/v formic acid buffered] 0% to 50%) to yield the title compound (60 mg, 26%) as a solid.

b) 8-(2,6-Dichlorophenyl)-4-(2,4-difluorophenyl)-N-piperidin-4-yl-1,7-naphthyridin-2-amine A mixture of the title compound of Example 78a (177 mg, 0.31 mmol) and a solution of hydrochloric acid in dioxane (4M, 1 mL) was stirred for 90 minutes at room temperature. The solvent was removed under reduced pressure and the residue was partitioned between ethyl acetate (30 mL) and a saturated solution of sodium bicarbonate (30 mL). The organic solution was washed with brine, dried over anhydrous sodium sulphate and the solvent removed under reduced pressure to yield the title compound (67 mg, 52%) as a solid.
LRMS (m/z): 485, 487, 489 (M+1)$^+$.
Retention Time: 12 min.
$^1$H-NMR δ (CDCl$_3$): 1.74-1.85 (m, 2H), 2.18-2.22 (m, 2H), 2.68-2.74 (m, 2H), 3.36-3.40 (m, 2H), 3.76-3.80 (m, 1H), 5.16 (d, J=6 Hz, 1H), 6.78 (s, 1H), 7.02-7.12 (m, 2H), 7.25-7.46 (m, 5H), 8.38 (brs, 1H), 8.46 (d, J=6 Hz, 1H).

Example 79

4-(2,4-Difluorophenyl)-8-(2,6-difluorophenyl)-N-piperidin-4-yl-1,7-naphthyridin-2-amine a) 4-[4-(2,4-Difluorophenyl)-8-(2,6-Difluorophenyl)-1,7-naphthyridin-2-ylamino]-piperidine-1-carboxylic acid tert-butyl ester A mixture of the title compound of Preparation 45d (200 mg, 0.50 mmol), tert-butyl 4-aminopiperidine-1-carboxylate (110 mg, 0.55 mmol) and diisopropylethylamine (0.18 mL, 1.01 mmol) in ethoxyethanol (2.5 mL) was heated at 130° C. in a sealed tube for 50 h. The reaction was cooled down, diluted with ethyl acetate (50 mL), washed with water, brine, dried over sodium sulphate and the solvent was removed under reduced pressure. The residue was purified by column chromatography on flash silica using ethyl acetate/hexane (10 to 80% of ethyl acetate) as eluents, to yield the title compound (108 mg, 38%) as a pale yellow solid.

b) 4-(2,4-Difluorophenyl)-8-(2,6-difluorophenyl)-N-piperidin-4-yl-1,7-naphthyridin-2-amine Obtained as a white solid (86%) from the title compound of Example 79a following the experimental procedure described in Example 78b.
LRMS (m/z): 453 (M+1)$^+$.
Retention Time: 11 min.
$^1$H-NMR δ (CD$_3$OD): 1.45 (m, 2H), 2.06 (d, J=12.6 Hz, 2H), 2.55-2.63 (m, 2H), 3.12 (d, J=12.9 Hz, 2H) 3.66-3.70 (m, 1H), 6.93 (s, 1H), 7.08-7.26 (m, 4H), 7.35-7.37 (m, 1H), 7.51-7.55 (m, 2H), 8.25 (m, 1H).

Example 80

8-(2-Chlorophenyl)-4-(2,4-difluorophenyl)-N-piperidin-4-yl-1,7-naphthyridin-2-amine a) 4-[8-(2-Chlorophenyl)-4-(2,4-difluorophenyl)-1,7-naphthyridin-2-ylamino]-piperidine-1-carboxylic acid tert-butyl ester Obtained from the title compound of Preparation 46d following the experimental procedure described in Example 78a. The crude was purified by column chromatography on silica using ethyl acetate/hexane (1:2) as eluents, to yield the title compound (35%) as a white solid.

b) 8-(2-Chlorophenyl)-4-(2,4-difluorophenyl)-N-piperidin-4-yl-1,7-naphthyridin-2-amine A mixture of the title compound of Example 80a (30 mg, 0.055 mmol) and trifluoroacetic acid (0.5 mL) in dichloromethane was stirred for 2 hours at room temperature. The solvent was removed under reduced pressure and the residue was partitioned between ethyl acetate (30 mL) and a saturated solution of sodium bicarbonate (30 mL). The organic solution was washed with brine, dried over anhydrous sodium sulphate and the solvent removed under reduced pressure to yield the title compound (21 mg, 84%) as a pale yellow solid.

LRMS (m/z): 451, 453 (M+1)+.

Retention Time: 11 min.

¹H-NMR δ (CDCl₃): 2-2.18 (m, 5H), 2.46-2.63 (m, 2H), 3.09 (d, J=12.1 Hz, 2H), 3.64-3.81 (m, 3H), 4.73 (d, J=7.0 Hz, 1H), 6.69 (s, 1H), 6.99-7.10 (m, 2H), 7.26-7.48 (m, 6H), 8.38 (d, J=5.5 Hz, 1H).

Example 81

4-(2,4-Difluorophenyl)-8-(2-methylphenyl)-N-piperidin-4-yl-1,7-naphthyridin-2-amine a) 4-[4-(2,4-Difluorophenyl)-8-(2-methylphenyl)-1,7-naphthyridin-2-ylamino]-piperidine-1-carboxylic acid tert-butyl ester Obtained from the title compound of Preparation 47d following the experimental procedure described in Example 79a. The crude was purified by column chromatography on silica using ethyl acetate/hexane (1:3) as eluents, to yield the title compound (41%) as a white solid.

b) 4-(2,4-Difluorophenyl)-8-(2-methylphenyl)-N-piperidin-4-yl-1,7-naphthyridin-2-amine Obtained as a beige solid (89%) from the title compound of Example 81a following the experimental procedure described in Example 78b. (Reaction time: 2 h)

LRMS (m/z): 431 (M+1)+.

Retention Time: 9 min.

¹H-NMR δ (CDCl₃): 1.23-1.36 (m, 2H), 1.97 (d, J=12.4 Hz, 2H), 2.19 (s, 3H), 2.50-2.57 (m, 2H), 3.03 (d, J=12.4 Hz, 2H), 3.62-3.71 (m, 1H), 4.70 (d, J=6.6 Hz, 1H), 6.68 (s, 1H), 7-7.10 (m, 2H) 7.20-7.29 (m, 5H), 7.39-7.41 (m, 2H), 8.36 (d, J=5.5 Hz, 1H).

Example 82

8-(2,6-Dichlorophenyl)-4-(2,4-difluorophenyl)-2-piperazin-1-yl-1,7-naphthyridine a) 4-[8-(2,6-Dichlorophenyl)-4-(2,4-difluorophenyl)-1,7-naphthyridin-2-yl]-piperazine-1-carboxylic acid tert-butyl ester A mixture of the title compound of Preparation 44d (179 mg, 0.40 mmol) and tert-butyl 4-aminopiperidine-1-carboxylate (165 mg, 0.88 mmol) in ethoxyethanol (2 mL) was heated at 130° C. in a sealed tube for 3 h. The reaction was cooled down, diluted with ethyl acetate (40 mL), washed with water, brine, dried over sodium sulphate and the solvent was removed under reduced pressure. The residue was purified by column chromatography (C-18 silica from Waters©, reverse phase water/acetonitrile as eluents [0.1% v/v formic acid buffered] 0% to 60%) to yield the title compound (177 mg, 77%) as a solid.

b) 8-(2,6-Dichlorophenyl)-4-(2,4-difluorophenyl)-2-piperazin-1-yl-1,7-naphthyridine Obtained as a beige solid (52%) from the title compound of Example 82a following the experimental procedure described in Example 78b.

LRMS (m/z): 471, 473, 475 (M+1)+.

Retention Time: 12 min.

¹H-NMR δ (CDCl₃): 3.16-3.19 (m, 4H), 3.84-3.86 (m, 4H), 7.05-7.13 (m, 3H), 7.25-7.46 (m, 5H), 8.52 (d, J=6 Hz, 1H).

Example 83

4-(2,4-Difluorophenyl)-8-(2,6-difluorophenyl)-2-piperazin-1-yl-1,7-naphthyridine a) 4-[8-(2,6-Difluorophenyl)-4-(2,4-difluorophenyl)-1,7-naphthyridin-2-yl]-piperazine-1-carboxylic acid tert-butyl ester Obtained from the title compound of Preparation 45d following the experimental procedure described in Example 82a. The crude was purified by column chromatography on silica flash using ethyl acetate/hexane (8-100% of ethyl acetate) as eluents, to yield the title compound (85%) as a pale yellow solid.

b) 4-(2,4-difluorophenyl)-8-(2,6-difluorophenyl)-2-piperazin-1-yl-1,7-naphthyridine Obtained as a pale yellow solid (81%) from the title compound of Example 83a following the experimental procedure described in Example 78b. (Reaction time: 2 h)

LRMS (m/z): 439 (M+1)+.

Retention Time: 11 min.

¹H-NMR δ (CDCl₃): 2.91-2.94 (m, 4H), 3.57-3.60 (m, 4H), 3.71 (s, 1H), 7-7.09 (m, 6H), 7.30 (dd, J=5.6, 2.1 Hz, 1H), 7.37-7.43 (m, 1H), 8.43 (d, J=5.5 Hz, 1H).

Example 84

8-(2-chlorophenyl)-4-(2,4-difluorophenyl)-2-piperazin-1-yl-1,7-naphthyridine a) 4-[8-(2-Chlorophenyl)-4-(2,4-difluorophenyl)-1,7-naphthyridin-2-yl]-piperazine-1-carboxylic acid tent-butyl ester Obtained from the title compound of Preparation 46d following the experimental procedure described in Example 82a. The crude was purified by column chromatography on silica flash using ethyl acetate/hexane (4:1) as eluents, to yield the title compound (81%) as a pale yellow solid.

b) 8-(2-chlorophenyl)-4-(2,4-difluorophenyl)-2-piperazin-1-yl-1,7-naphthyridine

Obtained as a yellow solid (16%) from the title compound of Example 84a following the experimental procedure described in Example 78b. (Reaction time: 1 h)

LRMS (m/z): 437, 439 (M+1)+.

Retention Time: 11 min.

¹H-NMR δ (CDCl₃): 2.90-2.95 (m, 4H), 3.55-3.60 (m, 4H), 6.99-7.12 (m, 3H), 7.25-7.29 (m, 1H), 7.35-7.42 (m, 3H), 7.46-7.56 (m, 2H), 8.39 (d, J=5.5 Hz, 1H).

Example 85

4-(2,4-difluorophenyl)-8-(2-methylphenyl)-2-piperazin-1-yl-1,7-naphthyridine a) 4-[4-(2,4-Difluorophenyl)-8-(2-methylphenyl)-1,7naphthyridin-2-yl]-piperazine-1-carboxylic acid tert-butyl ester Obtained from the title compound of Preparation 47d following the experimental procedure described in Example 82a. The crude was purified by column chromatography on silica using ethyl acetate/hexane (1:3) as eluents, to yield the title compound (70%) as a pale yellow solid.

b) 4-(2,4-difluorophenyl)-8-(2-methylphenyl)-2-piperazin-1-yl-1,7-naphthyridine Obtained as a yellow solid (71%) from the title compound of Example 85a following the experimental procedure described in Example 78b. (Reaction time: 1 h)

LRMS (m/z): 417 (M+1)$^+$.

Retention Time: 10 min.

$^1$H-NMR δ (CDCl$_3$): 2.20 (s, 3H), 2.89-2.92 (m, 4H), 3.54-3.57 (m, 4H), 7.00-7.10 (m, 3H), 7.21-7.23 (m, 1H), 7.26-7.32 (m, 3H), 7.39-7.45 (m, 2H), 8.37 (d, J=5.5 Hz, 1H).

Example 86

8-(2,6-Dichlorophenyl)-4-(2,4-difluorophenyl)-N-piperidin-4-yl-1,7-naphthyridin-2-amine 7-oxide a) 4-[8-(2,6-Dichlorophenyl)-4-(2,4-difluorophenyl)-7-oxy-1,7-naphthyridin-2-ylamino]-piperidine-1-carboxylic acid tert-butyl ester A mixture of the title compound of Preparation 48b (300 mg, 0.69 mmol), tert-butyl 4-aminopiperidine-1-carboxylate (302 mg, 1.51 mmol) and diisopropylethylamine (194 mL, 1.51) in ethoxyethanol (3.6 mL) was heated at 130° C. in a sealed tube for 2 h 30 min. The reaction was cooled down, diluted with ethyl acetate (40 mL), washed with water, brine, dried over sodium sulphate and the solvent was removed under reduced pressure. The residue was purified by column chromatography (C-18 silica from Waters©, reverse phase water/acetonitrile as eluents [0.1% v/v formic acid buffered] 0% to 50%) to yield the title compound (105 mg, 25%) as a solid.

b) 8-(2,6-Dichlorophenyl)-4-(2,4-difluorophenyl)-N-piperidin-4-yl-1,7-naphthyridin-2-amine 7-oxide Obtained as a yellow solid (48%) from the title compound of Example 86a following the experimental procedure described in Example 78b.

LRMS (m/z): 501, 503, 505 (M+1)$^+$.

Retention Time: 10 min.

$^1$H-NMR δ (CDCl$_3$): 1.26-1.33 (m, 2H), 1.94-1.98 (m, 2H), 2.42-2.50 (m, 2H), 3.03-3.07 (m, 2H), 3.51-3.58 (m, 1H), 4.93 (d, J=6 Hz, 1H), 6.54 (s, 1H), 7.02-7.12 (m, 2N), 7.27-7.49 (m, 5H), 8.08 (d, J=9 Hz, 1H).

Example 87

4-(2,4-Difluorophenyl)-8-(2,6-difluorophenyl)-N-piperidin-4-yl-1,7-naphthyridin-2-amine 7-oxide a) 4-[8-(2,6-Difluorophenyl)-4-(2,4-difluorophenyl)-7-oxy-1,7-naphthyridin-2-ylamino]-piperidine-1-carboxylic acid tert-butyl ester Obtained from the title compound of Preparation 49b following the experimental procedure described in Example 78a. (Reaction time 3 h). The crude was purified by column chromatography on silica flash using ethyl acetate/hexane (4:1) as eluents, to yield the title compound (46%) as a pale yellow solid.

b) 4-(2,4-Difluorophenyl)-8-(2,6-difluorophenyl)-N-piperidin-4-yl-1,7-naphthyridin-2-amine 7-oxide Obtained as a white solid (74%) from the title compound of Example 87a following the experimental procedure described in Example 78b. (Reaction time: 1 h)

LRMS (m/z): 468 (M+1)$^+$.

Retention Time: 9 min.

$^1$H-NMR δ (CD$_3$OD): 1.36-1.43 (m, 2H), 1.92-1.99 (m, 2H), 2.15 (s, 1H), 2.42-2.53 (m, 2H), 2.99-3.06 (m, 2H), 3.57-3.66 (m, 1H), 6.81 (s, 1H), 7.12-7.23 (m, 4H), 7.47-7.64 (m, 3H), 8.09 (d, J=6.6 Hz, 1H).

Example 88

8-(2-Chlorophenyl)-4-(2,4-difluorophenyl)-N-piperidin-4-yl-1,7-naphthyridin-2-amine 7-oxide a) 4-[8-(2-Chlorophenyl)-4-(2,4-difluorophenyl)-7-oxy-1,7-naphthyridin-2-ylamino]-piperidine-1-carboxylic acid tert-butyl ester Obtained from the title compound of Preparation 50b following the experimental procedure described in Example 78a. (Reaction time 48 h). The crude was purified by column chromatography on silica flash using ethyl acetate/hexane (2:1) as eluents, to yield the title compound (39%) as a yellow solid.

b) 8-(2-Chlorophenyl)-4-(2,4-difluorophenyl)-N-piperidin-4-yl-1,7-naphthyridin-2-amine 7-oxide Obtained as a yellow solid (80%) from the title compound of Example 88a following the experimental procedure described in Example 78b.

LRMS (m/z): 467, 469 (M+1)$^+$.

Retention Time: 9 min.

$^1$H-NMR δ (CDCl$_3$): 1.23-1.28 (m, 2H), 1.86-1.98 (m, 2H), 2.45 (t, J=12.1 Hz, 2H), 2.98-3.05 (m, 2H, 3.46-3.61 (m, 1H), 4.85 (d, J=6.6 Hz, 1H), 6.51 (s, 1H), 6.98-7.12 (m, 2H), 7.20-7.25 (dd, J=7.2, 2.1 Hz, 2H), 7.38-7.44 (m, 3H), 7.52-7.57 (m, 1H), 8.06 (d, J=7.4 Hz, 1H).

Example 89

4-(2,4-Difluorophenyl)-8-(2-methylphenyl)-N-piperidin-4-yl-1,7-naphthyridin-2-amine 7-oxide a) 4-[4-(2,4-Difluorophenyl)-7-oxy-8-(2-methylphenyl)-1,7-naphthyridin-2-ylamino]-piperidine-1-carboxylic acid tert-butyl ester Obtained as a beige solid from the title compound of Preparation 51 b (59%) following the experimental procedure described in Example 78a. (Reaction time 17 h).

b) 4-(2,4-Difluorophenyl)-8-(2-methylphenyl)-N-piperidin-4-yl-1,7-naphthyridin-2-amine 7-oxide Obtained as a pale yellow solid (56%) from the title compound of Example 89a following the experimental procedure described in Example 78b. (Reaction time: 2 h).
LRMS (m/z): 447 (M+1)$^+$.
Retention Time: 9 min.
$^1$H-NMR δ (CDCl$_3$): 1.22-1.33 (m, 2H), 1.83-1.95 (m, 2H), 2.18 (s, 3H), 2.45 (t, J=12.1 Hz, 2H), 3.0 (d, J=12.1 Hz, 2H), 3.45-3.54 (m, 1H), 4.81 (d, J=5.5 Hz, 1H), 6.50 (s, 1H), 7.01-7.10 (m, 2H), 7.18-7.21 (m, 1H), 7.26-7.40 (m, 6H), 8.05-8.08 (m, 1H).

Example 90

8-(2,6-Dichlorophenyl)-4-(2,4-difluorophenyl)-2-piperazin-1-yl-1,7-naphthyridine 7-oxide a) 4-[8-(2,6-Dichlorophenyl)-4-(2,4-difluorophenyl)-7-oxy-1,7-naphthyridin-2-yl]-piperazine-1-carboxylic acid tert-butyl ester Obtained as a solid from the title compound of Preparation 48b (39%) following the experimental procedure described in Example 82a. (Reaction time 1 h 30 min).

b) 8-(2,6-Dichlorophenyl)-4-(2,4-difluorophenyl)-2-piperazin-1-yl-1,7-naphthyridine 7-oxide Obtained as a solid (52%) from the title compound of Example 90a following the experimental procedure described in Example 78b.
LRMS (m/z): 487, 489, 491 (M+1)$^+$.
Retention Time: 9 min.
$^1$H-NMR δ (CDCl$_3$): 2.85-2.88 (m, 4H), 3.49-3.52 (m, 4H), 6.87 (s, 1H), 7.01-7.11 (m, 2H), 7.25-7.48 (m, 5H), 8.06 (d, J=6 Hz, 1H).

Example 91

4-(2,4-Difluorophenyl)-8-(2,6-difluorophenyl)-2-piperazin-1-yl-1,7-naphthyridine 7-oxide a) 4-[8-(2,6-Difluorophenyl)-4-(2,4-difluorophenyl)-7-oxy-1,7-naphthyridin-2-yl]-piperazine-1-carboxylic acid tert-butyl ester Obtained from the title compound of Preparation 49b following the experimental procedure described in Example 82a. The crude was purified by column chromatography on silica flash using ethyl acetate/hexane (4:1) as eluents, to yield the title compound (44%) as a beige solid.

b) 4-(2,4-Difluorophenyl)-8-(2,6-difluorophenyl)-2-piperazin-1-yl-1,7-naphthyridine 7-oxide Obtained as a yellow solid (75%) from the title compound of Example 91a following the experimental procedure described in Example 78b. (Reaction time: 1 h).
LRMS (m/z): 454 (M+1)$^+$.
Retention Time: 9 min.
$^1$H-NMR δ (CDCl$_3$): 2.87-2.91 (m, 4H), 3.53-3.57 (m, 4H), 6.87 (s, 1H), 7.03-7.08 (m, 4H), 7.23-7.25 (m, 1H), 7.33-7.38 (m, 1H), 7.42-7.51 (m, 1H), 8.07 (d, J=7.1 Hz, 1H).

Example 92

8-(2-Chlorophenyl)-4-(2,4-difluorophenyl)-2-piperazin-1-yl-1,7-naphthyridine 7-oxide a) 4-[8-(2-Chlorophenyl)-4-(2,4-difluorophenyl)-7-oxy-1,7-naphthyridin-2-yl]-piperazine-1-carboxylic acid tert-butyl ester Obtained from the title compound of Preparation 50b following the experimental procedure described in Example 82a. (Reaction time 1 h). The crude was purified by column chromatography on silica flash using ethyl acetate/hexane (4:1) as eluents, to yield the title compound (82%) as a yellow foam.

b) 8-(2-Chlorophenyl)-4-(2,4-difluorophenyl)-2-piperazin-1-yl-1,7-naphthyridine 7-oxide Obtained as a yellow solid (59%) from the title compound of Example 92a following the experimental procedure described in Example 78b. (Reaction time: 1 h).
LRMS (m/z): 452, 454 (M+1)$^+$.
Retention Time: 9 min.
$^1$H-NMR δ (CDCl$_3$): 2.88-2.89 (m, 4H), 3.51-3.52 (m, 4H), 6.86 (s, 1H), 7.01-7.12 (m, 2H), 7.22-7.26 (m, 1H), 7.41-7.44 (m, 4H), 7.55-7.59 (m, 1H) 8.07 (d, J=7.1 Hz, 1H).

Example 93

4-(2,4-Difluorophenyl)-8-(2-methylphenyl)-2-piperazin-1-yl-1,7-naphthyridine 7-oxide a) 4-[4-(2,4-Difluorophenyl)-7-oxy-8-(2-methylphenyl)-1,7-naphthyridin-2-yl]-piperazine-1-carboxylic acid tert-butyl ester Obtained from the title compound of Preparation 51 b following the experimental procedure described in Example 82a. (Reaction time 4 h). The crude was purified by column chromatography on silica flash using ethyl acetate/hexane (40 to 67% of ethyl acetate) as eluents, to yield the title compound (58%) as yellow solid.

b) 4-(2,4-Difluorophenyl)-8-(2-methylphenyl)-2-piperazin-1-yl-1,7-naphthyridine 7-oxide Obtained as a solid (82%) from the title compound of Example 93a following the experimental procedure described in Example 78b. (Reaction time: 2 h).
LRMS (m/z): 433 (M+1)$^+$.
Retention Time: 8 min.
$^1$H-NMR δ (CDCl$_3$): 2.18 (s, 3H), 2.85 (brs, 4H), 3.48 (brs, 4H), 6.85 (s, 1H), 7.01-7.10 (m, 2H), 7.19 (d, J=6.6 Hz, 1H), 7.27-7.42 (m, 5H), 8.06 (d, J=7.1 Hz, 1H).

Example 94

8-(2,6-Dichlorophenyl)-4-(2,4-difluorophenyl)-N-(1,2,2,6,6-pentamethylpiperidin-4-yl)-1,7-naphthyridin-2-amine 7-oxide Obtained as a solid (22%) from the title compound of Preparation 48b following the experimental procedure described in Example 86a.
LRMS (m/z): 571, 573, 575 (M+1)$^+$.
Retention Time: 10 min.
$^1$H-NMR δ (CDCl$_3$): 1.11 (s, 6H), 1.45 (s, 6H), 1.90-1.94 (m, 2H), 2.29-2.38 (m, 2H), 2.66 (s, 3H), 4.30-4.35 (m, 1H), 6.16 (d, J=6 Hz, 1H), 6.64 (s, 1H), 7.00-7.10 (m, 2H), 7.27-7.45 (m, 5H), 8.07 (d, J=9 Hz, 1H).

Example 95

8-(2,6-Dichlorophenyl)-4-(2,4-difluorophenyl)-2-(piperidin-4-yloxy)-1,7-naphthyridine 7-oxide a) 4-[8-(2,6-Dichlorophenyl)-4-(2,4-difluorophenyl)-1,7-naphthyridin-2-yloxy]-piperidine-1-carboxylic acid tert-butyl ester A mixture of the title compound of Preparation 48b (308 mg, 0.70 mmol), tert-butyl 4-hydroxypiperidine-1-carboxylate (340 mg, 1.69 mmol), potassium hydroxide (79 mg, 1.41 mmol) and 1,4,7,10,13,16-hexaoxacyclooctadecane (74 mg, 0.28) in toluene (3 mL) was heated at 110° C. in a vial for 3 h. The reaction was cooled down, filtered and purified by column chromatography on silica flash using hexane/ethyl acetate (0 to 100% of ethyl acetate) as eluents, to yield the title compound (172 mg, 40%) as a solid.

b) 8-(2,6-Dichlorophenyl)-4-(2,4-difluorophenyl)-2-(piperidin-4-yloxy)-1,7-naphthyridine 7-oxide Obtained as a yellow solid (37%) from the title compound of Example 95a following the experimental procedure described in Example 78b.
LRMS (m/z): 502, 504, 506 (M+1)$^+$.
Retention Time: 10 min.
$^1$H-NMR δ (CDCl$_3$): 2.02-2.05 (m, 4H), 2.98-3.00 (m, 2H), 3.19-3.28 (m, 2H), 4.91 (m, 1H), 6.91 (s, 1H), 7.05-7.15 (m, 2H), 7.39-7.51 (m, 5H), 8.25 (d, J=6 Hz, 1H), 8.50 (brs, 1H).

Example 96

4-(2,4-Difluorophenyl)-8-(2,6-difluorophenyl)-2-(piperidin-4-yloxy)-1,7-naphthyridine 7-oxide a) 4-[4-(2,4-Difluorophenyl)-8-(2,6-difluorophenyl)-7-oxy-1,7-naphthyridin-2-yloxy]-piperidine-1-carboxylic acid tert-butyl ester Obtained as a white solid (29%) from the title compound of Preparation 49b following the experimental procedure described in Example 95a.

b) 4-(2,4-Difluorophenyl)-8-(2,6-difluorophenyl)-2-(piperidin-4-yloxy)-1,7-naphthyridine 7-oxide Obtained as a solid (83%) from the title compound of Example 96a following the experimental procedure described in Example 78b. (Reaction time: 1 h).

LRMS (m/z): 470 (M+1)$^+$.
Retention Time: 9 min.
$^1$H-NMR δ (CD$_3$OD): 0.87-0.96 (m, 1H), 1.26-1.32 (m, 1H), 1.59-1.69 (m, 2H), 1.96-2.0 (m, 2H), 2.51-2.58 (m, 2H), 3.0-3.07 (m, 2H), 7.10 (s, 1H), 7.18-7.30 (m, 4H), 7.55-7.72 (m, 3H), 8.33 (d, J=7.1 Hz, 1H).

Composition Example 1

50,000 capsules each containing 100 mg of 8-(2-Chlorophenyl)-4-(2,4-difluorophenyl)-1,7-naphthyridine 7-oxide (active ingredient) were prepared according to the following formulation:

| Active ingredient | 5 Kg |
|---|---|
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets each containing 50 mg 8-(2-Chlorophenyl)-4-(2,4-difluorophenyl)-1,7-naphthyridine 7-oxide (active ingredient) were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:
1. A compound of formula (I)

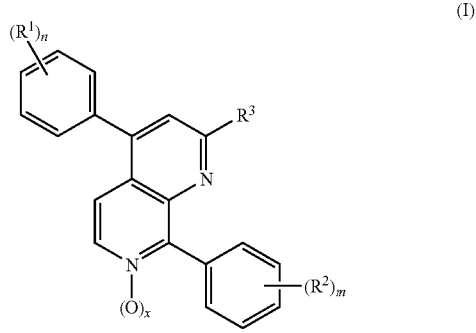

wherein:

each instance of $R^1$ is independently chosen from halogen atoms, $C_{1-4}$ alkyl groups optionally substituted by one, two or three halogen atoms and $C_{1-4}$ alkoxy groups;

each instance of $R^2$ is independently chosen from halogen atoms, hydroxy, $C_{1-4}$ alkyl, $C_{1-4}$ alkoxy, $C_{1-4}$ alkylthio, $C_{1-4}$ alkoxy-$C_{1-4}$ alkoxy, morpholin-$C_{1-4}$ alkoxy, $C_{1-4}$ alkanesulfonamide and $C_{1-4}$ alkoxy-$C_{1-4}$ alkylcarbamoyl groups;

$R^3$ is chosen from a hydrogen atom and -L-$G^1$ wherein L is a linker chosen from a direct bond, —O—, —S— and —NH—;

and $G^1$ chosen from aromatic heterocycles or non-aromatic heterocycles having one ring or two or more fused rings wherein, independently, the aromatic heterocycles, or non-aromatic heterocycles are optionally substituted with one or two groups chosen from halogen atoms, amino groups, mono- or di-$C_{1-4}$ alkylamino groups, $C_{1-4}$ alkyl groups, $C_{1-4}$ alkoxy groups and $C_{3-6}$ cycloalkyl groups;

n is an integer from 0 to 4 m is an integer from 0 to 4; and x has the value of zero or one;

or a pharmaceutically acceptable salt thereof.

2. The compound according to claim 1, wherein x has a value of 1.

3. The compound according to claim 1, wherein n is 1 or 2 and each instance of $R^1$ is independently chosen from halogen atoms and $C_{1-4}$ alkyl groups.

4. The compound according to claim 3, wherein at least one group $R^1$ is at an ortho position with respect to the carbon atom through which the phenyl group is attached to the naphtyridine core.

5. The compound according to claim 4, wherein n is 2, and both groups $R^1$ are halogen atoms.

6. The compound according to claim 5, wherein both groups $R^1$ are chosen from chlorine and fluorine atoms.

7. The compound according to claim 1, wherein m is 1 or 2 and each instance of $R^2$ is independently chosen from halogen atoms and $C_{1-4}$ alkyl groups.

8. The compound according to claim 7, wherein at least one group $R^2$ is at an ortho position with respect to the carbon atom through which the phenyl group is attached to the naphtyridine core.

9. The compound according to claim 8, wherein m is 2 and the two groups $R^2$ are at an ortho position with respect to the carbon atom through which the phenyl group is attached to the naphtyridine core.

10. The compound according to claim 9, wherein both $R^2$ groups are halogen atoms.

11. The compound according to claim 10, wherein both groups $R^2$ are identical and are chosen from chlorine and fluorine atoms.

12. The compound according to claim 1, wherein $R^3$ is chosen from a hydrogen atom and L-$G^1$ wherein L is a linker chosen from a direct bond, —O—, —S— and —NH—; and $G^1$ is chosen from optionally substituted, nitrogen-containing, aromatic heterocycles or non-aromatic heterocycles, having one ring or two or more fused rings.

13. The compound according to claim 12, wherein $R^3$ is chosen from a hydrogen atom and:

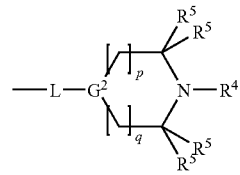

wherein $G^2$ is chosen from —CH— and —N—;

p and q are independently 0, 1 or 2;

$R^4$ is chosen from a hydrogen atom and straight or branched $C_{1-4}$ alkyl groups, and each instance of $R^5$ is independently chosen from a hydrogen atom and methyl.

14. The compound according to claim 13, wherein $R^3$ is chosen from a hydrogen atom and 1-tert-butylpiperidin-4-yl.

15. The compound according to claim 1, chosen from 4-(2,4-Difluorophenyl)-8-(2-methylphenyl)-1,7-naphthyridine 4-(2,4-Difluorophenyl)-8-(2-methoxyphenyl)-1,7-naphthyridine 4-[4-(2,4-Difluorophenyl)-1,7-naphthyridin-8-yl]-3-methylphenol 8-(1,3-Benzodioxol-4-yl)-4-(2,4-difluorophenyl)-1,7-naphthyridine 4-(2,4-Difluorophenyl)-8-(2,6-difluorophenyl)-1,7-naphthyridine 4-(2,4-Difluorophenyl)-8-[4-(2-methoxyethoxy)-2-methylphenyl]-1,7-naphthyridine 4-(2,4-Difluorophenyl)-8-[2-methyl-4-(2-morpholin-4-ylethoxy)phenyl]-1,7-naphthyridine 4-(2,4-Difluorophenyl)-8-(2,6-dimethylphenyl)-1,7-naphthyridine 4-(2,4-Difluorophenyl)-8-(2,6-dimethoxyphenyl)-1,7-naphthyridine 4-(2,4-Difluorophenyl)-8-(2-methylphenyl)-2-piperidin-4-yl-1,7-naphthyridine 8-(2-Chlorophenyl)-4-(2,4-difluorophenyl)-2-piperidin-4-yl-1,7-naphthyridine 4-(2,4-Difluorophenyl)-8-(2-fluorophenyl)-2-piperidin-4-yl-1,7-naphthyridine 4-(2,4-Difluorophenyl)-8-(2,6-difluorophenyl)-2-piperidin-4-yl-1,7-naphthyridine 8-(2,6-Dichlorophenyl)-4-(2,4-difluorophenyl)-2-piperidin-4-yl-1,7-naphthyridine 4-(2,4-Difluorophenyl)-8-(2-methylphenyl)-1,7-naphthyridine 7-oxide 4-(2,4-Difluorophenyl)-8-(2-methoxyphenyl)-1,7-naphthyridine 7-oxide 4-[4-(2,4-Difluorophenyl)-7-oxido-1,7-naphthyridin-8-yl]-3-methylphenol 8-(1,3-Benzodioxol-4-yl)-4-(2,4-difluorophenyl)-1,7-naphthyridine 7-oxide 4-(2,4-Difluorophenyl)-8-(2,6-difluorophenyl)-1,7-naphthyridine 7-oxide 4-(2,4-Difluorophenyl)-8-(2,6-dimethylphenyl)-1,7-naphthyridine 7-oxide 4-(2,4-Difluorophenyl)-8-(2,6-dimethoxyphenyl)-1,7-naphthyridine 7-oxide N-{4-[4-(2,4-Difluorophenyl)-7-oxido-1,7-naphthyridin-8-yl]-3-methylphenyl}methane-sulfonamide 8-(2-Chlorophenyl)-4-(2,4-difluorophenyl)-1,7-naphthy-ridine 7-oxide
4-(2,4-Difluorophenyl)-8-(2-fluorophenyl)-1,7-naphthy-ridine 7-oxide
8-(2,6-Dichlorophenyl)-4-(2,4-difluorophenyl)-1,7-naph-thyridine 7-oxide
4-(2,4-Difluorophenyl)-8-(2-methylphenyl)-2-piperidin-4-yl-1,7-naphthyridine 7-oxide
8-(2-Chlorophenyl)-4-(2,4-difluorophenyl)-2-piperidin-4-yl-1,7-naphthyridine 7-oxide
4-(2,4-Difluorophenyl)-8-(2-fluorophenyl)-2-piperidin-4-yl-1,7-naphthyridine 7-oxide
4-(2,4-Difluorophenyl)-8-(2,6-difluorophenyl)-2-piperidin-4-yl-1,7-naphthyridine 7-oxide
8-(2,6-dichlorophenyl)-4-(2,4-difluorophenyl)-2-(piperidin-4-yl)-1,7-naphthyridine 7-oxide
4-(2,4-Difluorophenyl)-8-(2,6-difluorophenyl)-2-(1-methylpiperidin-4-yl)-1,7-naphthyridine 7-oxide
8-(2,6-Dichlorophenyl)-4-(2,4-difluorophenyl)-2-(1-methylpiperidin-4-yl)-1,7-naphthyridine 7-oxide
4-(2,4-Difluorophenyl)-8-(2,6-difluorophenyl)-2-(1-isopropylpiperidin-4-yl)-1,7-naphthyridine 7-oxide
8-(2,6-Dichlorophenyl)-4-(2,4-difluorophenyl)-2-(1-isopropylpiperidin-4-yl)-1,7-naphthyridine 7-oxide
2-(1-Tert-butylpiperidin-4-yl)-4-(2,4-difluorophenyl)-8-(2,6-difluorophenyl)-1,7-naphthyridine 7-oxide
2-(1-Tert-butylpiperidin-4-yl)-8-(2,6-dichlorophenyl)-4-(2,4-difluorophenyl)-1,7-naphthyridine 7-oxide
4-(2-Chloro-4-fluorophenyl)-8-(2,6-difluorophenyl)-2-piperidin-4-yl-1,7-naphthyridine
4-(2-Chloro-4-fluorophenyl)-8-(2,6-dichlorophenyl)-2-piperidin-4-yl-1,7-naphthyridine
4-(2-Chloro-4-fluorophenyl)-8-(2,6-difluorophenyl)-1,7-naphthyridine 7-oxide
4-(2-Chloro-4-fluorophenyl)-8-(2,6-dichlorophenyl)-1,7-naphthyridine 7-oxide
4-(2-Chloro-4-fluorophenyl)-8-(2-chlorophenyl)-2-piperidin-4-yl-1,7-naphthyridine 7-oxide
4-(2-Chloro-4-fluorophenyl)-8-(2,6-difluorophenyl)-2-piperidin-4-yl-1,7-naphthyridine 7-oxide
4-(2-Chloro-4-fluorophenyl)-8-(2,6-dichlorophenyl)-2-piperidin-4-yl-1,7-naphthyridine 7-oxide
4-(2-Chloro-4-fluorophenyl)-8-(2,6-difluorophenyl)-2-(1-methylpiperidin-4-yl)-1,7-naphthyridine 7-oxide
4-(2-Chloro-4-fluorophenyl)-8-(2,6-dichlorophenyl)-2-(1-methylpiperidin-4-yl)-1,7-naphthyridine 7-oxide
4-(2-Chloro-4-fluorophenyl)-8-(2,6-difluorophenyl)-2-(1-isopropylpiperidin-4-yl)-1,7-naphthyridine 7-oxide
4-(2-Chloro-4-fluorophenyl)-8-(2,6-dichlorophenyl)-2-(1-isopropylpiperidin-4-yl)-1,7-naphthyridine 7-oxide
2-(1-Tert-butylpiperidin-4-yl)-4-(2-chloro-4-fluorophenyl)-8-(2,6-difluorophenyl)-1,7-naphthyridine 7-oxide
2-(1-Tert-butylpiperidin-4-yl)-4-(2-chloro-4-fluorophenyl)-8-(2,6-dichlorophenyl)-1,7-naphthyridine 7-oxide
4-(2-Chlorophenyl)-8-(2,6-difluorophenyl)-2-piperidin-4-yl-1,7-naphthyridine
4-(2-Chlorophenyl)-8-(2,6-dichlorophenyl)-2-piperidin-4-yl-1,7-naphthyridine
4-(2-Chlorophenyl)-8-(2,6-difluorophenyl)-2-piperidin-4-yl-1,7-naphthyridine 7-oxide
4-(2-Chlorophenyl)-8-(2,6-dichlorophenyl)-2-piperidin-4-yl-1,7-naphthyridine 7-oxide
4-(2-Chlorophenyl)-8-(2,6-difluorophenyl)-2-(1-methylpiperidin-4-yl)-1,7-naphthyri-dine 7-oxide
4-(2-Chlorophenyl)-8-(2,6-dichlorophenyl)-2-(1-methylpiperidin-4-yl)-1,7-naphthyri-dine 7-oxide
4-(2-Chlorophenyl)-8-(2,6-difluorophenyl)-2-(1-isopropylpiperidin-4-yl)-1,7-naphthy-ridine 7-oxide
4-(2-Chlorophenyl)-8-(2,6-dichlorophenyl)-2-(1-isopropylpiperidin-4-yl)-1,7-naphthy-ridine 7-oxide
2-(1-Tert-butylpiperidin-4-yl)-4-(2-chlorophenyl)-8-(2,6-difluorophenyl)-1,7-naphthy-ridine 7-oxide
2-(1-Tert-butylpiperidin-4-yl)-4-(2-chlorophenyl)-8-(2,6-dichlorophenyl)-1,7-naphthy-ridine 7-oxide
8-(2,6-Difluorophenyl)-4-(2-methoxyphenyl)-1,7-naphthyridine
8-(2,6-Dimethylphenyl)-4-(2-methoxyphenyl)-1,7-naphthyridine
N-{4-[4-(2-methoxyphenyl)-1,7-naphthyridin-8-yl]-3-methylphenyl}methanesulfon-amide
8-(2,6-Difluorophenyl)-4-(2-methoxyphenyl)-1,7-naphthyridine 7-oxide
8-(2,6-Dimethylphenyl)-4-(2-methoxyphenyl)-1,7-naphthyridine 7-oxide
N-{4-[4-(2-methoxyphenyl)-7-oxido-1,7-naphthyridin-8-yl]-3-methylphenyl}methane-sulfonamide
8-(2-Chlorophenyl)-4-(2-methoxyphenyl)-1,7-naphthyridine 7-oxide
4,8-Bis(2-methoxyphenyl)-1,7-naphthyridine 7-oxide
8-(2-Methoxyphenyl)-4-[3-(trifluoromethyl)phenyl]-1,7-naphthyridine 7-oxide
8-(2,6-Difluorophenyl)-4-[3-(trifluoromethyl)phenyl]-1,7-naphthyridine 7-oxide
8-(2,6-Dichlorophenyl)-4-[3-(trifluoromethyl)phenyl]-1,7-naphthyridine 7-oxide
8-(2-Methoxyphenyl)-4-[3-(trifluoromethyl)phenyl]-2-piperidin-4-yl-1,7-naphthyridine 7-oxide
8-(2,6-Difluorophenyl)-4-[3-(trifluoromethyl)phenyl]-2-piperidin-4-yl-1,7-naphthyri-dine 7-oxide
8-(2,6-Dichlorophenyl)-4-[3-(trifluoromethyl)phenyl]-2-piperidin-4-yl-1,7-naphthyri-dine 7-oxide
8-(2,6-Difluorophenyl)-4-[4-(trifluoromethyl)phenyl]-1,7-naphthyridine 7-oxide
8-(2,6-dichlorophenyl)-4-[4-(trifluoromethyl)phenyl]-1,7-naphthyridine 7-oxide
8-(2,6-difluorophenyl)-4-[4-(trifluoromethyl)phenyl]-2-piperidin-4-yl-1,7-naphthyri-dine 7-oxide
8-(2,6-Dichlorophenyl)-4-[4-(trifluoromethyl)phenyl]-2-piperidin-4-yl-1,7-naphthyri-dine 7-oxide
8-(2,6-Dichlorophenyl)-4-(2,4-difluorophenyl)-N-piperidin-4-yl-1,7-naphthyridin-2-amine
4-(2,4-Difluorophenyl)-8-(2,6-difluorophenyl)-N-piperidin-4-yl-1,7-naphthyridin-2-amine
8-(2-Chlorophenyl)-4-(2,4-difluorophenyl)-N-piperidin-4-yl-1,7-naphthyridin-2-amine
4-(2,4-Difluorophenyl)-8-(2-methylphenyl)-N-piperidin-4-yl-1,7-naphthyridin-2-amine
8-(2,6-Dichlorophenyl)-4-(2,4-difluorophenyl)-2-piperazin-1-yl-1,7-naphthyridine
4-(2,4-Difluorophenyl)-8-(2,6-difluorophenyl)-2-piperazin-1-yl-1,7-naphthyridine
8-(2-chlorophenyl)-4-(2,4-difluorophenyl)-2-piperazin-1-yl-1,7-naphthyridine
4-(2,4-difluorophenyl)-8-(2-methylphenyl)-2-piperazin-1-yl-1,7-naphthyridine
8-(2,6-Dichlorophenyl)-4-(2,4-difluorophenyl)-N-piperidin-4-yl-1,7-naphthyridin-2-amine 7-oxide
4-(2,4-Difluorophenyl)-8-(2,6-difluorophenyl)-N-piperidin-4-yl-1,7-naphthyridin-2-amine 7-oxide
8-(2-Chlorophenyl)-4-(2,4-difluorophenyl)-N-piperidin-4-yl-1,7-naphthyridin-2-amine 7-oxide
4-(2,4-Difluorophenyl)-8-(2-methylphenyl)-N-piperidin-4-yl-1,7-naphthyridin-2-amine 7-oxide 8-(2,6-Dichlorophenyl)-4-(2,4-difluorophenyl)-2-piperazin-1-yl-1,7-naphthyridine 7-oxide 4-(2,4-Difluorophenyl)-8-(2,6-difluorophenyl)-2-piperazin-1-yl-1,7-naphthyridine 7-oxide 8-(2-Chlorophenyl)-4-(2,4-difluorophenyl)-2-piperazin-1-yl-1,7-naphthyridine 7-oxide 4-(2,4-Difluorophenyl)-8-(2-methylphenyl)-2-piperazin-1-yl-1,7-naphthyridine 7-oxide 8-(2,6-Dichlorophenyl)-4-(2,4-difluorophenyl)-N-(1,2,2,6,6-pentamethylpiperidin-4-yl)-1,7-naphthyridin-2-amine 7-oxide 8-(2,6-Dichlorophenyl)-4-(2,4-difluorophenyl)-2-(piperidin-4-yloxy)-1,7-naphthyridine 7-oxide 4-(2,4-Difluorophenyl)-8-(2,6-difluorophenyl)-2-(piperidin-4-yloxy)-1,7-naphthyridine 7-oxide; and a pharmaceutically acceptable salt thereof.

16. A pharmaceutical composition comprising a compound as claimed in claim 1 and a pharmaceutically acceptable diluent or carrier.

* * * * *